United States Patent
McDonough et al.

(10) Patent No.: US 9,241,809 B2
(45) Date of Patent: Jan. 26, 2016

(54) INTERVERTEBRAL IMPLANTS, SYSTEMS, AND METHODS OF USE

(71) Applicant: DePuy Synthes Products, Inc., Raynham, MA (US)

(72) Inventors: William P. McDonough, Collegeville, PA (US); William L. Strausbaugh, West Chester, PA (US); Benjamin Chronister, West Chester, PA (US); Thomas Pepe, West Chester, PA (US); Michael Coover, West Chester, PA (US); Katharine Coffman, West Chester, PA (US); Thomas Kueenzi, West Chester, PA (US); Edwin Chan, West Chester, PA (US); Peyman Pakzaban, Pasadena, TX (US); Kurt Schmura, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 13/767,097

(22) Filed: Feb. 14, 2013

(65) Prior Publication Data

US 2013/0166032 A1  Jun. 27, 2013

Related U.S. Application Data

(63) Continuation-in-part of application No. 13/333,065, filed on Dec. 21, 2011.

(60) Provisional application No. 61/425,505, filed on Dec. 21, 2010, provisional application No. 61/425,509, filed on Dec. 21, 2010.

(51) Int. Cl.
*A61F 2/44* (2006.01)
*A61B 17/17* (2006.01)
(Continued)

(52) U.S. Cl.
CPC ........... *A61F 2/4455* (2013.01); *A61B 17/1757* (2013.01); *A61F 2/4611* (2013.01);
(Continued)

(58) Field of Classification Search
CPC .......... A61B 17/8061; A61B 17/8057; A61B 17/808
USPC ..................... 606/246–249; 623/17.11–17.16
See application file for complete search history.

(56) References Cited

U.S. PATENT DOCUMENTS

| 424,836 A | 4/1890 | Thompson |
| 1,105,105 A | 7/1914 | Sherman |

(Continued)

FOREIGN PATENT DOCUMENTS

| AU | 2004232317 | 11/2004 |
| AU | 2004/232317 | 11/2010 |

(Continued)

OTHER PUBLICATIONS

International Patent Application No. PCT/US2011/066421: International Search Report and Written Opinion dated Jun. 14, 2012, 31 pages.

(Continued)

*Primary Examiner* — Mary Hoffman
*Assistant Examiner* — Tara R Carter
(74) *Attorney, Agent, or Firm* — Baker & Hostetler LLP

(57) ABSTRACT

An intervertebral implant frame that is configured to be attached to a spacer body can include a pair of arms that extend longitudinally from a support member such that the arms extend substantially around the spacer body. The arms may be configured to expand, crimp, or otherwise engage the spacer body to thereby hold the spacer body to the frame. The spacer body may be made from bone graft.

14 Claims, 31 Drawing Sheets

(51) Int. Cl.
  *A61F 2/46* (2006.01)
  *A61F 2/28* (2006.01)
  *A61F 2/30* (2006.01)
  *A61B 17/86* (2006.01)

(52) U.S. Cl.
  CPC . *A61B 17/86* (2013.01); *A61F 2/28* (2013.01); *A61F 2/3094* (2013.01); *A61F 2002/2835* (2013.01); *A61F 2002/305* (2013.01); *A61F 2002/30131* (2013.01); *A61F 2002/30387* (2013.01); *A61F 2002/30477* (2013.01); *A61F 2002/30571* (2013.01); *A61F 2002/30576* (2013.01); *A61F 2002/30604* (2013.01); *A61F 2002/30774* (2013.01); *A61F 2002/30787* (2013.01); *A61F 2002/4622* (2013.01); *A61F 2310/00023* (2013.01); *A61F 2310/00131* (2013.01); *A61F 2310/00293* (2013.01); *A61F 2310/00299* (2013.01); *A61F 2310/00359* (2013.01)

(56) References Cited

U.S. PATENT DOCUMENTS

| | | | |
|---|---|---|---|
| 1,200,797 | A | 10/1916 | Barbe |
| 2,151,919 | A | 3/1939 | Jacobson |
| 2,372,888 | A | 4/1945 | Edward |
| 2,621,145 | A | 12/1952 | Sano |
| 2,782,827 | A | 2/1957 | Joseph |
| 2,906,311 | A | 9/1959 | Boyd |
| 2,972,367 | A | 2/1961 | Wootton |
| 3,062,253 | A | 11/1962 | Melvin |
| 3,272,249 | A | 9/1966 | Houston |
| 3,350,103 | A | 10/1967 | Ahlstone |
| 3,561,075 | A | 2/1971 | Selinko |
| 3,579,831 | A | 5/1971 | Stevens et al. |
| 3,707,303 | A | 12/1972 | Petri |
| 3,810,703 | A | 5/1974 | Pasbrig |
| 3,899,897 | A | 8/1975 | Boerger et al. |
| 3,945,671 | A | 3/1976 | Gerlach |
| 4,017,946 | A | 4/1977 | Soja |
| 4,056,301 | A | 11/1977 | Norden |
| 4,123,132 | A | 10/1978 | Hardy |
| 4,135,506 | A | 1/1979 | Ulrich |
| 4,278,120 | A | 7/1981 | Hart et al. |
| 4,280,875 | A | 7/1981 | Werres |
| 4,285,377 | A | 8/1981 | Hart |
| 4,288,902 | A | 9/1981 | Franz |
| 4,297,063 | A | 10/1981 | Hart |
| 4,299,902 | A | 11/1981 | Soma et al. |
| 4,388,921 | A | 6/1983 | Sutter et al. |
| 4,484,570 | A | 11/1984 | Sutter et al. |
| 4,488,543 | A | 12/1984 | Tornier |
| 4,501,269 | A | 2/1985 | Bagby |
| 4,503,848 | A | 3/1985 | Caspar et al. |
| 4,512,038 | A | 4/1985 | Alexander et al. |
| 4,553,890 | A | 11/1985 | Gulistan |
| 4,599,086 | A | 7/1986 | Doty |
| 4,627,853 | A | 12/1986 | Campbell et al. |
| 4,640,524 | A | 2/1987 | Sedlmair |
| 4,648,768 | A | 3/1987 | Hambric |
| 4,678,470 | A | 7/1987 | Nashef et al. |
| 4,708,377 | A | 11/1987 | Hunting |
| 4,711,760 | A | 12/1987 | Blaushild |
| 4,717,115 | A | 1/1988 | Schmitz et al. |
| 4,793,335 | A | 12/1988 | Frey et al. |
| 4,804,290 | A | 2/1989 | Balsells |
| 4,812,094 | A | 3/1989 | Grube |
| 4,858,603 | A | 8/1989 | Clemow et al. |
| 4,904,261 | A | 2/1990 | Dove et al. |
| 4,936,851 | A | 6/1990 | Fox et al. |
| 4,950,296 | A | 8/1990 | Mcintyre |
| 4,955,908 | A | 9/1990 | Frey et al. |
| 4,961,740 | A | 10/1990 | Ray et al. |
| 4,976,576 | A | 12/1990 | Mahaney |
| 4,978,350 | A | 12/1990 | Wagenknecht |
| 4,994,084 | A | 2/1991 | Brennan |
| 5,010,783 | A | 4/1991 | Sparks et al. |
| 5,017,069 | A | 5/1991 | Stencel |
| 5,020,949 | A | 6/1991 | Davidson et al. |
| 5,026,373 | A | 6/1991 | Ray et al. |
| 5,030,220 | A | 7/1991 | Howland |
| 5,053,049 | A | 10/1991 | Campbell |
| 5,062,850 | A | 11/1991 | MacMillan et al. |
| 5,071,437 | A | 12/1991 | Steffee |
| 5,084,051 | A | 1/1992 | Tormala et al. |
| 5,085,660 | A | 2/1992 | Lin |
| 5,096,150 | A | 3/1992 | Westwood |
| 5,108,438 | A | 4/1992 | Stone |
| 5,112,354 | A | 5/1992 | Sires |
| 5,118,235 | A | 6/1992 | Dill |
| 5,139,424 | A | 8/1992 | Yli-Urpo |
| 5,147,404 | A | 9/1992 | Downey |
| 5,180,381 | A | 1/1993 | Aust et al. |
| 5,192,327 | A | 3/1993 | Brantigan |
| 5,207,543 | A | 5/1993 | Kirma |
| 5,211,664 | A | 5/1993 | Tepic et al. |
| 5,235,034 | A | 8/1993 | Bobsein et al. |
| 5,238,342 | A | 8/1993 | Stencel |
| 5,275,601 | A | 1/1994 | Gogolewski et al. |
| 5,281,226 | A | 1/1994 | Davydov et al. |
| 5,284,655 | A | 2/1994 | Bogdansky et al. |
| 5,290,312 | A | 3/1994 | Kojimoto et al. |
| 5,298,254 | A | 3/1994 | Prewett et al. |
| 5,304,021 | A | 4/1994 | Oliver et al. |
| 5,314,476 | A | 5/1994 | Prewett et al. |
| 5,314,477 | A | 5/1994 | Marnay |
| 5,330,535 | A | 7/1994 | Moser et al. |
| 5,348,788 | A | 9/1994 | White |
| 5,368,593 | A | 11/1994 | Stark |
| 5,380,323 | A | 1/1995 | Howland |
| 5,385,583 | A | 1/1995 | Cotrel |
| 5,397,364 | A | 3/1995 | Kozak et al. |
| 5,405,391 | A | 4/1995 | Hednerson et al. |
| 5,411,348 | A | 5/1995 | Balsells |
| 5,423,817 | A | 6/1995 | Lin |
| 5,425,772 | A | 6/1995 | Brantigan |
| 5,439,684 | A | 8/1995 | Prewett et al. |
| 5,458,638 | A | 10/1995 | Kuslich et al. |
| 5,458,641 | A | 10/1995 | Ramirez |
| 5,458,643 | A | 10/1995 | Oka et al. |
| 5,478,342 | A | 12/1995 | Kohrs |
| 5,487,744 | A | 1/1996 | Howland |
| 5,489,308 | A | 2/1996 | Kuslich et al. |
| 5,507,818 | A | 4/1996 | McLaughlin |
| 5,514,180 | A | 5/1996 | Heggeness et al. |
| 5,520,690 | A | 5/1996 | Errico et al. |
| 5,522,899 | A | 6/1996 | Michelson |
| 5,531,746 | A | 7/1996 | Errico et al. |
| 5,534,030 | A | 7/1996 | Navarro et al. |
| 5,534,031 | A | 7/1996 | Matsuzaki et al. |
| 5,534,032 | A | 7/1996 | Hodorek |
| 5,545,842 | A | 8/1996 | Balsells |
| 5,549,612 | A | 8/1996 | Yapp et al. |
| 5,549,679 | A | 8/1996 | Kuslich |
| 5,554,191 | A | 9/1996 | Lahille et al. |
| 5,556,430 | A | 9/1996 | Gendler |
| 5,569,308 | A | 10/1996 | Sottosanti |
| 5,570,983 | A | 11/1996 | Hollander |
| 5,571,190 | A | 11/1996 | Ulrich et al. |
| 5,571,192 | A | 11/1996 | Schonhoffer |
| 5,578,034 | A | 11/1996 | Estes |
| 5,593,409 | A | 1/1997 | Michelson |
| 5,597,278 | A | 1/1997 | Peterkort |
| 5,601,553 | A | 2/1997 | Trebing et al. |
| 5,601,554 | A | 2/1997 | Howland et al. |
| 5,607,428 | A | 3/1997 | Lin |
| 5,607,474 | A | 3/1997 | Athanasiou et al. |
| 5,609,635 | A | 3/1997 | Michelson |
| 5,609,636 | A | 3/1997 | Kohrs et al. |
| 5,609,637 | A | 3/1997 | Biedermann et al. |
| 5,616,144 | A | 4/1997 | Yapp et al. |
| 5,642,960 | A | 7/1997 | Salice |
| 5,645,606 | A | 7/1997 | Oehy et al. |

(56) References Cited

U.S. PATENT DOCUMENTS

| | | |
|---|---|---|
| 5,653,708 A | 8/1997 | Howland |
| 5,676,666 A | 10/1997 | Oxland |
| 5,676,699 A | 10/1997 | Gogolewski et al. |
| 5,681,311 A | 10/1997 | Foley et al. |
| 5,683,216 A | 11/1997 | Erbes |
| 5,683,394 A | 11/1997 | Rinner |
| 5,683,463 A | 11/1997 | Godefroy et al. |
| 5,702,449 A | 12/1997 | McKay |
| 5,702,451 A | 12/1997 | Biedermann et al. |
| 5,702,453 A | 12/1997 | Rabbe et al. |
| 5,702,455 A | 12/1997 | Saggar |
| 5,713,899 A | 2/1998 | Marnay et al. |
| 5,713,900 A | 2/1998 | Benzel et al. |
| 5,725,588 A | 3/1998 | Errico et al. |
| 5,728,159 A | 3/1998 | Stroever et al. |
| 5,735,853 A | 4/1998 | Olerud |
| 5,735,905 A | 4/1998 | Parr |
| 5,755,796 A | 5/1998 | Ibo et al. |
| 5,766,253 A | 6/1998 | Brosnahan |
| 5,776,194 A | 7/1998 | Mikol et al. |
| 5,776,196 A | 7/1998 | Matsuzaki et al. |
| 5,776,197 A | 7/1998 | Rabbe et al. |
| 5,776,198 A | 7/1998 | Rabbe et al. |
| 5,776,199 A | 7/1998 | Michelson |
| 5,778,804 A | 7/1998 | Read |
| 5,782,915 A | 7/1998 | Stone |
| 5,785,710 A | 7/1998 | Michelson |
| 5,800,433 A | 9/1998 | Benzel et al. |
| 5,861,041 A | 1/1999 | Tienboon |
| 5,865,845 A | 2/1999 | Thalgott |
| 5,865,849 A | 2/1999 | Stone |
| 5,876,402 A | 3/1999 | Errico et al. |
| 5,876,452 A | 3/1999 | Athanasiou et al. |
| 5,879,389 A | 3/1999 | Koshino |
| 5,885,299 A | 3/1999 | Winslow et al. |
| 5,888,222 A | 3/1999 | Coates et al. |
| 5,888,223 A | 3/1999 | Bray |
| 5,888,224 A | 3/1999 | Beckers et al. |
| 5,888,227 A | 3/1999 | Cottle |
| 5,895,426 A | 4/1999 | Scarborough et al. |
| 5,899,939 A | 5/1999 | Boyce et al. |
| 5,902,303 A | 5/1999 | Eckhof et al. |
| 5,902,338 A | 5/1999 | Stone |
| 5,904,683 A | 5/1999 | Pohndorf et al. |
| 5,904,719 A | 5/1999 | Errico et al. |
| 5,910,315 A | 6/1999 | Stevenson et al. |
| 5,911,758 A | 6/1999 | Oehy et al. |
| 5,920,312 A | 7/1999 | Wagner et al. |
| 5,922,027 A | 7/1999 | Stone |
| 5,931,838 A | 8/1999 | Vito |
| 5,944,755 A | 8/1999 | Stone |
| 5,951,558 A | 9/1999 | Fiz |
| 5,954,722 A | 9/1999 | Bono |
| 5,958,314 A | 9/1999 | Draenet |
| 5,968,098 A | 10/1999 | Winslow |
| 5,972,368 A | 10/1999 | McKay |
| 5,976,141 A | 11/1999 | Haag et al. |
| 5,976,187 A | 11/1999 | Richelsoph |
| 5,980,522 A | 11/1999 | Koros et al. |
| 5,981,828 A | 11/1999 | Nelson et al. |
| 5,984,967 A | 11/1999 | Zdeblick et al. |
| 5,989,289 A | 11/1999 | Coates et al. |
| 6,013,853 A | 1/2000 | Athanasiou et al. |
| 6,017,345 A | 1/2000 | Richelsoph |
| 6,025,538 A | 2/2000 | Yaccarino et al. |
| 6,033,405 A | 3/2000 | Winslow et al. |
| 6,033,438 A | 3/2000 | Bianchi et al. |
| 6,039,762 A | 3/2000 | McKay |
| 6,045,579 A | 4/2000 | Hochshuler et al. |
| 6,045,580 A | 4/2000 | Scarborough et al. |
| 6,056,749 A | 5/2000 | Kuslich |
| 6,066,175 A | 5/2000 | Henderson et al. |
| 6,080,158 A | 6/2000 | Lin |
| 6,080,193 A | 6/2000 | Hochshuler et al. |
| 6,086,593 A | 7/2000 | Bonutti |
| 6,086,614 A | 7/2000 | Mumme |
| 6,090,998 A | 7/2000 | Grooms et al. |
| 6,096,080 A | 8/2000 | Nicholson et al. |
| 6,096,081 A | 8/2000 | Grivas et al. |
| 6,099,531 A | 8/2000 | Bonutti |
| 6,110,482 A | 8/2000 | Khouri et al. |
| 6,113,637 A | 9/2000 | Gill et al. |
| 6,113,638 A | 9/2000 | Williams et al. |
| 6,120,503 A | 9/2000 | Michelson |
| 6,123,731 A | 9/2000 | Boyce et al. |
| 6,129,763 A | 10/2000 | Chauvin et al. |
| 6,136,001 A | 10/2000 | Michelson |
| 6,139,550 A | 10/2000 | Michelson |
| 6,143,030 A | 11/2000 | Schroder |
| 6,143,033 A | 11/2000 | Paul et al. |
| 6,156,070 A | 12/2000 | Incavo et al. |
| 6,193,721 B1 | 2/2001 | Michelson |
| 6,193,756 B1 | 2/2001 | Studer et al. |
| 6,193,757 B1 | 2/2001 | Foley et al. |
| 6,200,347 B1 | 3/2001 | Anderson et al. |
| 6,206,922 B1 | 3/2001 | Zdeblick et al. |
| 6,224,602 B1 | 5/2001 | Hayes |
| 6,231,610 B1 | 5/2001 | Geisler |
| 6,235,033 B1 | 5/2001 | Brace et al. |
| 6,235,034 B1 | 5/2001 | Bray |
| 6,235,059 B1 | 5/2001 | Benezech et al. |
| 6,241,731 B1 | 6/2001 | Fiz |
| 6,241,769 B1 | 6/2001 | Nicholson et al. |
| 6,245,108 B1 | 6/2001 | Biscup |
| 6,258,089 B1 | 7/2001 | Campbell et al. |
| 6,258,125 B1 | 7/2001 | Paul et al. |
| 6,261,291 B1 | 7/2001 | Talaber et al. |
| 6,261,586 B1 | 7/2001 | McKay |
| 6,264,695 B1 | 7/2001 | Stoy |
| 6,270,528 B1 | 8/2001 | McKay |
| 6,306,139 B1 | 10/2001 | Fuentes |
| 6,322,562 B1 | 11/2001 | Wolter |
| 6,331,179 B1 | 12/2001 | Freid et al. |
| 6,342,074 B1 | 1/2002 | Simpson |
| 6,364,880 B1 | 4/2002 | Michelson |
| 6,371,986 B1 | 4/2002 | Bagby |
| 6,371,988 B1 | 4/2002 | Pafford et al. |
| 6,371,989 B1 | 4/2002 | Chauvin et al. |
| 6,375,681 B1 | 4/2002 | Truscott |
| 6,383,186 B1 | 5/2002 | Michelson |
| 6,387,130 B1 | 5/2002 | Stone et al. |
| 6,395,031 B1 | 5/2002 | Foley et al. |
| 6,398,811 B1 | 6/2002 | McKay |
| 6,413,259 B1 | 7/2002 | Lyons et al. |
| 6,423,063 B1 | 7/2002 | Bonutti |
| 6,432,106 B1 | 8/2002 | Fraser |
| 6,447,512 B1 | 9/2002 | Landry et al. |
| 6,447,546 B1 | 9/2002 | Bramlet et al. |
| 6,454,771 B1 | 9/2002 | Michelson |
| 6,458,158 B1 | 10/2002 | Anderson et al. |
| 6,461,359 B1 * | 10/2002 | Tribus et al. ............... 606/247 |
| 6,468,311 B2 | 10/2002 | Boyd et al. |
| 6,471,724 B2 | 10/2002 | Zdeblick et al. |
| 6,503,250 B2 | 1/2003 | Paul |
| 6,524,312 B2 | 2/2003 | Landry et al. |
| 6,558,387 B2 | 5/2003 | Errico et al. |
| 6,558,423 B1 | 5/2003 | Michelson |
| 6,558,424 B2 | 5/2003 | Thalgott |
| 6,562,073 B2 | 5/2003 | Foley |
| 6,569,201 B2 | 5/2003 | Moumene et al. |
| 6,575,975 B2 | 6/2003 | Brace et al. |
| 6,576,017 B2 | 6/2003 | Foley et al. |
| 6,579,290 B1 | 6/2003 | Hardcastle et al. |
| 6,592,624 B1 | 7/2003 | Fraser et al. |
| 6,602,291 B1 | 8/2003 | Ray et al. |
| 6,605,090 B1 | 8/2003 | Trieu et al. |
| 6,616,671 B2 | 9/2003 | Landry et al. |
| 6,620,163 B1 | 9/2003 | Michelson |
| 6,623,486 B1 | 9/2003 | Weaver et al. |
| 6,629,998 B1 | 10/2003 | Lin |
| 6,638,310 B2 | 10/2003 | Lin et al. |
| 6,645,212 B2 | 11/2003 | Goldhahn et al. |
| 6,652,525 B1 | 11/2003 | Assaker et al. |
| 6,656,181 B2 | 12/2003 | Dixon et al. |

(56) References Cited

U.S. PATENT DOCUMENTS

| | | |
|---|---|---|
| 6,679,887 B2 | 1/2004 | Nicholson et al. |
| 6,682,561 B2 | 1/2004 | Songer et al. |
| 6,682,563 B2 | 1/2004 | Scharf |
| 6,695,846 B2 | 2/2004 | Richelsoph et al. |
| 6,695,851 B2 | 2/2004 | Zdeblick et al. |
| 6,706,067 B2 | 3/2004 | Shimp et al. |
| 6,709,456 B2 | 3/2004 | Langberg et al. |
| 6,712,818 B1 | 3/2004 | Michelson |
| 6,730,127 B2 | 5/2004 | Michelson |
| 6,736,850 B2 | 5/2004 | Davis |
| 6,761,739 B2 | 7/2004 | Shepard |
| 6,770,096 B2 | 8/2004 | Bolger et al. |
| 6,786,909 B1 | 9/2004 | Dransfeld et al. |
| 6,800,092 B1 | 10/2004 | Williams et al. |
| 6,805,714 B2 | 10/2004 | Sutcliffe |
| 6,808,537 B2 | 10/2004 | Michelson |
| 6,824,564 B2 | 11/2004 | Crozet |
| 6,833,006 B2 | 12/2004 | Foley et al. |
| 6,837,905 B1 | 1/2005 | Lieberman |
| 6,849,093 B2 | 2/2005 | Michelson |
| 6,855,168 B2 | 2/2005 | Crozet |
| 6,863,673 B2 | 3/2005 | Gerbec et al. |
| 6,872,915 B2 | 3/2005 | Koga et al. |
| 6,884,242 B2 | 4/2005 | LeHuec et al. |
| 6,890,334 B2 | 5/2005 | Brace et al. |
| 6,896,701 B2 | 5/2005 | Boyd et al. |
| 6,899,735 B2 | 5/2005 | Coates et al. |
| 6,902,578 B1 | 6/2005 | Anderson et al. |
| 6,916,320 B2 | 7/2005 | Michelson |
| 6,923,756 B2 | 8/2005 | Sudakov et al. |
| 6,953,477 B2 | 10/2005 | Berry |
| 6,962,606 B2 | 11/2005 | Michelson |
| 6,964,664 B2 | 11/2005 | Freid et al. |
| 6,964,687 B1 | 11/2005 | Bernard et al. |
| 6,972,019 B2 | 12/2005 | Michelson |
| 6,972,035 B2 | 12/2005 | Michelson |
| 6,974,479 B2 | 12/2005 | Trieu |
| 6,984,234 B2 | 1/2006 | Bray |
| 7,001,385 B2 | 2/2006 | Bonutti |
| 7,001,432 B2 | 2/2006 | Keller et al. |
| 7,018,416 B2 | 3/2006 | Hanson et al. |
| 7,033,394 B2 | 4/2006 | Michelson |
| 7,041,135 B2 | 5/2006 | Michelson |
| 7,044,968 B1 | 5/2006 | Yaccarino et al. |
| 7,044,972 B2 | 5/2006 | Mathys et al. |
| 7,060,097 B2 | 6/2006 | Fraser et al. |
| 7,066,961 B2 | 6/2006 | Michelson |
| 7,077,864 B2 | 7/2006 | Byrd, III et al. |
| 7,112,222 B2 | 9/2006 | Fraser et al. |
| 7,112,223 B2 | 9/2006 | Davis |
| 7,135,024 B2 | 11/2006 | Cook et al. |
| 7,135,043 B2 | 11/2006 | Nakahara et al. |
| 7,137,984 B2 | 11/2006 | Michelson |
| 7,147,665 B1 | 12/2006 | Bryan et al. |
| 7,163,561 B2 | 1/2007 | Michelson |
| 7,172,627 B2 | 2/2007 | Fiere et al. |
| 7,172,672 B2 | 2/2007 | Silverbrook |
| 7,226,452 B2 | 6/2007 | Zubok |
| 7,226,482 B2 | 6/2007 | Messerli et al. |
| 7,232,463 B2 | 6/2007 | Falahee |
| 7,232,464 B2 | 6/2007 | Mathieu et al. |
| 7,238,203 B2 | 7/2007 | Bagga et al. |
| 7,255,698 B2 | 8/2007 | Michelson |
| 7,276,082 B2 | 10/2007 | Zdeblick et al. |
| 7,320,708 B1 | 1/2008 | Bernstein |
| 7,323,011 B2 | 1/2008 | Shepard et al. |
| 7,442,209 B2 | 10/2008 | Michelson |
| 7,491,237 B2 | 2/2009 | Randall et al. |
| 7,534,265 B1 | 5/2009 | Boyd et al. |
| 7,594,932 B2 | 9/2009 | Aferzon et al. |
| 7,601,173 B2 | 10/2009 | Messerli et al. |
| 7,608,107 B2 | 10/2009 | Michelson |
| 7,618,456 B2 | 11/2009 | Mathieu et al. |
| 7,621,960 B2 | 11/2009 | Boyd et al. |
| 7,625,380 B2 | 12/2009 | Drewry et al. |
| 7,637,951 B2 | 12/2009 | Michelson |
| 7,655,042 B2 | 2/2010 | Foley et al. |
| 7,704,279 B2 | 4/2010 | Moskowitz et al. |
| 7,846,188 B2 | 12/2010 | Moskowitz et al. |
| 7,846,207 B2 | 12/2010 | Lechmann et al. |
| 7,862,616 B2 | 1/2011 | Lechmann |
| 7,875,076 B2 | 1/2011 | Mathieu et al. |
| 7,942,903 B2 | 5/2011 | Moskowitz et al. |
| 7,993,403 B2 | 8/2011 | Foley et al. |
| 8,062,303 B2 | 11/2011 | Berry et al. |
| 8,128,700 B2 | 3/2012 | Delurio et al. |
| 8,182,532 B2 | 5/2012 | Anderson, et al. |
| 8,211,148 B2 | 7/2012 | Zhang et al. |
| 8,273,127 B2 | 9/2012 | Jones et al. |
| 8,308,804 B2 | 11/2012 | Kureger |
| 8,328,872 B2 | 12/2012 | Duffield et al. |
| 8,343,222 B2 | 1/2013 | Cope |
| 8,353,913 B2 | 1/2013 | Moskowitz et al. |
| 8,382,768 B2 | 2/2013 | Berry et al. |
| 8,425,607 B2 | 4/2013 | Waugh et al. |
| 8,465,546 B2 | 6/2013 | Jodaitis et al. |
| 8,540,774 B2 | 9/2013 | Kueenzi et al. |
| 8,545,567 B1 | 10/2013 | Kreuger |
| 8,641,743 B2 | 2/2014 | Michelson |
| 8,641,768 B2 | 2/2014 | Duffield et al. |
| 8,764,831 B2 | 7/2014 | Lechmann et al. |
| 9,005,295 B2 | 4/2015 | Kueenzi et al. |
| 2001/0001129 A1 | 5/2001 | McKay et al. |
| 2001/0005796 A1 | 6/2001 | Zdeblick et al. |
| 2001/0010021 A1 | 7/2001 | Boyd et al. |
| 2001/0016777 A1 | 8/2001 | Biscup |
| 2001/0020186 A1 | 9/2001 | Boyce et al. |
| 2001/0031254 A1 | 10/2001 | Bianchi et al. |
| 2001/0039456 A1 | 11/2001 | Boyer et al. |
| 2001/0041941 A1 | 11/2001 | Boyer et al. |
| 2002/0004683 A1 | 1/2002 | Michelson et al. |
| 2002/0010511 A1 | 1/2002 | Michelson |
| 2002/0016595 A1 | 2/2002 | Michelson |
| 2002/0022843 A1 | 2/2002 | Michelson |
| 2002/0029084 A1 | 3/2002 | Paul et al. |
| 2002/0065517 A1 | 5/2002 | Paul |
| 2002/0082597 A1 | 6/2002 | Fraser |
| 2002/0082603 A1 | 6/2002 | Dixon et al. |
| 2002/0091447 A1 | 7/2002 | Shimp et al. |
| 2002/0095155 A1 | 7/2002 | Michelson |
| 2002/0099376 A1 | 7/2002 | Michelson |
| 2002/0099378 A1 | 7/2002 | Michelson |
| 2002/0106393 A1 | 8/2002 | Bianchi et al. |
| 2002/0111680 A1 | 8/2002 | Michelson |
| 2002/0128712 A1 | 9/2002 | Michelson |
| 2002/0128717 A1 | 9/2002 | Alfaro et al. |
| 2002/0147450 A1 | 10/2002 | LeHuec et al. |
| 2002/0169508 A1 | 11/2002 | Songer et al. |
| 2002/0193880 A1 | 12/2002 | Fraser |
| 2003/0045939 A1 | 3/2003 | Casutt |
| 2003/0078668 A1 | 4/2003 | Michelson |
| 2003/0125739 A1 | 7/2003 | Bagga et al. |
| 2003/0135277 A1 | 7/2003 | Bryan et al. |
| 2003/0153975 A1 | 8/2003 | Byrd |
| 2003/0167092 A1 | 9/2003 | Foley |
| 2003/0195626 A1 | 10/2003 | Huppert |
| 2003/0195632 A1 | 10/2003 | Foley et al. |
| 2003/0199983 A1 | 10/2003 | Michelson |
| 2004/0078078 A1 | 4/2004 | Shepard |
| 2004/0078081 A1 | 4/2004 | Ferree |
| 2004/0092929 A1* | 5/2004 | Zindrick ............ 606/61 |
| 2004/0093084 A1 | 5/2004 | Michelson |
| 2004/0102848 A1 | 5/2004 | Michelson |
| 2004/0126407 A1 | 7/2004 | Falahee |
| 2004/0133278 A1 | 7/2004 | Marino et al. |
| 2004/0143270 A1 | 7/2004 | Zucherman et al. |
| 2004/0176853 A1 | 9/2004 | Sennett et al. |
| 2004/0199254 A1 | 10/2004 | Louis et al. |
| 2004/0210219 A1 | 10/2004 | Bray |
| 2004/0210310 A1 | 10/2004 | Trieu |
| 2004/0210314 A1 | 10/2004 | Michelson |
| 2004/0249377 A1 | 12/2004 | Kaes et al. |
| 2004/0254644 A1 | 12/2004 | Taylor |
| 2005/0015149 A1 | 1/2005 | Michelson |

(56) References Cited

U.S. PATENT DOCUMENTS

| | | |
|---|---|---|
| 2005/0021143 A1 | 1/2005 | Keller |
| 2005/0033433 A1 | 2/2005 | Michelson |
| 2005/0049593 A1 | 3/2005 | Duong et al. |
| 2005/0049595 A1 | 3/2005 | Suh et al. |
| 2005/0065605 A1 | 3/2005 | Jackson |
| 2005/0065607 A1 | 3/2005 | Gross |
| 2005/0065608 A1 | 3/2005 | Michelson |
| 2005/0071008 A1 | 3/2005 | Kirschman |
| 2005/0085913 A1 | 4/2005 | Fraser et al. |
| 2005/0101960 A1 | 5/2005 | Fiere et al. |
| 2005/0149193 A1 | 7/2005 | Zucherman et al. |
| 2005/0154391 A1 | 7/2005 | Doherty et al. |
| 2005/0159813 A1 | 7/2005 | Molz |
| 2005/0159818 A1 | 7/2005 | Blain |
| 2005/0159819 A1 | 7/2005 | McCormick et al. |
| 2005/0171607 A1 | 8/2005 | Michelson |
| 2005/0177236 A1 | 8/2005 | Mathieu et al. |
| 2005/0240267 A1 | 10/2005 | Randall et al. |
| 2005/0240271 A1 | 10/2005 | Zubock et al. |
| 2005/0261767 A1 | 11/2005 | Anderson et al. |
| 2006/0020342 A1 | 1/2006 | Ferree et al. |
| 2006/0030851 A1 | 2/2006 | Bray et al. |
| 2006/0079901 A1 | 4/2006 | Ryan et al. |
| 2006/0079961 A1 | 4/2006 | Michelson |
| 2006/0085071 A1 | 4/2006 | Lechmann et al. |
| 2006/0089717 A1 | 4/2006 | Krishna |
| 2006/0129240 A1 | 6/2006 | Lessar et al. |
| 2006/0136063 A1 | 6/2006 | Zeegers |
| 2006/0142765 A9 | 6/2006 | Dixon et al. |
| 2006/0195189 A1 | 8/2006 | Link et al. |
| 2006/0206208 A1 | 9/2006 | Michelson |
| 2006/0229725 A1 | 10/2006 | Lechmann et al. |
| 2007/0088441 A1 | 4/2007 | Duggal et al. |
| 2007/0093819 A1* | 4/2007 | Albert .................... 606/61 |
| 2007/0106384 A1 | 5/2007 | Bray et al. |
| 2007/0118125 A1 | 5/2007 | Orbay et al. |
| 2007/0123987 A1 | 5/2007 | Bernstein |
| 2007/0162130 A1 | 7/2007 | Rashbaum et al. |
| 2007/0168032 A1 | 7/2007 | Muhanna et al. |
| 2007/0219635 A1 | 9/2007 | Mathieu et al. |
| 2007/0225806 A1 | 9/2007 | Squires et al. |
| 2007/0225812 A1 | 9/2007 | Gill |
| 2007/0250167 A1 | 10/2007 | Bray et al. |
| 2007/0270961 A1 | 11/2007 | Ferguson |
| 2008/0033440 A1 | 2/2008 | Moskowitz et al. |
| 2008/0051890 A1 | 2/2008 | Waugh et al. |
| 2008/0082169 A1 | 4/2008 | Gittings |
| 2008/0119933 A1 | 5/2008 | Aebi et al. |
| 2008/0133013 A1 | 6/2008 | Duggal et al. |
| 2008/0161925 A1 | 7/2008 | Brittan et al. |
| 2008/0177307 A1 | 7/2008 | Moskowitz et al. |
| 2008/0200984 A1 | 8/2008 | Jodaitis et al. |
| 2008/0249569 A1 | 10/2008 | Waugh et al. |
| 2008/0249575 A1 | 10/2008 | Waugh et al. |
| 2008/0249625 A1 | 10/2008 | Waugh et al. |
| 2008/0269806 A1 | 10/2008 | Zhang et al. |
| 2008/0275455 A1 | 11/2008 | Berry et al. |
| 2008/0306596 A1 | 12/2008 | Jones et al. |
| 2009/0076608 A1 | 3/2009 | Gordon et al. |
| 2009/0105830 A1 | 4/2009 | Jones et al. |
| 2009/0192613 A1 | 7/2009 | Wing et al. |
| 2009/0210062 A1 | 8/2009 | Thalgott et al. |
| 2009/0210064 A1 | 8/2009 | Lechmann et al. |
| 2009/0234455 A1 | 9/2009 | Moskowitz et al. |
| 2009/0326580 A1* | 12/2009 | Anderson et al. ......... 606/246 |
| 2010/0016901 A1 | 1/2010 | Robinson |
| 2010/0125334 A1 | 5/2010 | Krueger |
| 2010/0145459 A1 | 6/2010 | McDonough et al. |
| 2010/0145460 A1 | 6/2010 | McDonough et al. |
| 2011/0118843 A1 | 5/2011 | Mathieu et al. |
| 2011/0295371 A1 | 12/2011 | Moskowitz et al. |
| 2012/0101581 A1 | 4/2012 | Mathieu et al. |
| 2012/0109309 A1 | 5/2012 | Mathieu et al. |
| 2012/0109310 A1 | 5/2012 | Mathieu et al. |
| 2012/0109311 A1 | 5/2012 | Mathieu et al. |
| 2012/0109312 A1 | 5/2012 | Mathieu et al. |
| 2012/0109313 A1 | 5/2012 | Mathieu et al. |
| 2012/0179259 A1 | 7/2012 | McDonough et al. |
| 2013/0073046 A1 | 3/2013 | Zaveloff et al. |
| 2013/0073047 A1 | 3/2013 | Laskowitz et al. |
| 2013/0166032 A1 | 6/2013 | McDonough et al. |
| 2013/0173013 A1 | 7/2013 | Anderson et al. |
| 2013/0268008 A1 | 10/2013 | McDonough et al. |
| 2014/0025168 A1 | 1/2014 | Klimek et al. |
| 2014/0121777 A1 | 5/2014 | Rosen et al. |
| 2014/0180422 A1 | 6/2014 | Klimek et al. |
| 2014/0257487 A1 | 9/2014 | Lawson et al. |
| 2014/0336770 A1 | 11/2014 | Petersheim et al. |
| 2014/0371859 A1 | 12/2014 | Petersheim et al. |

FOREIGN PATENT DOCUMENTS

| | | |
|---|---|---|
| CA | 2317791 A1 | 8/1999 |
| DE | 2821678 A | 11/1979 |
| DE | 3042003 A1 | 7/1982 |
| DE | 3933459 A1 | 4/1991 |
| DE | 4242889 A1 | 6/1994 |
| DE | 4409392 A1 | 9/1995 |
| DE | 4423257 | 1/1996 |
| DE | I9504867 C1 | 2/1996 |
| DE | 29913200 U1 | 9/1999 |
| DE | 20 2004 020209 | 5/2006 |
| DE | 202004020209 | 5/2006 |
| EP | 0179695 | 4/1986 |
| EP | 0505634 A1 | 9/1992 |
| EP | 0517030 A2 | 12/1992 |
| EP | 0517030 A3 | 4/1993 |
| EP | 0577178 A1 | 1/1994 |
| EP | 0639351 A2 | 2/1995 |
| EP | 0639351 A3 | 3/1995 |
| EP | 504346 B1 | 5/1995 |
| EP | 0517030 B1 | 9/1996 |
| EP | 0505634 B1 | 8/1997 |
| EP | 897697 A1 | 2/1999 |
| EP | 0966930 | 12/1999 |
| EP | 0968692 A1 | 1/2000 |
| EP | 0974319 A2 | 1/2000 |
| EP | 1033941 | 9/2000 |
| EP | 1051133 | 11/2000 |
| EP | 1103236 | 5/2001 |
| EP | 1402836 | 3/2004 |
| EP | 0906065 B1 | 9/2004 |
| EP | 1124512 | 9/2004 |
| EP | 1124512 B1 | 9/2004 |
| EP | 1459711 | 7/2007 |
| EP | 1459711 B1 | 7/2007 |
| EP | 1194087 | 8/2008 |
| FR | 2552659 | 4/1985 |
| FR | 2697996 | 5/1994 |
| FR | 2700947 | 8/1994 |
| FR | 2727003 | 5/1996 |
| FR | 2747034 A1 | 10/1997 |
| FR | 2753368 | 3/1998 |
| GB | 157668 A | 1/1921 |
| GB | 265592 A | 8/1927 |
| GB | 2148122 A | 5/1985 |
| GB | 2207607 | 2/1989 |
| GB | 2239482 A | 7/1991 |
| GB | 2266246 A | 10/1993 |
| JP | 03-505416 | 11/1991 |
| JP | 9-280219 | 10/1997 |
| JP | 2006-513752 | 4/2006 |
| RU | 2229271 | 5/2004 |
| RU | 2244527 | 1/2005 |
| RU | 2307625 | 10/2007 |
| SU | 1465040 A1 | 3/1989 |
| WO | WO 88/03417 | 5/1988 |
| WO | WO 88/10100 | 12/1988 |
| WO | WO 90/00037 | 1/1990 |
| WO | WO 92/01428 | 2/1992 |
| WO | WO 92/06005 | 4/1992 |
| WO | WO 95/21053 | 8/1995 |
| WO | WO 96/39988 | 12/1996 |
| WO | WO 97/20526 | 6/1997 |

(56) References Cited

FOREIGN PATENT DOCUMENTS

| | | |
|---|---|---|
| WO | WO 97/23175 A | 7/1997 |
| WO | WO 97/25941 | 7/1997 |
| WO | WO 97/25945 | 7/1997 |
| WO | WO 97/39693 | 10/1997 |
| WO | WO 98/17209 | 4/1998 |
| WO | WO 98/55052 | 12/1998 |
| WO | WO 98/56319 | 12/1998 |
| WO | WO 98/56433 | 12/1998 |
| WO | WO 99/09903 | 3/1999 |
| WO | WO 99/27864 | 6/1999 |
| WO | WO 99/29271 | 6/1999 |
| WO | WO 99/32055 | 7/1999 |
| WO | WO 99/38461 | 8/1999 |
| WO | WO 99/38463 A2 | 8/1999 |
| WO | WO 99/56675 | 11/1999 |
| WO | WO 99/63914 | 12/1999 |
| WO | WO 00/07527 | 2/2000 |
| WO | WO 00/07528 | 2/2000 |
| WO | WO 00/25706 | 5/2000 |
| WO | WO 00/30568 | 6/2000 |
| WO | WO 00/40177 | 7/2000 |
| WO | WO 00/41654 | 7/2000 |
| WO | WO 00/59412 | 10/2000 |
| WO | WO 00/66044 A1 | 11/2000 |
| WO | WO 00/66045 A1 | 11/2000 |
| WO | WO 00/74607 A1 | 12/2000 |
| WO | WO 01/08611 | 2/2001 |
| WO | WO 01/56497 A2 | 8/2001 |
| WO | WO 01/62190 | 8/2001 |
| WO | WO 01/80785 | 11/2001 |
| WO | WO 01/56497 A3 | 12/2001 |
| WO | WO 01/93742 A2 | 12/2001 |
| WO | WO 01/95837 A1 | 12/2001 |
| WO | WO 01/56497 B1 | 3/2002 |
| WO | WO 01/93742 A3 | 9/2002 |
| WO | WO 2004/069106 | 8/2004 |
| WO | WO 2005/007040 A | 1/2005 |
| WO | WO 2005/020861 | 3/2005 |
| WO | WO 2006/138500 | 12/2006 |
| WO | WO 2007/098288 | 8/2007 |
| WO | WO 2008/014258 | 1/2008 |
| WO | WO 2008/082473 | 7/2008 |
| WO | WO 2008/124355 | 10/2008 |
| WO | WO 2008/154326 | 12/2008 |
| WO | WO 2009/064644 | 5/2009 |
| WO | WO 2010/054181 | 5/2010 |
| WO | WO 2010/054208 | 5/2010 |
| WO | WO 2012/088238 | 6/2012 |

OTHER PUBLICATIONS

Appendix 1 to Joint Claim Construction Brief; Synthes' Exhibits A-9, In the United States District Court for the District of Delaware Civil Action No. 1:11-cv-00652-LPS, Jun. 8, 2012, 192 pages.

Appendix 2 to Joint Claim Construction Brief; Globus' Exhibits A-F, In the United States District Court for the District of Delaware Civil Action No. 1:11-cv-00652-LPS, Jun. 8, 2012, 146 pages.

*Appendix 3 to Joint Claim Construction Brief; Exhibits A-C*, In the United States District Court for the District of Delaware Civil Action No. 1:11-cv-00652-LPS, Jun. 8, 2012, 38 pages.

Chadwick et al., "Radiolucent Structural Materials for Medical Applications," www.mddionline.com/print/238, Jun. 1, 2001, accessed date Jul. 31, 2012, 9 pages.

Expert Report of Dr. Domagoj Carie Regarding the Invalidity of U.S. Pat. Nos. 7,846,207, 7,862,616 and 7,875,076, In the United States District Court for the District of Delaware, Civil Action No. 1:11-cv-00652-LPS, Nov. 5, 2012, 149 pages.

Expert Report of John F. Hall, M.D., United States District Court for the District of Delaware, Civil Action No. 1:11-cv-00652-LPS, Dec. 14, 2012, 27 pages.

Expert Report of Paul Ducheyne, Ph.D. Concerning Patent Validity, United States District Court District of Delaware, Civil Action No. 1:11-cv-00652-LPS, Dec. 13, 2012, 155 pages.

Expert Report of Richard J. Gering, Ph.D., CLP In the United States District Court for the District of Delaware, Civil Action No. 1:11-cv-00652-LPS, Dec. 14, 2012, 39 pages.

International Patent Application No. PCT/CH2003/00089, International Search Report dated Dec. 2, 2003, 3 pgs.

International Search Report, completed Aug. 16, 2007 for International Application No. PCT/US2007/005098, filed Feb. 27, 2007.

Joint Claim Construction Brief, In the United States District Court for the District of Delaware, Civil Action No. 1:11-cv-00652-LPS, Jun. 14, 2012, 97 pages.

Jonbergen et al., "Anterior CervicalLnterbody fusion with a titanium box cage: Early radiological assessment of fusion and subsidence", The Spine Journal 5, Jul. 2005, 645-649.

Jury Trial Demanded, In the United States District Court for the District of Delaware, Case No. 1:11-cv-00652-LPS, filed Jul. 22, 2011,8 pages.

Jury Verdict Form, United States District Court District of Delaware, Civil Action No. 1:11-cv-00652-LPS, Jun. 14, 2013, 20 pages.

Marcolongo et al., "Trends in Materials for Spine Surgery", Biomaterials and Clinical Use, 6, 2011, 21 pages.

Memorandum Opinion, United States District Court District of Delaware, Civil Action No. 1:11-cv-00652-LPS, May 7, 2013, 33 pages.

Order, United States District Court District of Delaware, Civil Action No. 1:11-cv-00652-LPS, May 15, 2013, 4 pages.

Order, United States District Court District of Delaware, Civil Action No. 1:11-cv-00652-LPS, May 7, 2013, 7 pages.

Parlov et al., "Anterior Lumbar Interbody Fusion with Threaded Fusion Cages and Autologous Grafts", Eur. Spine J., 2000, 9, 224-229.

Plaintiffs' Responses and Objections to Defendant Globus Medical, Inc.'s First Set of Interrogatories (Nos. 1-11), United States District Court for the District of Delaware, Civil Action No. 1:11-cv-00652-LPS, Nov. 14, 2011, 18 pages.

Plaintiffs' Supplemental Responses and Objections to Defendant Globus Medical Inc.'s Interrogatories Nos. 6-10 and Second Supplemental Responses and Objections to Interrogatory No. 5, United States District Court for the District of Delaware, Civil Action No. 11-cv-652-LPS, Sep. 1, 2012, 12 pages.

Redacted version of "Defendant Globus Medical, Inc.'s Answering Brief in Opposition to Plaintiff's Motion for Summary Judgment of No Anticipation by the Kozak and Michelson References", Mar. 12, 2013, 233 pages.

Redacted version of "Opening Brief in Support of Plaintiffs' Motion for Summary Judgment of No Anticipation by the Kozak and Michelson References", United States District Court District of Delaware, Civil Action No. 1:11-cv-00652-LPS, Feb. 13, 2013, 66 pages.

Redacted version of "Plaintiff's Reply Brief in Support of Plaintiff's Motion for Summary Judgment of No Anticipation by the Kozak and Michelson References", Mar. 21, 2013, 11 pages.

Reply Report of Dr. Domagoj Carie Regarding the Invalidity of U.S. Pat. Nos. 7,846,207, 7,862,616 and 7,875,076, In the United States District Court for the District of Delaware, Civil Action No. 1:11-cv-00652-LPS, Jan. 4, 2013, 81 pages.

Schleicher et al., "Biomechanical Comparison of Two Different Concepts for Stand-alone anterior lumbar interbody fusion", Eur. Spine J., Sep. 2008, 17, 1757-1765.

Scholz et al., "A New Stand-Alone Cervical Anterior Interbody Fusion Device", Spine, Jan. 2009, 34(2), 6 pages.

Second Expert Report of Wilson C. Hayes, Ph.D., United States District Court for the District of Delaware, Civil Action No. 1:11-cv-00652-LPS, Dec. 14, 2012, 22 pages.

Spruit et al., "The in Vitro Stabilizing Effect of Polyether-etherketone Cages Versus a Titanium Cage of similar design for anterior lumbar interbody fusion", Eur. Spine J., Aug. 2005, 14 752-758.

Trial Transcript, United States District Court District of Delaware, Civil Action No. 1:11-cv-00652-LPS, Jun. 10, 2013, 114 pages.

Trial Transcript, United States District Court District of Delaware, Civil Action No. 1:11-cv-00652-LPS, Jun. 11, 2013, 98 pages.

Trial Transcript, United States District Court District of Delaware, Civil Action No. 1:11-cv-00652-LPS, Jun. 12, 2013, 75 pages.

Trial Transcript, United States District Court District of Delaware, Civil Action No. 1:11-cv-00652-LPS, Jun. 13, 2013, 94 pages.

(56) References Cited

OTHER PUBLICATIONS

Trial Transcript, United States District Court District of Delaware, Civil Action No. 1:11-cv-00652-LPS, Jun. 14, 2013, 26 pages.
Trial Transcript, United States District Court District of Delaware, Civil Action No. 1:11-cv-00652-LPS, Jun. 3, 2013, 98 pages.
Trial Transcript, United States District Court District of Delaware, Civil Action No. 1:11-cv-00652-LPS, Jun. 4, 2013, 110 pages.
Trial Transcript, United States District Court District of Delaware, Civil Action No. 1:11-cv-00652-LPS, Jun. 5, 2013, 99 pages.
Trial Transcript, United States District Court District of Delaware, Civil Action No. 1:11-cv-00652-LPS, Jun. 6, 2013, 80 pages.
Trial Transcript, United States District Court District of Delaware, Civil Action No. 1:11-cv-00652-LPS, Jun. 7, 2013, 97 pages.
U.S. Appl. No. 11/199,599: Amendment/Request for Reconsideration after Non-Final Rejection, dated Sep. 29, 2009, 30 pages.
U.S. Appl. No. 11/199,599: Appeal Brief, dated Apr. 15, 2010, 51 pages.
U.S. Appl. No. 11/199,599: Final Rejection, dated Dec. 24, 2009, 21 pages.
U.S. Appl. No. 11/199,599: Interview Summary included Draft Amendments, dated Sep. 24, 2009, 16 pages.
U.S. Appl. No. 11/199,599: Non-Final Rejection, dated Apr. 1, 2009, 20 pages.
U.S. Appl. No. 11/199,599: Preliminary Amendment, dated Jan. 9, 2008, 11 pages.
Japanese Patent Application No. 2011-534926: Office Action dated Oct. 30, 2013, 7 pages.
Japanese Patent Application No. 2011-534928: Office Action dated Sep. 30, 2013, 11 pages.
Russian Patent Application No. 2011-1122797: Decision to Grant dated Oct. 9, 2013, 20 pages.
U.S. Appl. No. 60/988,661, filed Nov. 16, 2007, Kueenzi et al.
U.S. Appl. No. 61/535,726, filed Sep. 16, 2011, Zaveloff.
Synthes Spine, "SynFix-LR System. Instruments and Implants for Stand-Alone Anterior Lumbar Interbody Fusion (ALIF)", Technique Guide dated 2008, pp. 2-40, Published by Synthes Spine (USA).
Synthes Spine, "Zero-P Instruments and Implants. Zero-Profile Anterior Cervical Interbody Fusion (ACIF) device", Technique Guide dated 2008, pp. 2-32, Published by Synthes Spine (USA).
Bray, "InterPlate Spine Fusion Device: Subsidence Control Without Stress Shielding", Orthopaedic Product News, Sep./Oct. 2006, pp. 22-25.
International Search Report, Mailed Mar. 20, 2009, for PCT International Application No. PCT/US80/82473, filed Nov. 5, 2008.
Written Opinion, Mailed Mar. 20, 2009, for PCT International Application No. PCT/US08/82473, filed Nov. 5, 2008.
Synthes Spine, "CorticoCancellous ACF Spacer. An allograft space or anterior fusion of the cervical spine," brochure, Musculoskeletal Transplant Foundationm, 2003, 6 pages.
International Patent Application PCT/US2011/066421, International Search Report dated Jun. 14, 2012, 31 pages.

* cited by examiner

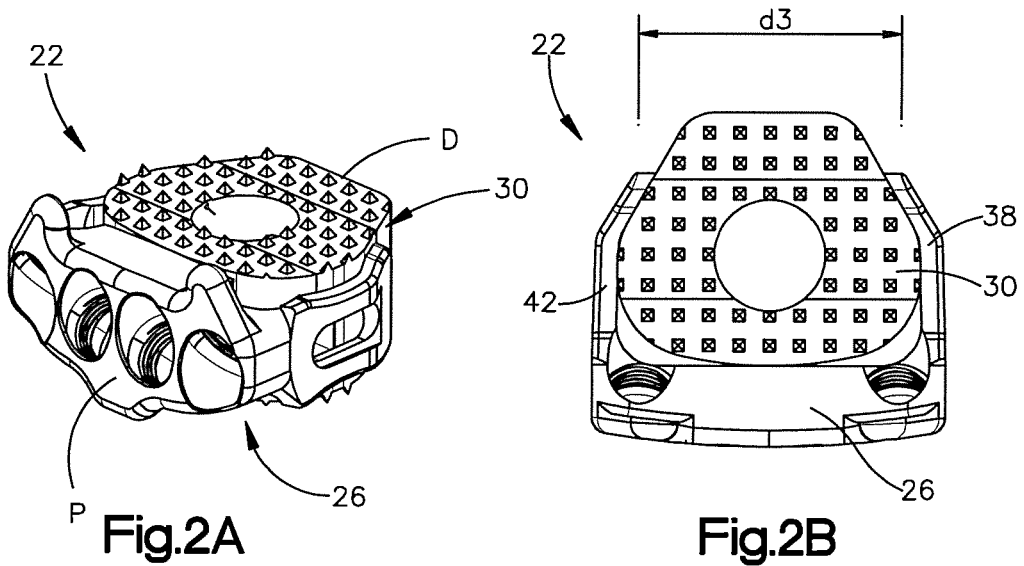
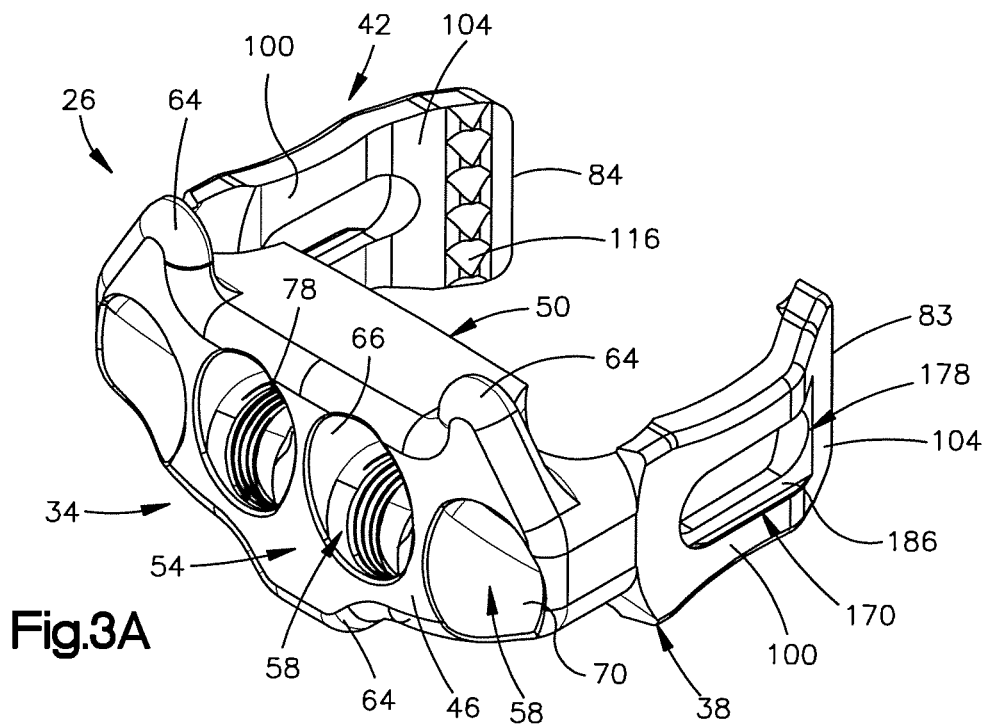

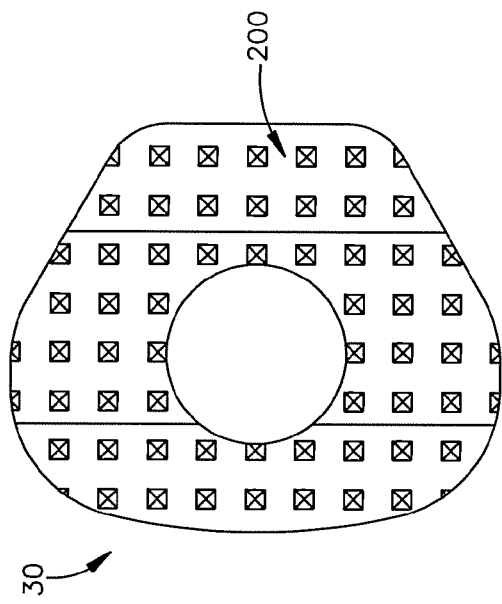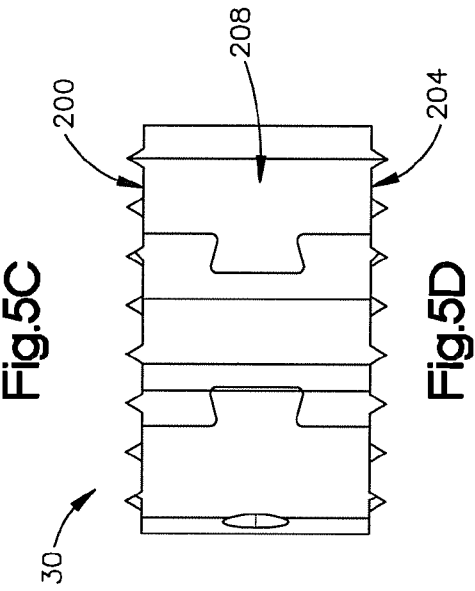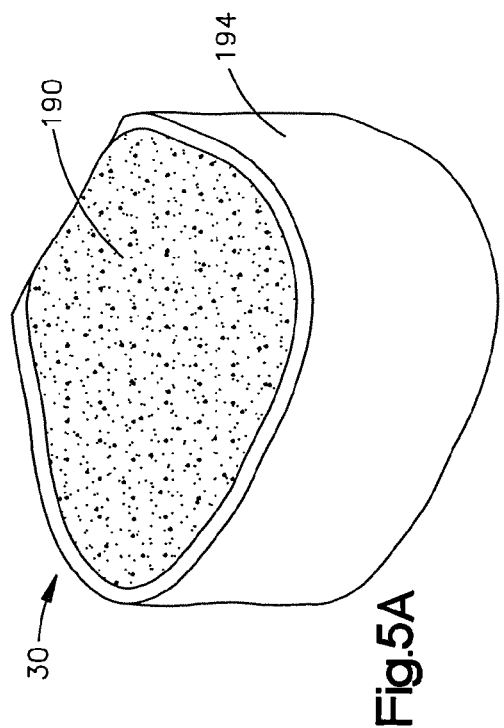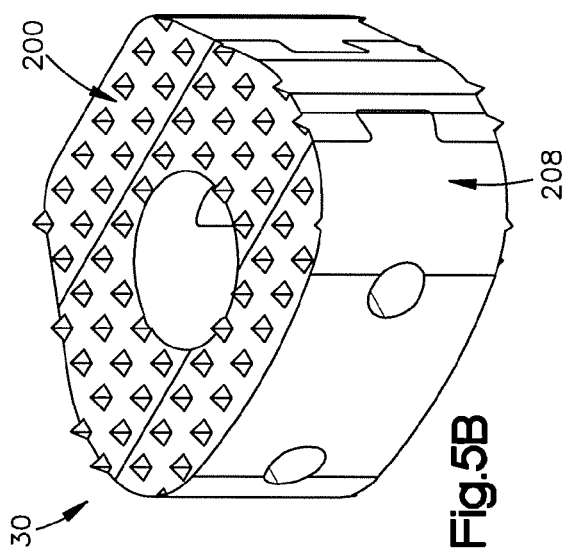

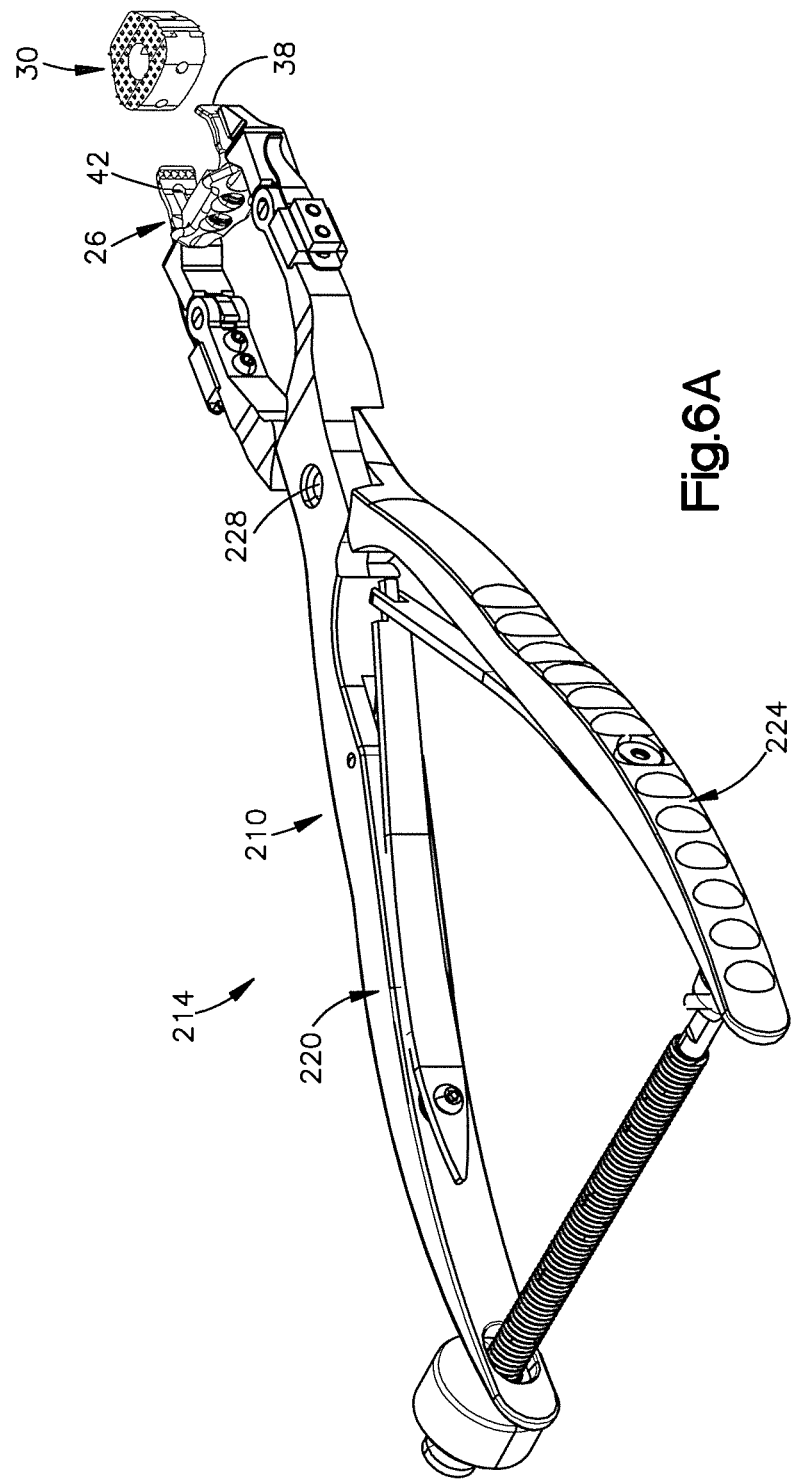

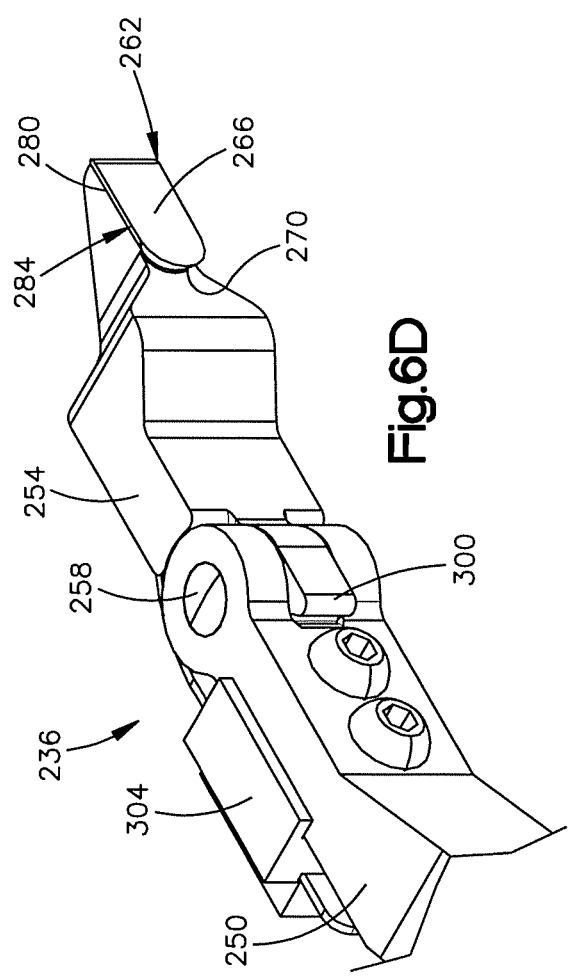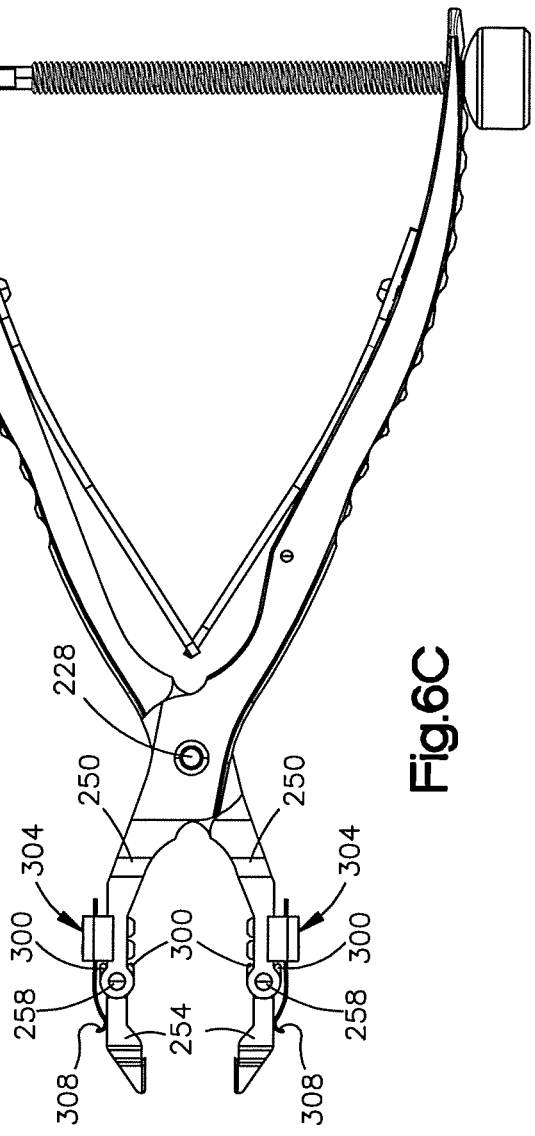

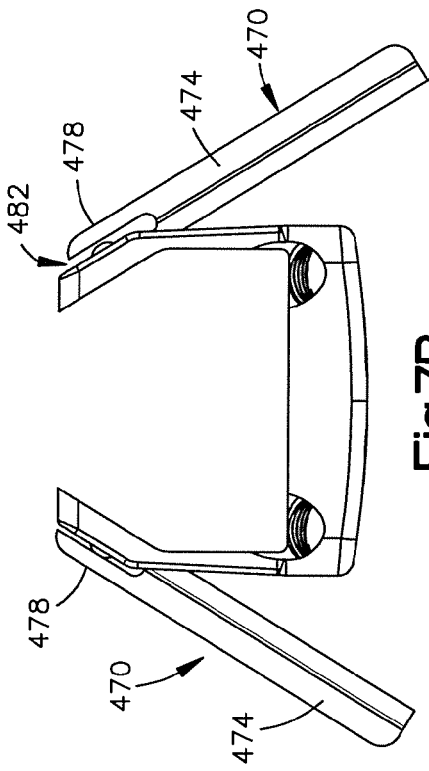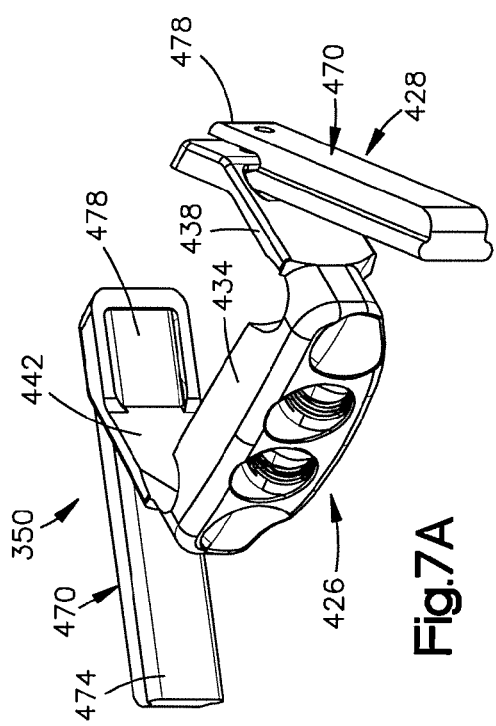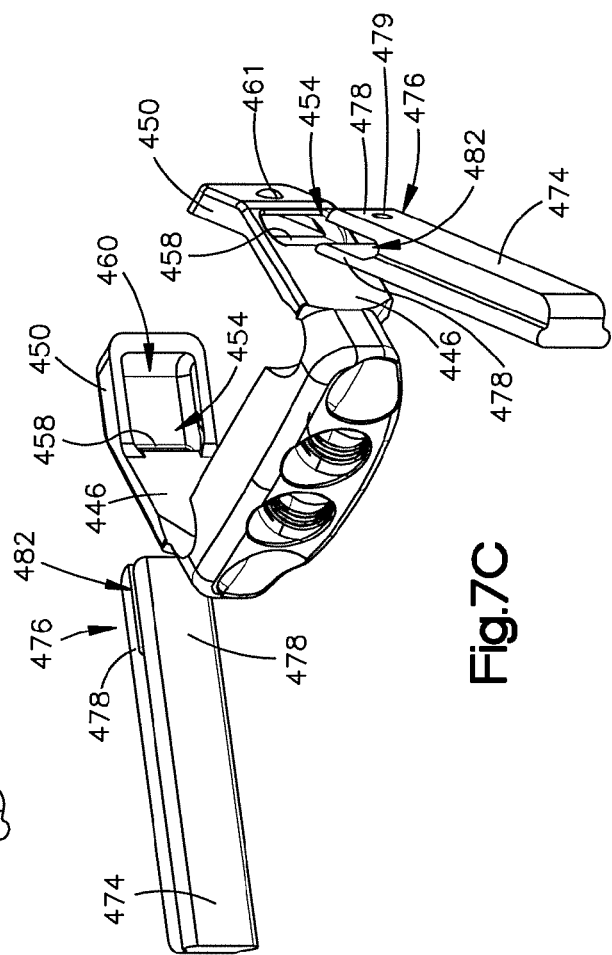

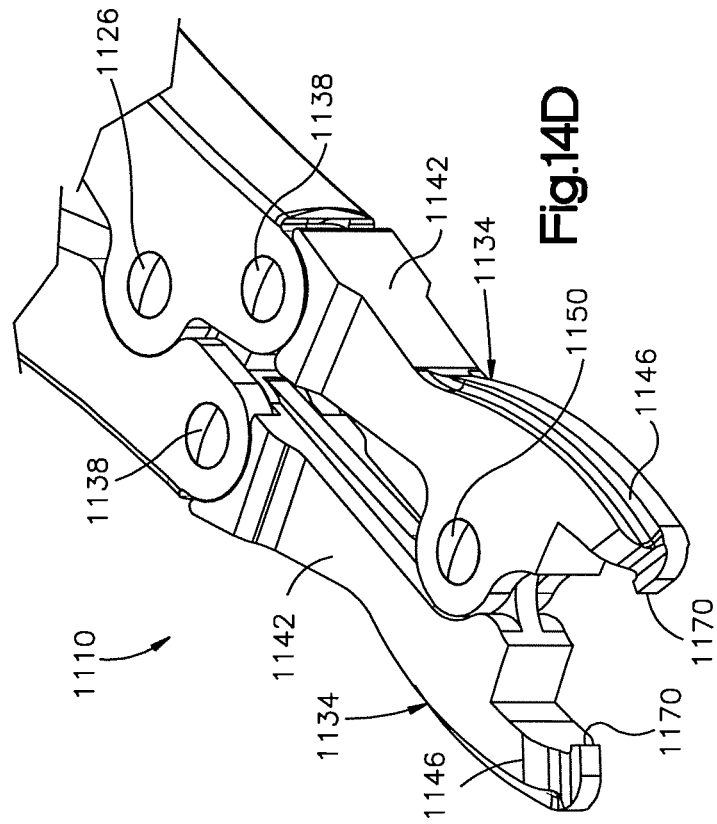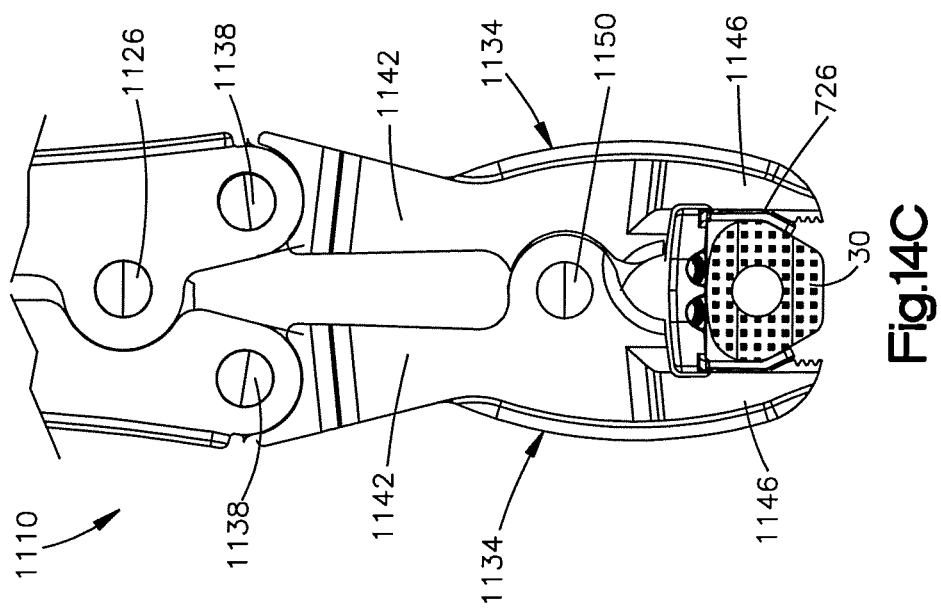

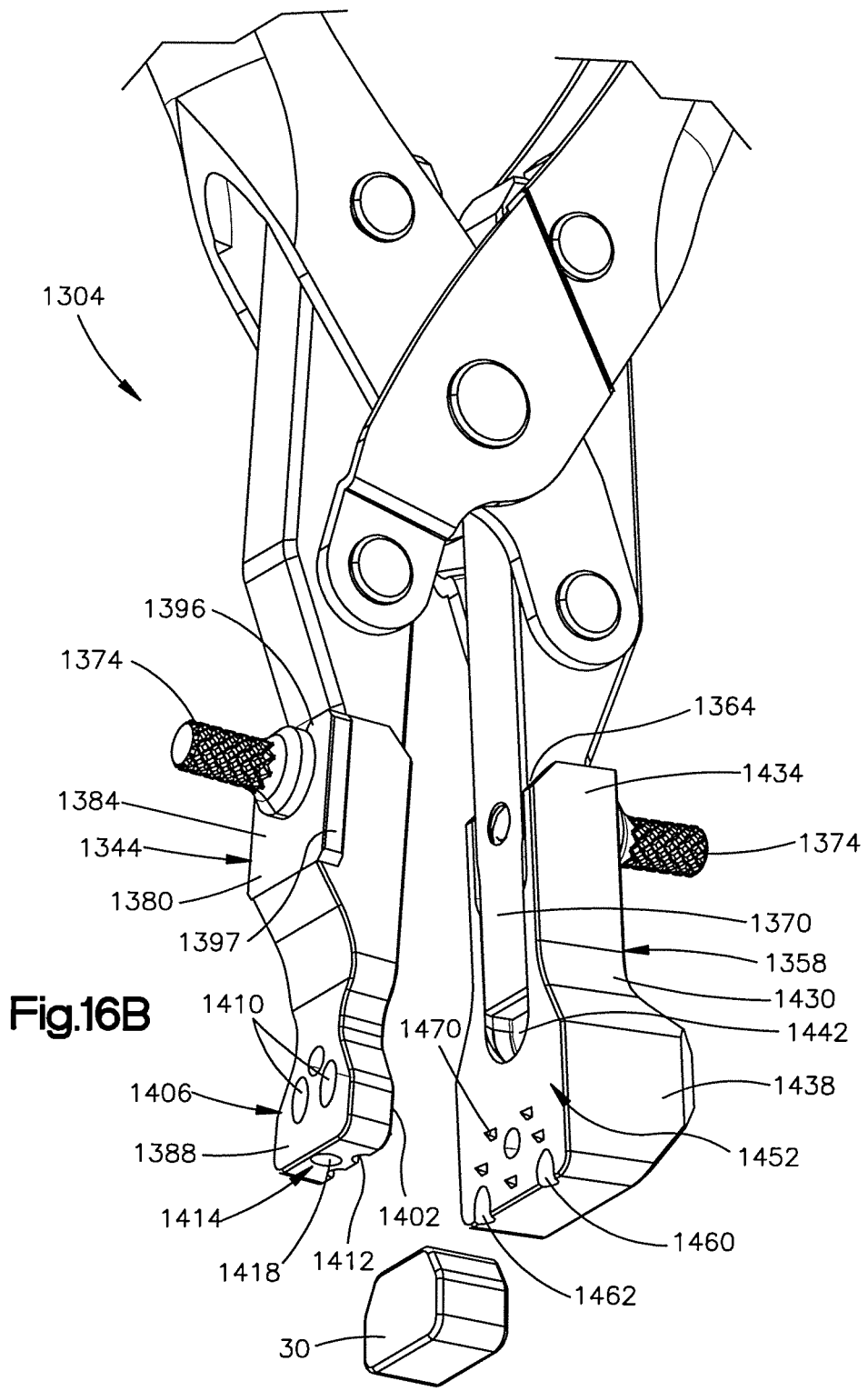

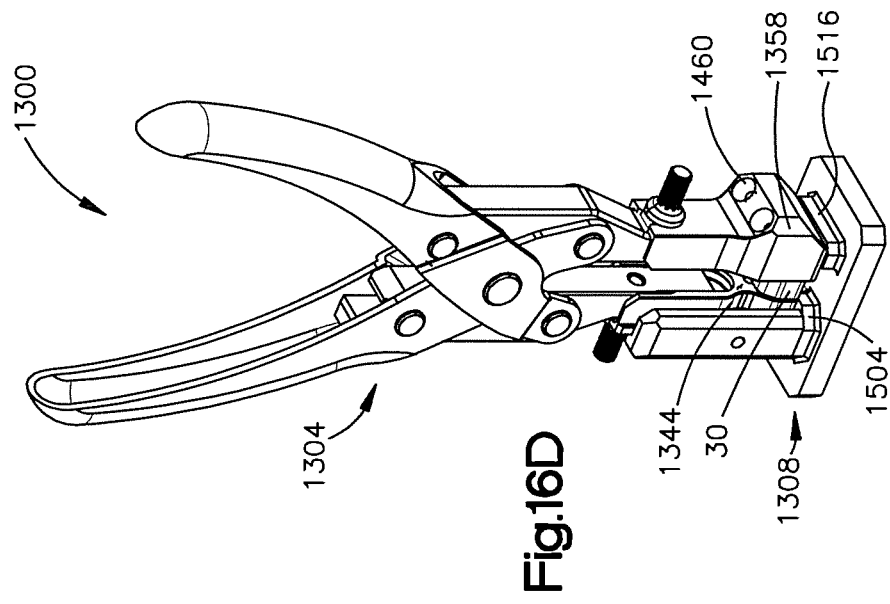
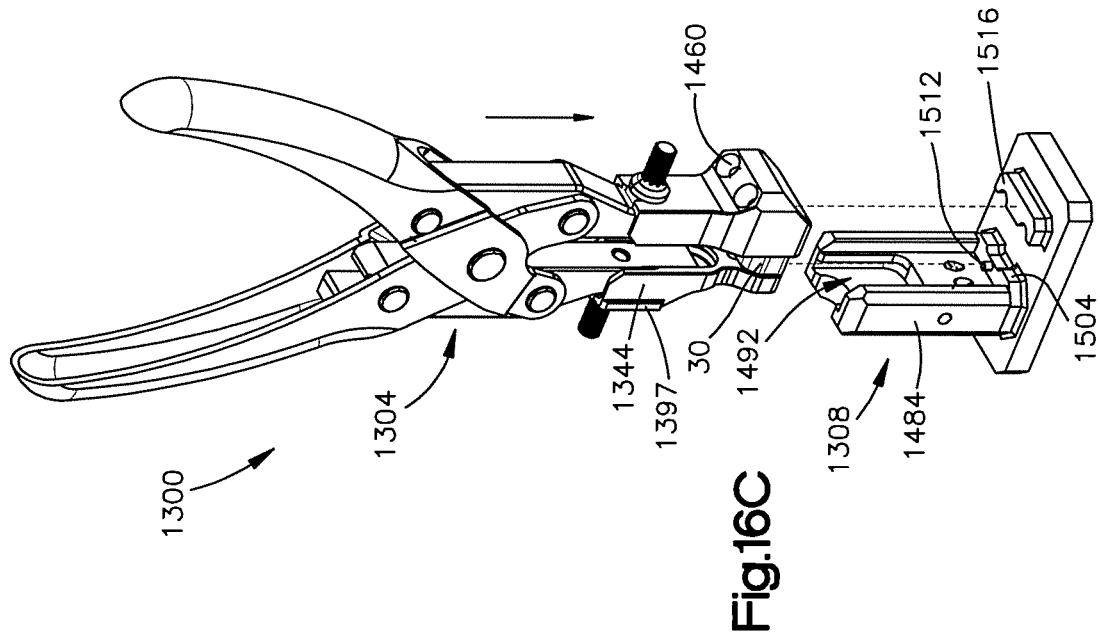

INTERVERTEBRAL IMPLANTS, SYSTEMS, AND METHODS OF USE

CROSS REFERENCE TO RELATED APPLICATIONS

This application is a continuation-in-part of U.S. patent application Ser. No. 13/333,065 filed Dec. 21, 2011, which claims the benefit of U.S. Provisional Patent Application Ser. No. 61/425,505 filed Dec. 21, 2010 and U.S. Provisional Patent Application Ser. No. 61/425,509 filed Dec. 21, 2010, the contents of each of which are hereby incorporated by reference in their entirety herein.

BACKGROUND

Implants for spinal fusion typically include a spacer body to allow for growth of bone between adjacent vertebral bodies while restoring and maintaining intervertebral space height that is defined between the vertebral bodies. In some cases, a plate is used to provide stability during healing so as to allow the patient to quickly resume an active lifestyle. The profile of the plate, which is placed on the anterior aspect of the vertebral bodies, however, can lead to dysphasia or patient discomfort which has resulted in various "zero-profile" devices currently being developed. For example, one zero profile device is an intervertebral device that is inserted into the intervertebral space. While the threaded device provides graft retention, stability in flexion and extension is questionable since the device does not positively lock to the vertebral bodies during implantation.

Other intervertebral implants have been utilized that include a frame shaped in a manner so as to hold a spacer body made from PEEK. Such spacer bodies typically are customized to have complimentary features to the frame so that the spacer bodies may be affixed to the frame. Such frames may not be desirable for spacer bodies made from allograft, however, because allograft spacer bodies may vary in shape, may not include the complimentary features needed to be affixed to the frame, and may degrade or resorb overtime.

SUMMARY

In accordance with an embodiment, an intervertebral implant frame can be configured to support a spacer body in an intervertebral space that is defined by a first vertebral body and a second vertebral body. The intervertebral implant frame can include a support member having a body that defines first and second vertebral body facing surfaces, the second vertebral body facing surface spaced from the first vertebral body facing surface along a first direction. The body can further define at least two fixation element receiving apertures that extend through the support member and are each configured to receive a respective bone fixation element. The implant frame can further include a first tab and a second tab that each extend from the first vertebral body facing surface and are spaced from each other along a second direction that is substantially perpendicular to the first direction so as to define a gap that extends between the first and second tabs along the second direction, each of the first and second tabs being configured to abut the first vertebral body when the intervertebral implant is inserted in the intervertebral space. The frame can further include first and second arms arm that extend from the support member and include, respectively, a first inner spacer contacting surface and a second inner spacer contacting surface that is spaced from the first inner spacer contacting surface along the second direction such that the first arm and the second arm are configured to grip and retain the spacer body. The gap can be configured to receive a portion of the first vertebral body when each of the first and second tabs abuts the first vertebral body.

BRIEF DESCRIPTION OF THE DRAWINGS

The foregoing summary, as well as the following detailed description of embodiments of the application, will be better understood when read in conjunction with the appended drawings. For the purposes of illustrating the methods, implants and systems of the present application, there is shown in the drawings preferred embodiments. It should be understood, however, that the application is not limited to the precise methods, implants, and systems shown. In the drawings:

FIG. 2A is a perspective view of the intervertebral implant illustrated in FIGS. 1A and 1B, the intervertebral implant having an intervertebral implant frame and a spacer body retained by the intervertebral implant frame;

FIG. 2B is a top plan view of the intervertebral implant shown in FIG. 2A;

FIG. 3A is a perspective view of the intervertebral implant frame shown in FIG. 2, the intervertebral implant frame having a support member, a first arm extending from the support member, and a second arm extending from the support member, the first and second arms configured to elastically flex away from each other;

FIG. 5A is a perspective view of a spacer body made from bone graft;

FIG. 5B is a perspective view of the spacer body shown in FIG. 2;

FIG. 5C is a top plan view of the spacer body shown in FIG. 5B;

FIG. 5D is a side elevation view of the spacer body shown in FIG. 5B;

FIG. 6A is a perspective view of an intervertebral implant system constructed in accordance with an embodiment, the system including an actuation instrument configured as an expansion instrument that includes an actuation grip illustrated as an expansion grip that is configured to actuate the frame shown in FIG. 3A from a first configuration to a second configuration whereby the frame is configured to receive the spacer body shown in FIG. 5B;

FIG. 6C is a top plan view of the expansion instrument shown in FIG. 6B;

FIG. 6D is a detailed view of one of the gripping portions of the expansion instrument shown in FIG. 6B;

FIG. 7A is a perspective view of an intervertebral implant system constructed in accordance with another embodiment, the system including a intervertebral implant frame, and an actuation instrument configured as an expansion instrument that comprises a pair of clips that engage first and second arms of the frame along a direction that is similar to an insertion direction of the frame;

FIG. 7B is a top plan view of the intervertebral implant system shown in FIG. 7A;

FIG. 7C is an exploded view of the intervertebral implant system shown in FIG. 7A;

FIG. 14C is a top plan view of the gripping members illustrated in FIG. 14B, shown in a crimped position, whereby the crimp members are crimped onto a spacer body of the intervertebral implant so as to secure the arms to the intervertebral implant;

FIG. 14D is a detailed view of gripping members of a crimping instrument constructed in accordance with another embodiment, the gripping members including a beaked protrusion configured to crimp the crimp members of the frame shown in FIG. 12A;

FIG. 16B is a perspective view of the clamp shown in FIG. 16A;

FIG. 16C is a perspective view of the clamp being mounted to the cradle;

FIG. 16D is a perspective view of the clamp after it has been mounted to the cradle;

DETAILED DESCRIPTION

Figure 1A:
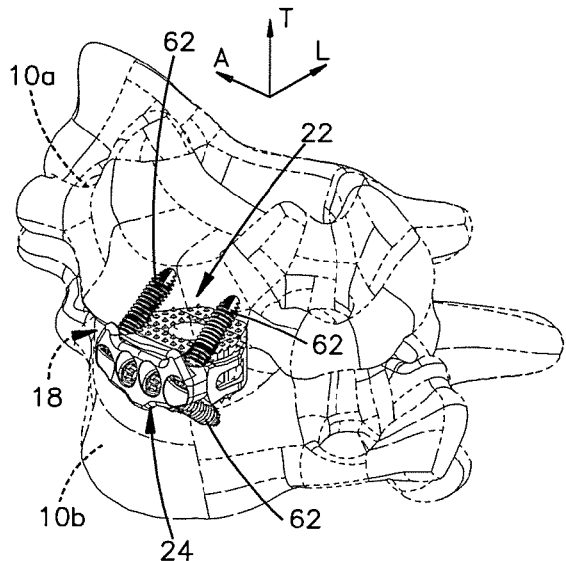
FIG. 1A is a perspective view of an intervertebral implant assembly that is implanted in an intervertebral space defined by a superior vertebral body and an inferior vertebral body, the intervertebral implant assembly including an intervertebral implant and at least a pair of fixation elements that attach the intervertebral implant to the superior vertebral body and the inferior vertebral body, respectively.
Figure 1B:
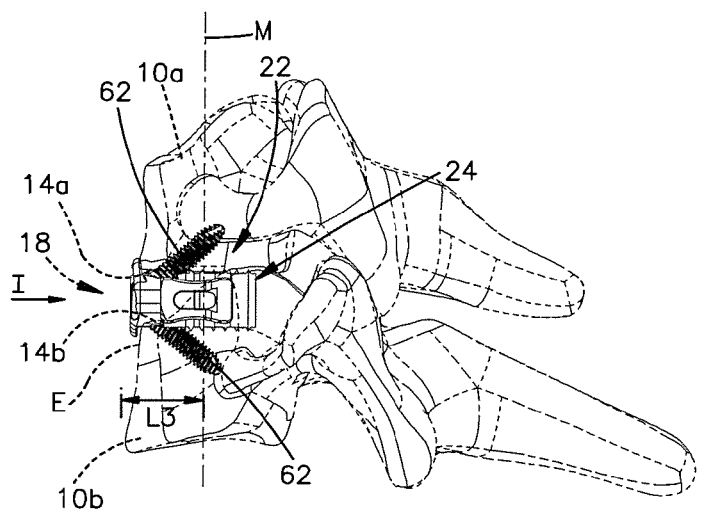
FIG. 1B is a side elevation view of the intervertebral implant assembly as shown in FIG. 1A, the intervertebral space defining an anterior-posterior midline.

Referring to FIGS. 1A and 1B, a superior vertebral body 10a defines a first or superior vertebral surface 14a of an intervertebral space 18, and an adjacent second or inferior vertebral body 10b defines an inferior vertebral surface 14b of the intervertebral space 18. Thus, the intervertebral space 18 is disposed between or otherwise defined by the vertebral bodies 10a and 10b. The vertebral bodies 10a and 10b can be anatomically adjacent vertebral bodies, or can remain after a portion of bone has been removed. The intervertebral space 18 can be disposed anywhere along the spine as desired, including at the lumbar, thoracic, and cervical regions of the spine. As illustrated, the intervertebral space 18 is illustrated after a discectomy, whereby the disc material has been removed or at least partially removed to prepare the intervertebral space 18 to receive an intervertebral implant 22 that can achieve height restoration. As shown, the intervertebral implant 22 can be affixed to the superior and inferior vertebral bodies 10a and 10b with respective fixation elements 62. The intervertebral implant 22 and the fixation elements 62 together define an intervertebral implant assembly 24.

Certain terminology is used in the following description for convenience only and is not limiting. The words "right", "left", "lower" and "upper" designate directions in the drawings to which reference is made. The words "inner" or "distal" and "outer" or "proximal" refer to directions toward and away from, respectively, the geometric center of the implant and related parts thereof. The words, "anterior", "posterior", "superior," "inferior," "medial," "lateral," and related words and/or phrases are used to designate various positions and orientations in the human body to which reference is made and are not meant to be limiting. The terminology includes the above-listed words, derivatives thereof and words of similar import.

The intervertebral implant 22 is described herein as extending horizontally along a longitudinal direction "L" and lateral direction "A", and vertically along a transverse direction "T". Unless otherwise specified herein, the terms "lateral," "longitudinal," and "transverse" are used to describe the orthogonal directional components of various components. It should be appreciated that while the longitudinal and lateral directions are illustrated as extending along a horizontal plane, and that the transverse direction is illustrated as extending along a vertical plane, the planes that encompass the various directions may differ during use. For instance, when the intervertebral implant 22 is implanted into the intervertebral space 18 along an insertion direction I, the transverse direction T extends vertically generally along the superior-inferior (or caudal-cranial) direction, while the horizontal plane defined by the longitudinal direction L and lateral direction A lies generally in the anatomical plane defined by the anterior-posterior direction, and the medial-lateral direction, respectively. Accordingly, the directional terms "vertical" and "horizontal" are used to describe the intervertebral implant 22 and its components as illustrated merely for the purposes of clarity and illustration.

Figure 1C:
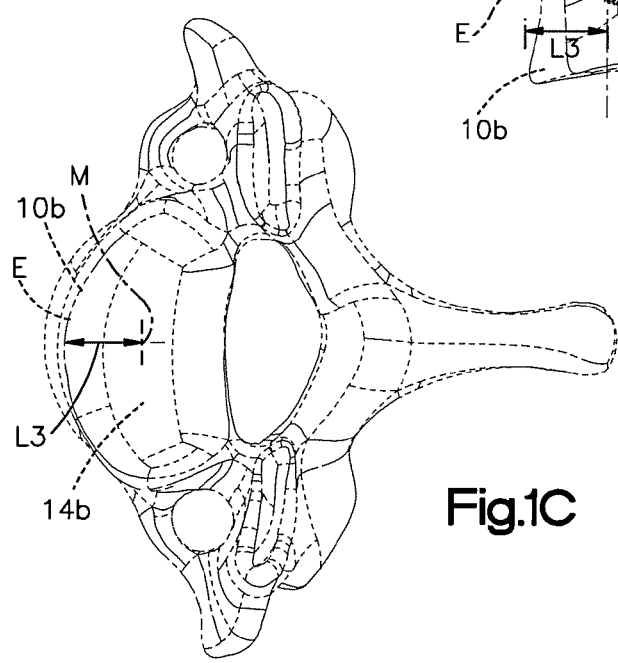
FIG. 1C is a top plan view of the inferior vertebral body shown in FIG. 1B.

As shown in FIGS. 1B and 1C, the vertebral surfaces 14a and 14b of the vertebral bodies 10a and 10b can define a geometrical centroid M that is generally located at an anterior-posterior midpoint between an anterior end and a posterior end of the surfaces 14a and 14b. As shown in FIG. 1B, the intervertebral implant 22 is configured to be disposed or otherwise implanted in the intervertebral space 18 such that a portion of the intervertebral implant 22 is located on a posterior side of a medial lateral plane that intersects the centroid M, and a portion of the intervertebral implant 22 is located on an anterior side of the medial lateral plane that intersects the centroid M. Such a configuration can ensure that the height restoration of the intervertebral space 18 remains relatively unchanged over time.

In reference to FIGS. 1A, 1B, 2A and 2B, the intervertebral implant 22 includes an intervertebral implant frame 26 and a spacer body 30 that is retained by the frame 26. The intervertebral implant 22, defines a proximal end P and a distal end D. The frame 26 may be made from any biocompatible material, such as TAN alloy, or PEEK. The spacer body 30 may be composed of a synthetic material such as PEEK or a graft substitute such a tricalcium phosphate or hydroxyapatite. The spacer body 30 may also be composed of a bone graft such as allograft bone, autograft bone or xenograft bone. By using a spacer body 30 composed of bone graft, surface area for fusion can be maximized. Additionally, incorporation of a bone graft spacer body 30 promotes bony on-growth and increased probability and speed of sound fusion. The frame 26 is configured to be attached to various bone graft spacer body footprint geometries, which may or may not conform to the internal footprint of the frame 26.

As shown in FIGS. 3A-3E the frame 26 includes a support member 34, a first arm 38 that extends from the support member 34, and a second arm 42 that extends from the support member 34. In the illustrated embodiment, the first and second arms 38 and 42 are flexible arms that extend from opposed ends of the support member 34 such that the support member 34, the first arm 38, and the second arm 42 together create a three wall structure that retains and secures the spacer body 30 to the frame 26.

Figure 3B:
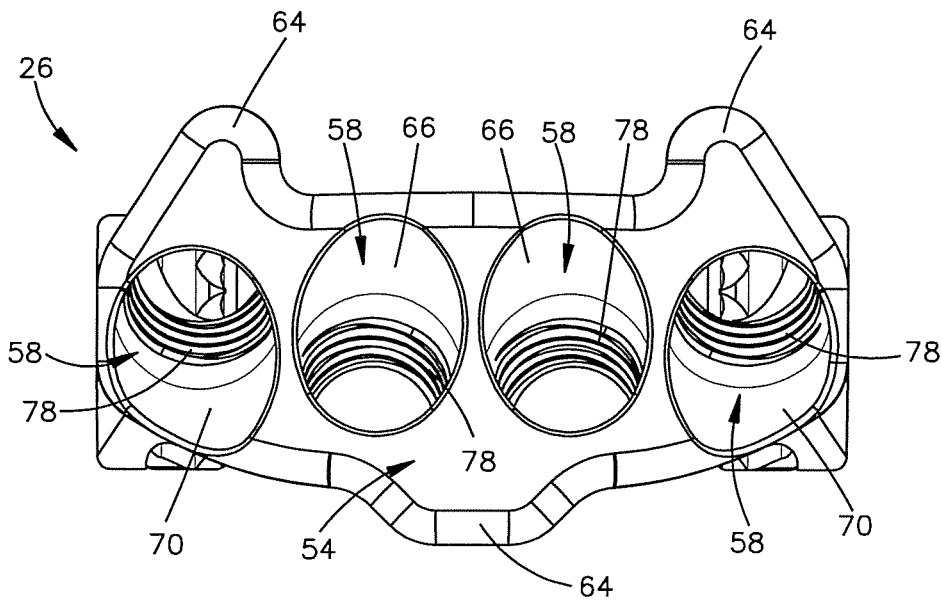
FIG. 3B is a front elevation view of the intervertebral implant frame shown in FIG. 3A.
Figure 3C:
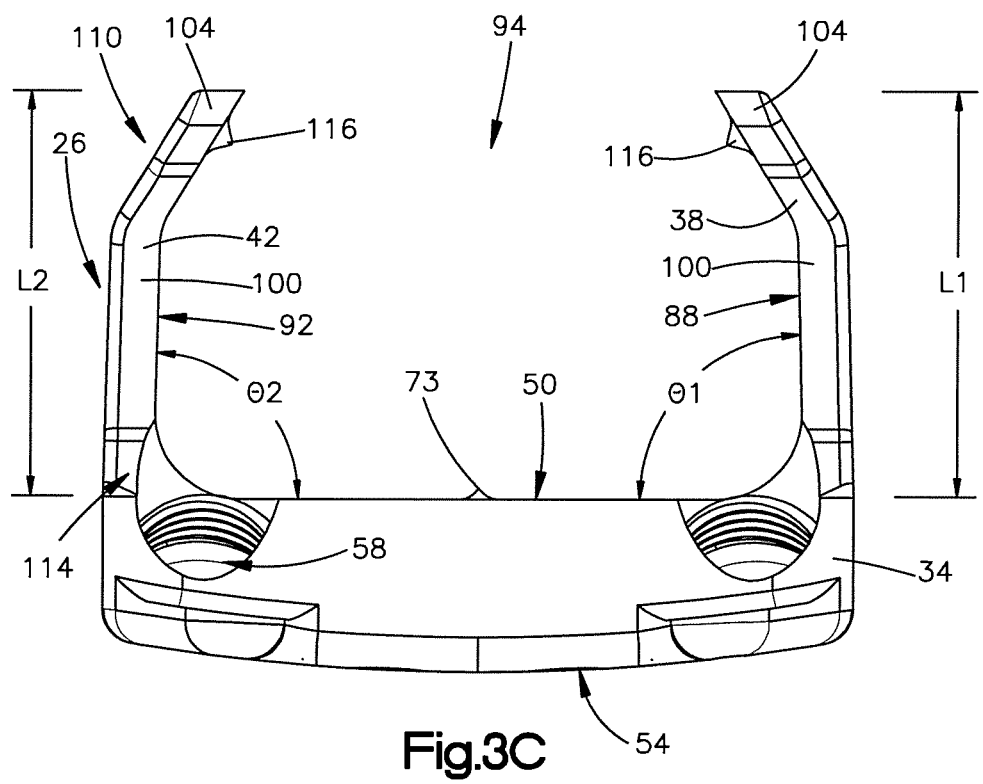
FIG. 3C is a top plan view of the intervertebral implant frame shown in FIG. 3A.
Figure 4A:
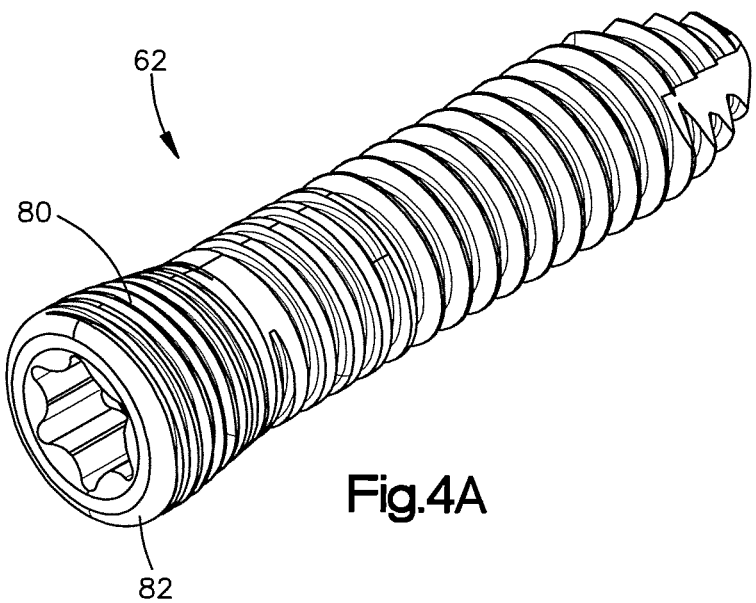
FIG. 4A is a perspective view of one of the fixation elements that is configured to affix the intervertebral implant shown in FIG. 2 to a vertebral body as illustrated in FIGS. 1A and 1B.
Figure 4B:
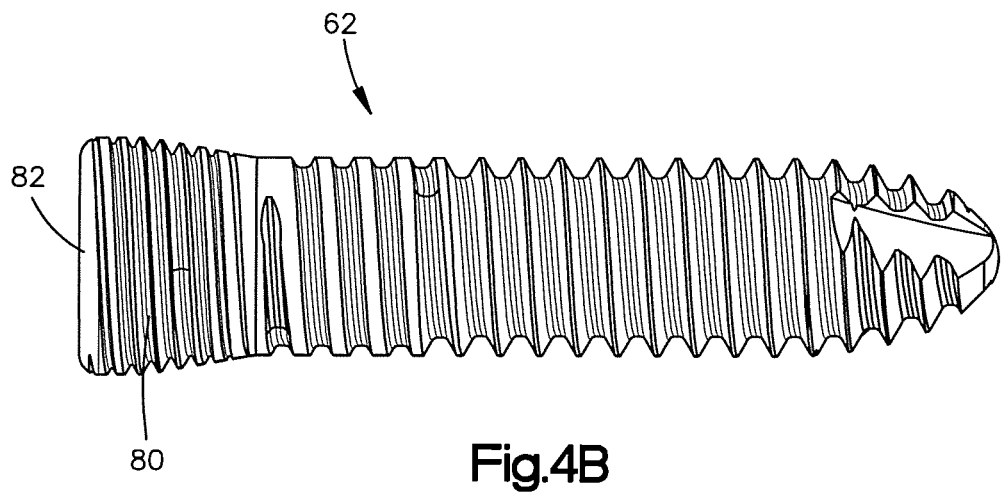
FIG. 4B is a side elevation view of the of the fixation element shown in FIG. 4A.

As shown in FIGS. 3A-3C, the support member 34 includes a body 46 that defines an inner surface 50, an outer surface 54, and at least one, such as two or such as four, fixation element receiving apertures 58 that extend through the body 46 from the outer surface 54 to the inner surface 50. Each fixation element receiving aperture 58 is configured to receive a respective fixation element, such as fixation element 62 shown in FIGS. 4A and 4B. While the fixation elements 62 are illustrated as screws, it should be appreciated that the fixation elements 62 may also be nails or any other fixation element configured to attach the intervertebral implant 22 to the first and second vertebral bodies 10a and 10b. As shown, the support member 34 can further include at least one, such as three tabs 64 that extend transversely from the body 46. The tabs 64 may sit on an anterior side of the vertebral bodies and prevent over-insertion of the frame 26 into the intervertebral space 18. In the illustrated embodiment, the support member 34 includes two superior tabs 64 and one inferior tab 64 that are each configured to sit flush or slightly proud of an anterior surface of the vertebral bodies depending on the patient's spinal anatomy and/or site preparation. It should be appreciated, however, that the support member 34 can include other configurations for the tabs 64. For example, the support member 34 can include a single superior tab 64 and two inferior tabs 64.

As shown in FIG. 3B, two of the fixation element receiving apertures 58 are inner apertures 66 that extend through the body 46 at a downward angle relative to the insertion direction I, and two of the fixation element receiving apertures 58 are outer apertures 70 that extend through the body 46 at an upward angle relative to the insertion direction I. The inner apertures 66 are configured to receive respective fixation elements, such as fixation element 62 shown in FIGS. 4A and 4B, to thereby attach the intervertebral implant 22 to the inferior vertebral body 10b. Similarly, the outer apertures 70 are configured to receive respective fixation elements 62 to thereby attach the intervertebral implant 22 to the superior vertebral body 10a. It should be appreciated, however, that the inner apertures 66 can extend through the body 46 at an upwards angle and the outer apertures 70 can extend through the body 46 at a downwards angle, as desired. Moreover, it should be appreciated that the support member 34 can define any number of fixation element receiving apertures 58 as desired.

As shown in FIG. 3B, the apertures 58 each define internal threads 78. The internal threads 78 are configured to engage external threads 80 defined by a head 82 of the respective fixation element 62 that is received within the apertures 58. It should be appreciated, however, that the apertures 58 can be void of threads as desired. The orientation of the apertures 58 may be configured such that the fixation elements that are received by the apertures 58 may have an insertion variance of +/−5 degrees and do not allow toggling or settling. Once fully received, the fixation elements may lock to the frame 26 to thereby increase the surgeon's reassurance of good screw trajectories and can act as a safety by preventing possibilities of over-insertion during implantation.

As shown in FIG. 3C, support member 34 can include a retention member 73 that extends from the inner surface 50. The retention member 73 is configured to help retain the spacer body 30 when the spacer body is being supported by the frame 26. The retention member 73 is illustrated as a spike though it should be appreciated, that the retention member 73 can have other configurations. For example, the retention member 73 can be configured as a blade.

As shown in FIGS. 2A, and 3A-3E, the first arm 38 and the second arm 42 each extend from the support member 34 and define a first distal terminal end 83 and a second distal terminal end 84, respectively. The first and second arms 38 and 42 each define gripping portions and support portions. The gripping portions are configured to retain the spacer body 30 while the support portions are configured to support the vertebral bodies 10a and 10b relative to each other. The gripping portions and the support portions can be a single structure or the support portions can be separate structures that extend from the gripping portions. The arms 38 and 42 can be radiolucent so as to increase fluoroscopy visibility. The first arm 38 includes a first inner spacer contacting surface 88 and the second arm 42 includes a second inner spacer contacting surface 92 that is spaced from the first inner spacer contacting surface 88 along a first direction, such as the lateral direction A. The inner surface of the support member 34, the first inner spacer contacting surface 88, and the second inner spacer contacting surface 92 together define a void 94 that is configured to receive and grip the spacer body 30. The terminal ends 83 and 84 are spaced apart from the support member along a second direction, such as the longitudinal direction L that is substantially perpendicular to the first direction so as to define first and second lengths $L_1$ and $L_2$, respectively of the first and second arms 38 and 42. The first and second arms 38 and 42 are sized such that the first and second lengths $L_1$ and $L_2$ are each greater than a length $L_3$ defined between an anterior end E of the inferior vertebral body 10b and the centroid M of the surface 14b of the inferior vertebral body 10b, as shown in FIG. 1C. It should be appreciated, that the first and second arms 38 and 42 can also be sized such that the first and second lengths $L_1$ and $L_2$ are greater than a length defined between an anterior end of the superior vertebral body 10a and a centroid of the surface 14a of the superior vertebral body 10a. The first and second lengths $L_1$ and $L_2$ may be between about 3.5 mm and about 12 mm, between about 6.0 mm and about 10 mm, and preferably about 9.5 mm. In some embodiments, the support member 34, the first arm 38, and the second arm 42 extend around at least 51% of the spacer body 30, and preferably around at least 80% of the spacer body 30.

The flexible arms 38 and 42 can have a transverse height and a lateral width that at least partially define a cross-sectional area of the arms 38 and 42. The arms 38 and 42 can have a cross-sectional area that may vary so long as the arms 38 and 42 are capable of elastically deforming or flexing to thereby allow the frame 26 to receive the spacer body and subsequently apply a retention force to the spacer body 30 after the frame 26 has received the spacer body 30. In that regard, the arms 38 and 42 are configured to elastically flex laterally outwardly away from each other, or otherwise elastically deform from a first position to a second flexed position to allow the frame 26 to receive the spacer body 30. It should be appreciated that the first position can be a relaxed position of the arms 38 and 42 or a flexed position of the arms 38 and 42 that is outwardly flexed with respect to a relaxed position. At least respective portions of the arms 38 and 42, such as contact locations 320 and 324 (see FIG. 6E), are further spaced from each other in the second position than when in the first position. Once the spacer body 30 is disposed between the arms 38 and 42, the arms 38 and 42 may flex inwardly toward each other to a third or engaged position whereby the arms 38 and 42 engage the spacer body 30 so as to secure the frame 26 to the spacer body 30 as shown in FIG. 2. It should be appreciated that the third position can be outwardly flexed with respect to the first position, and can be substantially equal to the first position. Thus, the respective portions of the arms 38 and 42 can be further spaced from each other when in the third position with respect to the first position, or the respective portions of the arms 38 and 42 can be spaced from each other when in the third position a distance substantially equal to the distance that the respective portions of the arms 38 and 42 are spaced when in the first position. Thus, it can be said that when the arms 38 and 42 are in the third position, at least respective portions of the arms 38 and 42 are spaced apart a distance equal to or greater than (or no less than) the distance that the arms 38 and 42 are spaced when in the first position. It will be further appreciated from the description below in accordance with certain embodiments (see, for instance FIG. 14C) that at least respective portions of the arms 38 and 42 can be spaced apart a distance when in the engaged position that is less than the distance that the respective portions of the arms 38 and 42 are spaced apart when in the first position.

As shown in FIG. 3C, the first and second arms 38 and 42 extend from the support member 34 such that the first and second arms 38 and 42 are angled toward each other so as to push the spacer body 30 toward the other of the first and second arms 38 and 42 and toward the support member 34. For example, the inner surface of the support member 34 and the first inner spacer contacting surface 88 form an angle $Ø_1$ that is less than 90 degrees, and the inner surface 50 of the support member 34 and the second inner spacer contacting surface 92 form an angle $\varnothing_2$ that is less than 90 degrees. In the illustrated embodiment, $\varnothing_1$ and $\varnothing_2$ are each about 88 degrees, though it should be appreciated that $\varnothing_1$ and $\varnothing_2$ may be any angle as desired, and may be different angles with respect to each other.

Figure 3D:
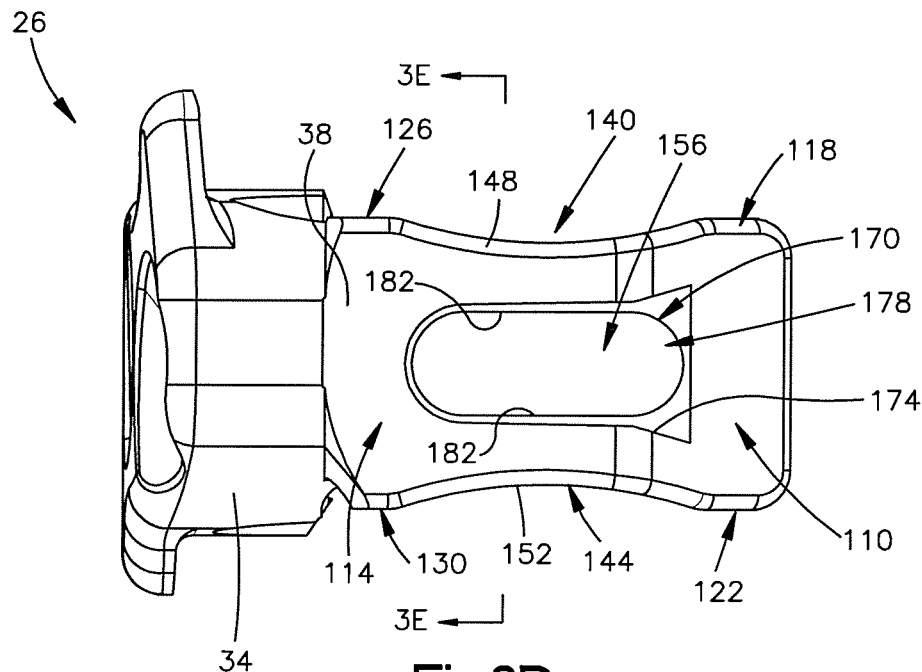
FIG. 3D is a side elevation view of the intervertebral implant frame shown in FIG. 3A.

As shown in FIGS. 3C and 3D, each arm 38 and 42 includes a substantially straight portion 100 that extends from the support member 34, and a distal bent or angled portion 104 that extends from a distal end of the straight portion 100 toward the other of the bent portions 104 such that the bent portions 104 are configured to contact a distal surface of the spacer body 30. As shown, the bent portions 104 at least partially wrap around the spacer body 30 to thereby prevent the spacer body 30 from separating from the frame 26 after the spacer body 30 has been retained by the frame 26. As shown in FIG. 3A, each arm 38 and 42 can include at least one, such as a plurality of retention members 116 that extend out from the first and second inner spacer contacting surfaces 88 and 92. In the illustrated embodiment, the retention members 116 define teeth that extend out of the bent portions 104 so as to form a column of teeth on each bent portion 104. The retention members 116 are configured to engage the spacer body 30 when the frame 22 is retaining the spacer body 30 to thereby ensure that the spacer body 30 remains retained by the frame 22. It should be appreciated, however, that the retention member 116 can have any configuration as desired, so long as the retention member 116 is capable of engaging the spacer body 30. For example, the retention members 116 can be spikes that extend from the inner surfaces 88 and 92 at an angle, elongate blades, or even punches that can be punched into the spacer body 30 by an individual after the spacer body 30 is disposed in the frame 26.

As shown in FIG. 3D, the arms 38 and 42 may be configured to assist in bearing compressive loads by the vertebral bodies 10a and 10b to thereby mitigate subsidence and settling. As shown, each arm 38 and 42 defines a respective distal portion 110 and a respective proximal portion 114. The distal portions 110 are spaced apart from the proximal portions 114 along the longitudinal direction L such that when the frame 26 is disposed in the intervertebral space 18, the distal portions 110 are on the posterior side of the centroid M of the surface 14b of the inferior vertebral body 10b, and the proximal portions 114 are on the anterior side of the centroid M of the surface 14b of the inferior vertebral body 10b. Each distal portion 110 defines a superior vertebral body contacting surface 118 and an inferior vertebral body contacting surface 122. Similarly, each proximal portion 114 defines a superior vertebral body contacting surface 126 and an inferior vertebral body contacting surface 130. Because of the length of the arms 38 and 42 and because of the transverse height of the arms 38 and 42 at their distal and proximal portions, the frame 26 can bear compressive loads from the vertebral bodies if the spacer body 30 were to subside.

As shown in FIG. 3D, the arms 38 and 42 may be configured to conform to the lordotic curve of the spine and in particular of the intervertebral space 18 in which the frame 26 is to be disposed. For example, a line drawn between the superior vertebral body contacting surfaces 118 and 126 of the first arm 38 forms an angle that is between about 0 degrees and about −5 degrees with respect to the insertion direction I, and a line drawn between the inferior vertebral body contacting surfaces 122 and 130 of the first arm forms a line that is between about 0 degrees and about 5 degrees with respect to the insertion direction I. Similarly, a line drawn between the superior vertebral body contacting surfaces 118 and 126 of the second arm 42 forms an angle that is between about 0 degrees and about −5 degrees with respect to the insertion direction, and a line drawn between the inferior vertebral body contacting surfaces 122 and 130 of the second arm 42 forms an angle that is between about 0 degrees and about 5 degrees with respect to the insertion direction I. It should be appreciated, however, that the lines drawn between the superior vertebral body contacting surfaces 118 and 126, and between the inferior vertebral body contacting surfaces 122 and 130 can be any angle as desired. For example, the lines may be parallel to each other. Therefore, it can be said that a first plane is defined by the superior vertebral body contacting surfaces, and a second plane is defined by the inferior vertebral body contacting surfaces. The first plane and the second plane can be parallel to each other or converge toward each other.

As shown in FIG. 3D, each arm 38 and 42 further includes a superior cut-out 140 and an inferior cut-out 144 to thereby provide visual access to the superior vertebral body 10a and to the inferior vertebral body 10b respectively when the frame 26 is disposed in the intervertebral space 18. The cut-outs 140 and 144 are each disposed between the proximal portions 114 and distal portions 110 of the first and second arms 38 and 42. As shown, the superior cut-outs 140 extend laterally through an upper portion of the arms 38 and 42 so as to define upper curved recesses 148 in the straight portions 100 of the arms 38 and 42. Similarly, the inferior cut-outs 144 extend laterally through a lower portion of the arms 38 and 42 so as to define lower curved recesses 152 in the arms 38 and 42. It should be appreciated that the superior and inferior cut-outs 140 and 144 can have other configurations as desired. For example, the cut-outs 140 and 144 can define rectangular channels that extend through the arms 38 and 42.

Figure 3E:
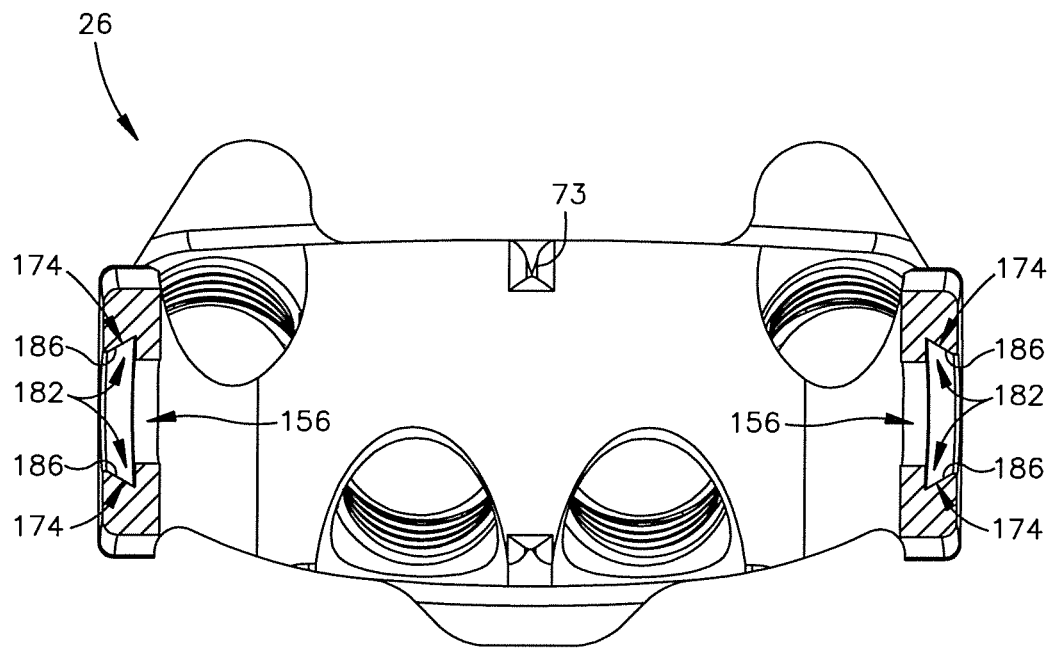
FIG. 3E is a cross-sectional view of the intervertebral implant frame shown in FIG. 3D through the line 3E-3E.

As shown in FIGS. 3D and 3E, each arm 38 and 42 can further include a window 156 that extends laterally through the straight portions 100 of the arms 38 and 42 between the superior and inferior cut-outs 140 and 144. The windows 156 are configured to provide visual access to the spacer body 30 through the first and second arms 38 and 42 when the frame 26 is retaining the spacer body 30. As shown, the windows 156 are oval shaped and elongate along the longitudinal direction L. It should be appreciated, however, that the windows 156 can have any shape as desired. For example, the windows 156 can also be rectangular shaped.

As shown in FIGS. 3A, 3D, and 3E, each arm 38 and 42 includes an engagement member 170 that is configured to receive a first and a second external expansion force, respectively, from an expansion instrument prior to insertion of the spacer body 30 into the void 94 such that at least one of the first and second arms 38 and 42 elastically expands or elastically flexes with respect to the other of the first and second arms 38 and 42 in response to the expansion forces. As shown in FIG. 3A, the engagement members 170 each define a dove-tailed slot 174 that defines an opening 178 at its distal end such that the expansion instrument can engage the dove-tailed slot 174 in a direction that is opposite to the insertion direction I of the frame 26. As shown in FIG. 3D, the dove-tailed slots 174 are wider at the openings 178 and taper as they extend proximally. The wider openings 178 provide a guide for the expansion instrument to engage the engagement members 170. As shown in FIG. 3A, the dove-tailed slots 174 each include a pair of opposed recesses 182 that define angled engagement surfaces 186. It should be appreciated, however, that the engagement members 170 can have any configuration as desired so long as they can receive respective expansion forces.

Now referring to FIG. 5A, the spacer body 30 that is received within the frame 26 is preferably made from a bone graft material such as allograft bone, autograft bone, or xenograft bone, for example. As shown in FIG. 5A, the spacer body 30 can include cancellous bone 190 that is at least partially surrounded by cortical bone 194. It should be appreciated, however, that the spacer body 30 can be made from only cancellous bone 190 or from only cortical bone 194.

As shown in FIGS. 5B-5D, the spacer body can alternatively be made from a synthetic material. Referring to FIGS. 5B-5D, the spacer body 30 is sized and dimensioned to fit within the frame 26. Though not required, the spacer body may have a lateral width of between about 10 mm and about 16 mm, a longitudinal length of between about 10 mm and 17 mm, and a transverse height that is between about 5 mm and about 12 mm. The outer footprint of the spacer body 30 can vary and the frame 26 may still be able to retain the spacer body 30. That is, the frame 26 or at least the arms 38 and 42 are configured to retain a first spacer body 30 having a first maximum width, a first outer footprint, or a first cross-sectional dimension, and a second spacer body having a second maximum width, a second outer footprint, or a second cross-sectional dimension that is different than those of the first spacer body 30. Therefore, the frame 26 and in particular the arms 38 and 42 can retain spacer bodies 30 that are made from bone shaped by the surgeon and not just spacer bodies 30 that are machined to have specific dimensions prior to insertion into the frame 26.

As shown in FIGS. 5B-5D, the spacer body 30 can define a superior or upper or outer bone engaging surface 200 and an opposed inferior or lower or outer bone engaging surface 204. The surfaces 200 and 204 are configured to engage the superior and inferior surfaces 14a and 14b, respectively of the vertebral bodies 10a and 10b. The spacer body 30 can further define side surfaces 208 that are configured to be engaged by the first and second inner spacer contacting surfaces of the first and second arms 38 and 42 to thereby retain the spacer body 30 within the frame 26.

As shown in FIGS. 6A-6E, the spacer body 30 can be coupled to the frame 26 using an actuation instrument 210 that is configured as an expansion instrument. The instrument 210, the frame 26, and in some cases the spacer body 30 can together define an intervertebral implant system 214. The expansion instrument 210 includes a grip 212 and a handle 213. The grip 212 is configured as an expansion grip and is configured to apply the first and second expansion forces to the engagement members 170 of the first and second arms 38 and 42. The first and second expansion forces will elastically expand the first and second arms 38 and 42 of the frame 26 to thereby allow the spacer body 30 to be received by the void 94 of the frame 26.

As shown, the instrument 210 includes a first arm 220 that is configured to releasably couple to the first arm 38 of the frame 26, and a second arm 224 that is rotatably coupled to the first arm 220 at a first pivot 228 and is configured to releasably couple to the second arm 42 of the frame 26. The first and second arms 220 and 224 are configured as expansions arms. The first and second expansion arms 220 and 224 are pivotally coupled to each other at the first pivot 228 such that rotation of the first and second expansion arms 220 and 224 about the first pivot 228 causes the first and second arms 38 and 42 of the frame 26 to elastically flex away from each other when the instrument 210 is coupled to the frame 26. Therefore, the instrument 210 is configured to have a first position or configuration whereby the instrument 210 can be coupled to the frame 26, and a second position or configuration whereby the instrument 210 is applying expansion forces to the arms 38 and 42 of the frame 26 so that the frame can receive the spacer body 30.

Figure 6B:
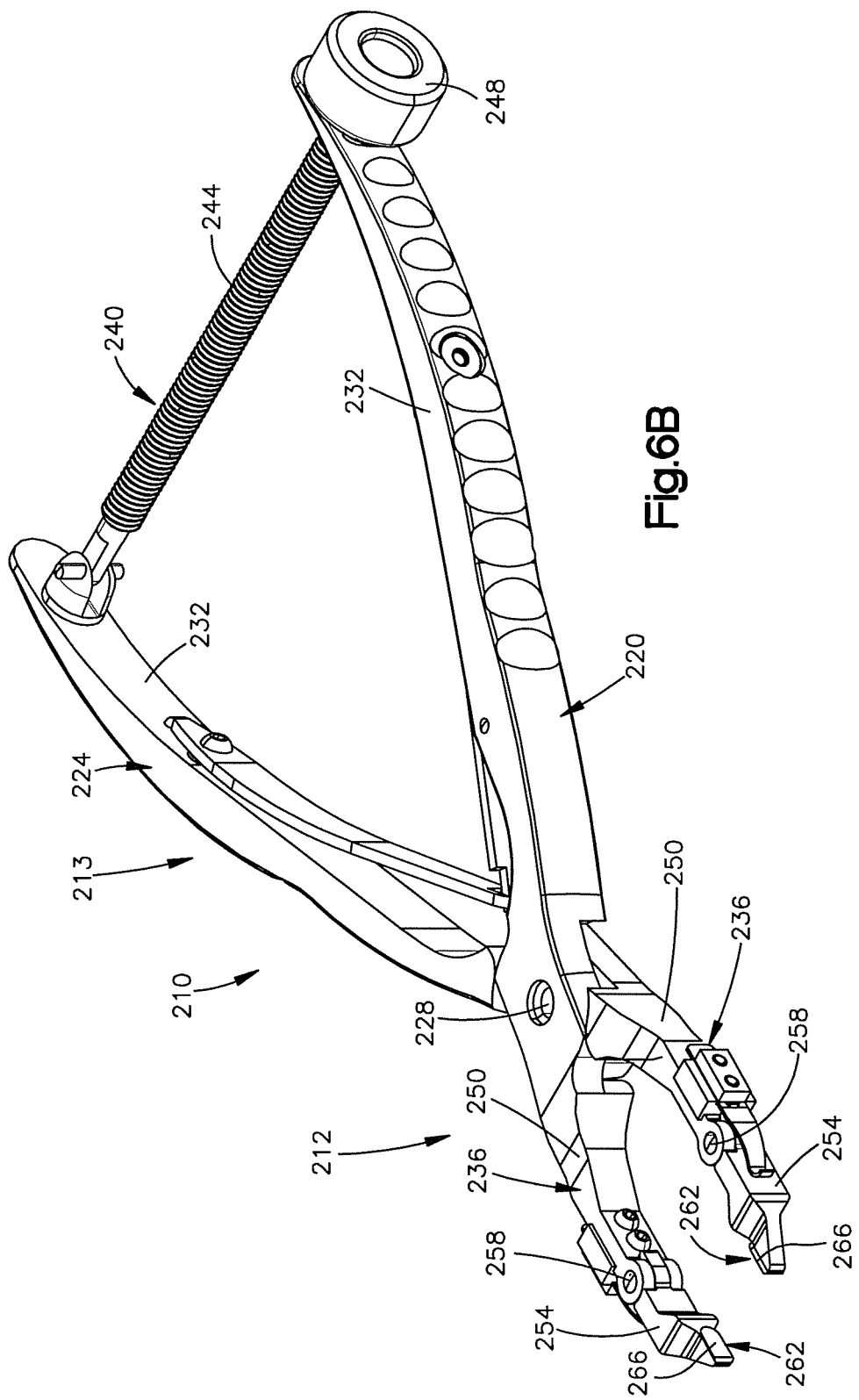
FIG. 6B is a perspective view of the expansion instrument shown in FIG. 6A, the expansion instrument including a first expansion arm and a second expansion arm coupled to the first expansion arm at a first pivot, each expansion arm having a handle portion and a gripping portion that combine to define a handle of the expansion instrument and the expansion grip illustrated in FIG. 6A.

As shown in FIGS. 6B and 6C, each expansion arm 220 and 224 includes a handle portion 232 that extends proximally from the first pivot 228 and a gripping portion 236 that extends distally from the first pivot 228. The handle portions 232 define the handle 213, and the gripping portions 236 define the grip 212. The handle portions 232 are configured to be gripped by an individual such that the handle portions 232 can be squeezed or otherwise moved toward each other. The expansion instrument 210 can further include a handle locking mechanism 240 that is configured to lock the handle portions 232 relative to each other after the handle portions 232 have been moved toward each other. In the illustrated embodiment, the locking mechanism 240 includes a threaded shaft 244 and a nut 248. As at least one of the handle portions 232 is moved along the shaft 244, the nut 248 can be threaded along the shaft 244 to thereby lock the handle portions 232 relative to each other. It should be appreciated, however, that the locking mechanism 240 can include other configurations, as desired. For example, the locking mechanism 240 can have a ratchet configuration.

As shown in FIGS. 6C and 6D, the gripping portions 236 are configured to expand the frame arms as the handle portions 232 are moved toward each other. Each gripping portion 236 includes an extension member 250 that extends distally from the first pivot 228, and a gripping member 254 that is pivotally coupled to a distal end of the extension member 250 at a second pivot 258. Each gripping member 254 includes an engagement member 262 that is configured to engage respective engagement members 170 of the first and second arms 38 and 42 of the frame 26. As shown in FIG. 6D, the engagement members 262 are dove-tailed members 266 that are opposed to each other and are configured to mate with the dove-tailed slots of the first and second arms 38 and 42 to thereby couple the expansion instrument 210 to the frame 26. As shown, each dove-tailed member 266 includes a pair of transversely opposed protrusions 280 that each define an angled engagement surface 284 that is configured to abut or otherwise contact a respective angled engagement surface 186 of the slots 174 when the engagement members 262 are mated with the engagement members 170. It should be appreciated that the engagement members 262 can have other configurations as desired. For example, the engagement members 262 and the engagement members 170 can be reversed.

As shown in FIG. 6D, a proximal end of each engagement member 262 defines a tapered lead-in portion 270 that allows the engagement members 262 to easily be guided into the openings 178 of the engagement members 170. Therefore, the expansion instrument 210 can easily be coupled to the frame 26 along a direction that is opposite the insertion direction I. That is, if the frame 26 is stationary, the expansion instrument 210 can be coupled to the frame 26 by translating the instrument 210 along a direction that is opposite the insertion direction I.

As shown in FIG. 6C, each gripping member 254 includes a pair of stops 300 that extend proximally toward the extension member 250 and are spaced apart from the extension member 250. As the gripping member 254 rotates about the second pivot 258 the stops 300 will limit the rotation by contacting the extension member 250. Therefore, the angular range in which the gripping members 254 can rotate about the second pivots 258 will depend on the distance in which the stops 300 are spaced apart from the extension members 250.

As shown in FIG. 6C, each gripping portion 236 further includes a biasing member 304 that is configured to bias the gripping members 254 toward each other. In the illustrated embodiment, the biasing members 304 are leaf springs 308 that are coupled to the extension members 250 and urge against an outer surface of the gripping members 304. By biasing the gripping members 254 toward each other, the expansion instrument 210 can more easily and more predictably be coupled to the frame 26. It should be appreciated, however, that the biasing members 304 can have other configurations as desired. For example, the biasing members can be elastically flexible wires and can be disposed within the gripping members 254 as desired.

Figure 6E:
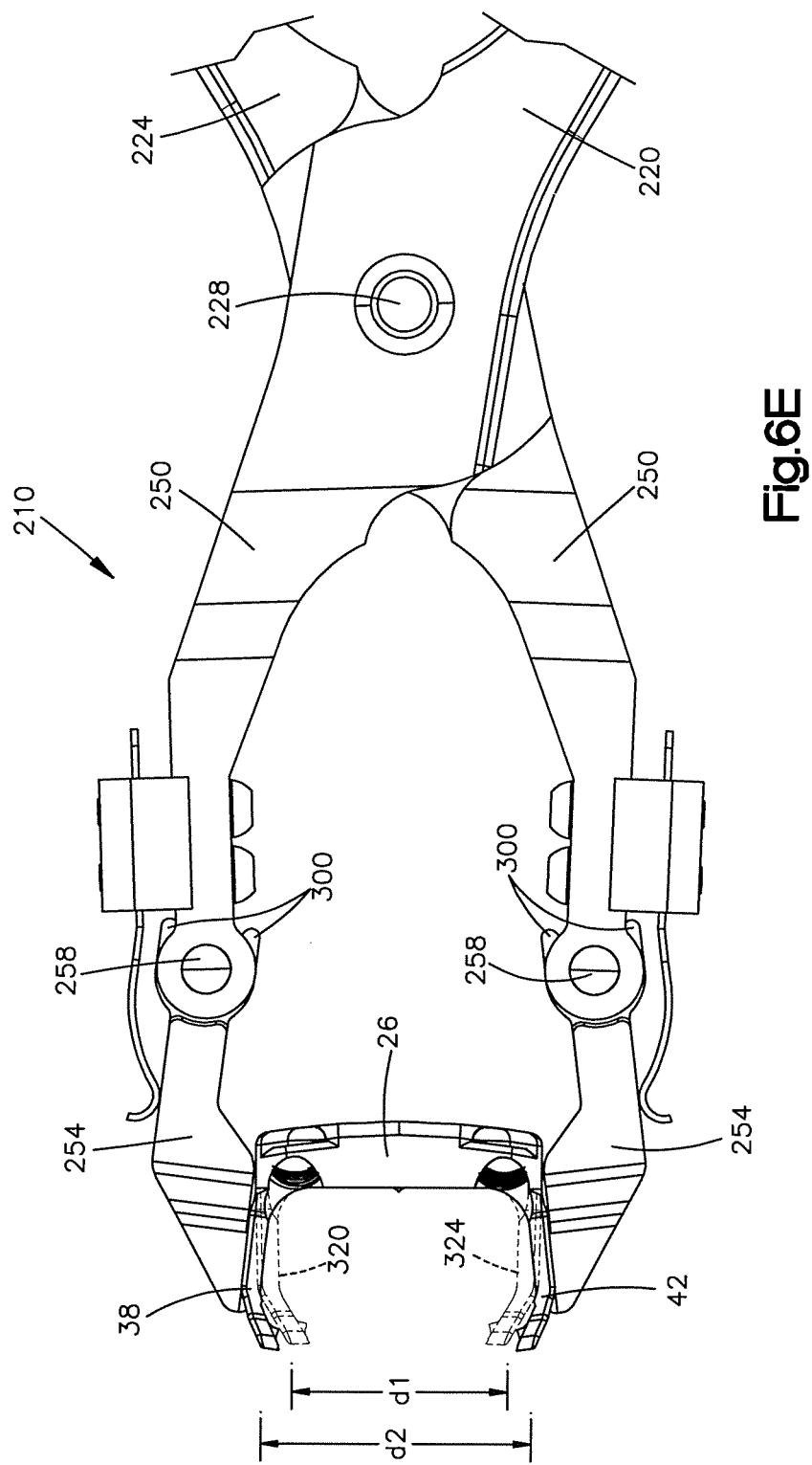
FIG. 6E is an enlarged top plan view of the expansion grip shown in FIG. 6B, coupled to the first and second arms of the frame shown in FIG. 3A, showing the expansion instrument actuated from a first position to a second position, whereby the expansion grip applies an expansion force to the first and second arms of the frame when the expansion instrument is in the second position, the expansion force biasing the first and second arms of the frame to flex away from each other.

In operation and in reference to FIG. 6E, the expansion instrument 210 is coupled to the frame 26 by placing the engagement members 262 of the instrument 210 distal to the engagement members 170 of the frame 26. By translating or otherwise moving the frame 26 or the instrument 210 toward the other, the engagement members 262 will engage the engagement members 170 to thereby couple the frame 26 to the instrument 210 such that the second pivots 258 of the instrument 210 abut an outer surface of the flexible arms 38 and 42 proximate to the support member 34. By squeezing the handle portions 232 toward each other, the extension member 250 of the first expansion arm 220 will rotate counterclockwise about the first pivot 228 and the gripping member 254 of the first expansion arm 220 will rotate clockwise about the second pivot 258. Conversely, the extension member 250 of the second expansion arm 224 will rotate clockwise about the first pivot 228 and the gripping member 254 of the second expansion arm 224 will rotate counterclockwise about the second pivot 258.

This rotation will cause at least one of the first and second arms 38 and 42 to elastically flex away from the other. For example, the first and second inner spacer contacting surfaces 88 and 92 of the first and second arms 38 and 42 can define respective first and second respective contact locations 320 and 324, and at least one of the first and second arms 38 and 42 is flexible so as to be movable between a first position, whereby the frame 26 defines a first distance $d_1$ that extends along the lateral direction A between the first and second contact locations 320 and 324, and a second position, whereby the frame 26 defines a second distance $d_2$ that extends along the lateral direction A between the first and second contact locations 320 and 324. It should be appreciated that the first and second contact locations 320 and 324 can be located anywhere along the arms 320 and 324 so long as they remain the same when the first and second distances are measured.

As shown in FIG. 6E, the second distance $d_2$ is greater than the first distance $d_1$ such that when in the second position, the void 94 defines a cross-sectional dimension that is greater than that of the spacer body 30 such that the void 94 is sized to receive the spacer body 30. While the arms 38 and 42 are elastically flexed, at least one of the arms 38 and 42 is biased toward the first position. Therefore, when the handle portions 232 of the instrument 210 are released, the arms 38 and 42 will flex back to a third position, and when in the third position, the frame 26 defines a third distance $d_3$ that extends along the lateral direction A between the first and second contact locations 320 and 324 and is less than the second distance $d_2$ (See FIG. 2B). When in the third position at least one of the first and second inner contacting surfaces 88 and 92 of the arms 38 and 42 will apply a retention force against the spacer body 30 along a direction toward the other of the first and second inner spacer contacting surfaces 88 and 92.

In another embodiment and in reference to FIGS. 7A-7C, an intervertebral implant system 350 can include an intervertebral implant frame 426, and an actuation instrument 428 that is also configured as an expansion instrument. The frame 426 includes a support member 434, a first arm 438 that extends from the support member 434, and a second arm 442 that extends from the support member 434. The first and second arms 438 and 442 are flexible arms and are configured to elastically flex away from each other so that the frame 426 can receive a spacer body 30. The support member 434, the first arm 438, and the second arm 442 are similar to the support member 34, the first arm 38, and the second arm 42 shown in FIG. 3A, and include like structure unless otherwise described.

As shown in FIG. 7C, each of the first and second arms 438 and 442 includes a straight portion 446 and a bent portion 450 that extends from a distal end of the straight portion 446 at angle toward the other of the bent portions 450. Each arm 438 and 442 further includes an engagement member 454 that defines a slot 458 that extends through the respective arm 438 and 442. As shown the slots 458 extend through the straight portions 446 at substantially the same angle in which the bent portions 450 extend from the distal end of the straight portions 446. Moreover, the slots 458 extend through the straight portions 446 and into a cavity 460 defined by the bent portions 450. Each bent portion 450 further includes a retention bump 461. The bumps 461 are configured to provide a tactile feedback indicating that the expansion instrument 428 is coupled to the arms 438 and 442.

As shown in FIGS. 7A-7C, the expansion instrument 428 can include a pair of removable clips 470 that are configured to engage the slots 458 defined by the arms 438 and 442 by translating the clips 470 distally or along a direction that has a directional component that is the same as the insertion direction I. As shown, each clip 470 can be a substantially straight elongate member 474 having an engagement member 476 that is defined by a pair of elongate cantilevered beams 478 at its distal end that are separated by a recess 482. An outer beam 478 can include a recess 479 that is configured to receive the retention bump 461 and provide an indication that the clips 470 are properly coupled to the arms 438 and 442. As shown in FIG. 7B, each clip 470 can be attached to a respective arm 438 and 442 by inserting one of the cantilevered beams 478 of a respective clip 470 into a slot 458 of the respective arms 438 and 442. The cantilevered beam 478 that is inserted into the slot 458 will be received by the cavity 460 defined by the bent portion 450.

Once coupled to the arms 438 and 442, the clips 470 extend out from the arms 438 and 442 at an angle such that the clips 470 diverge from each other as they extend proximally. By squeezing a proximal portion of the clips 470 toward each other, the cantilevered beams 478 apply an expansion force to the engagement members 454 or at least to the bent portions 450 such that the arms 438 and 442 elastically flex away from each other. While flexed, the frame 426 can receive the spacer body 30. By releasing the clips 470, the arms 438 and 442 will apply a retention force to the spacer body 30 to thereby retain the spacer body 30 in the frame 426.

Figure 8A:
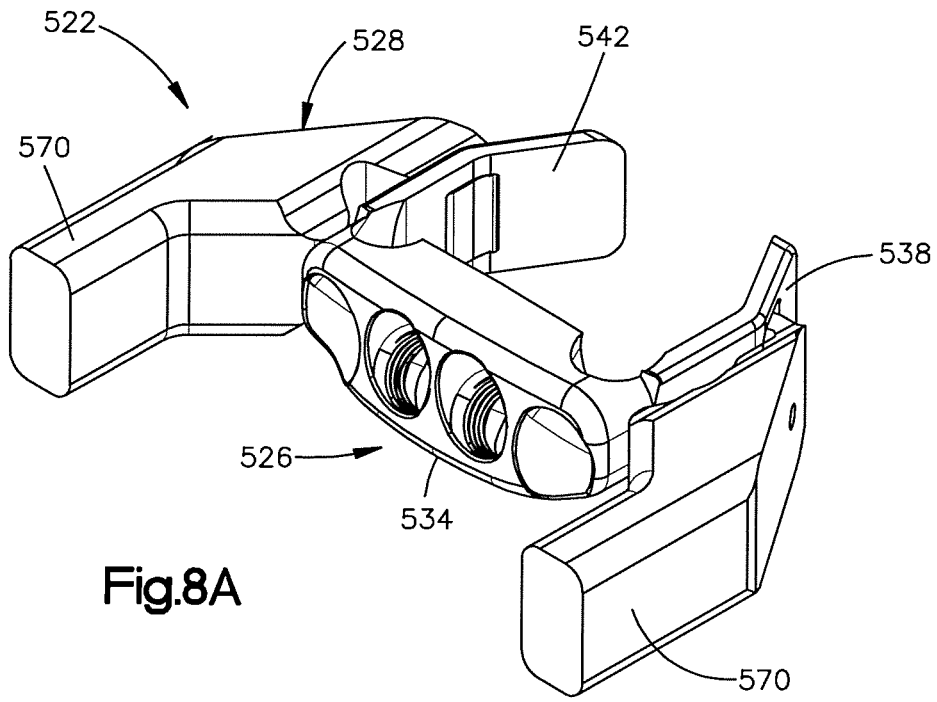
FIG. 8A is a perspective view of an intervertebral implant system constructed in accordance with another embodiment, the system including a intervertebral implant frame and an actuation instrument configured as an expansion instrument that comprises a pair of clips that engage first and second arms of the frame along a direction that is opposite to the insertion direction of the frame.
Figure 8B:
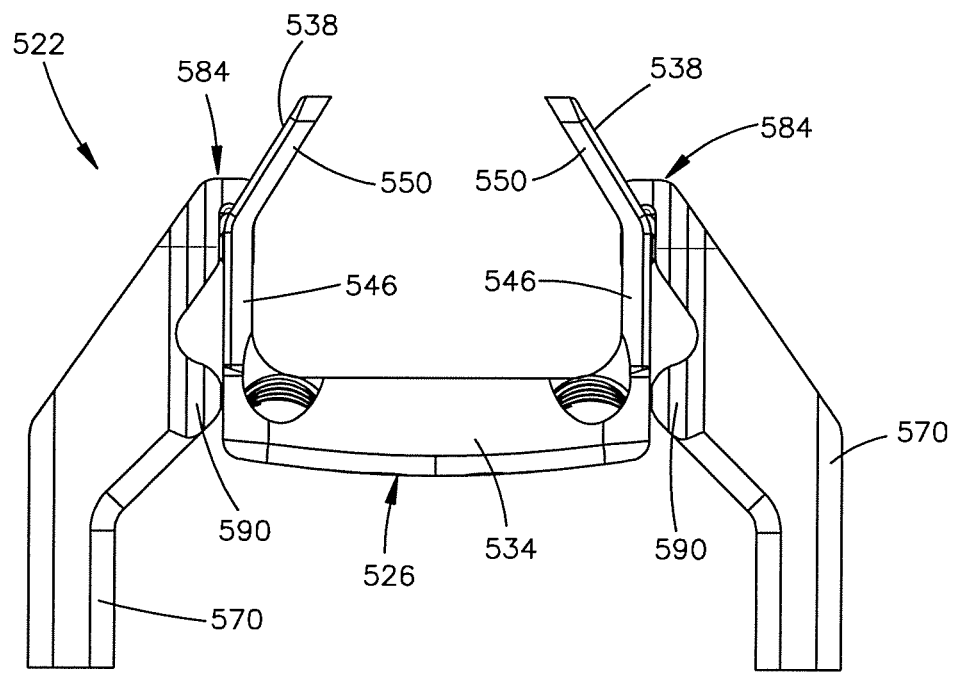
FIG. 8B is a top plan view of the system shown in FIG. 8A.
Figure 8C:
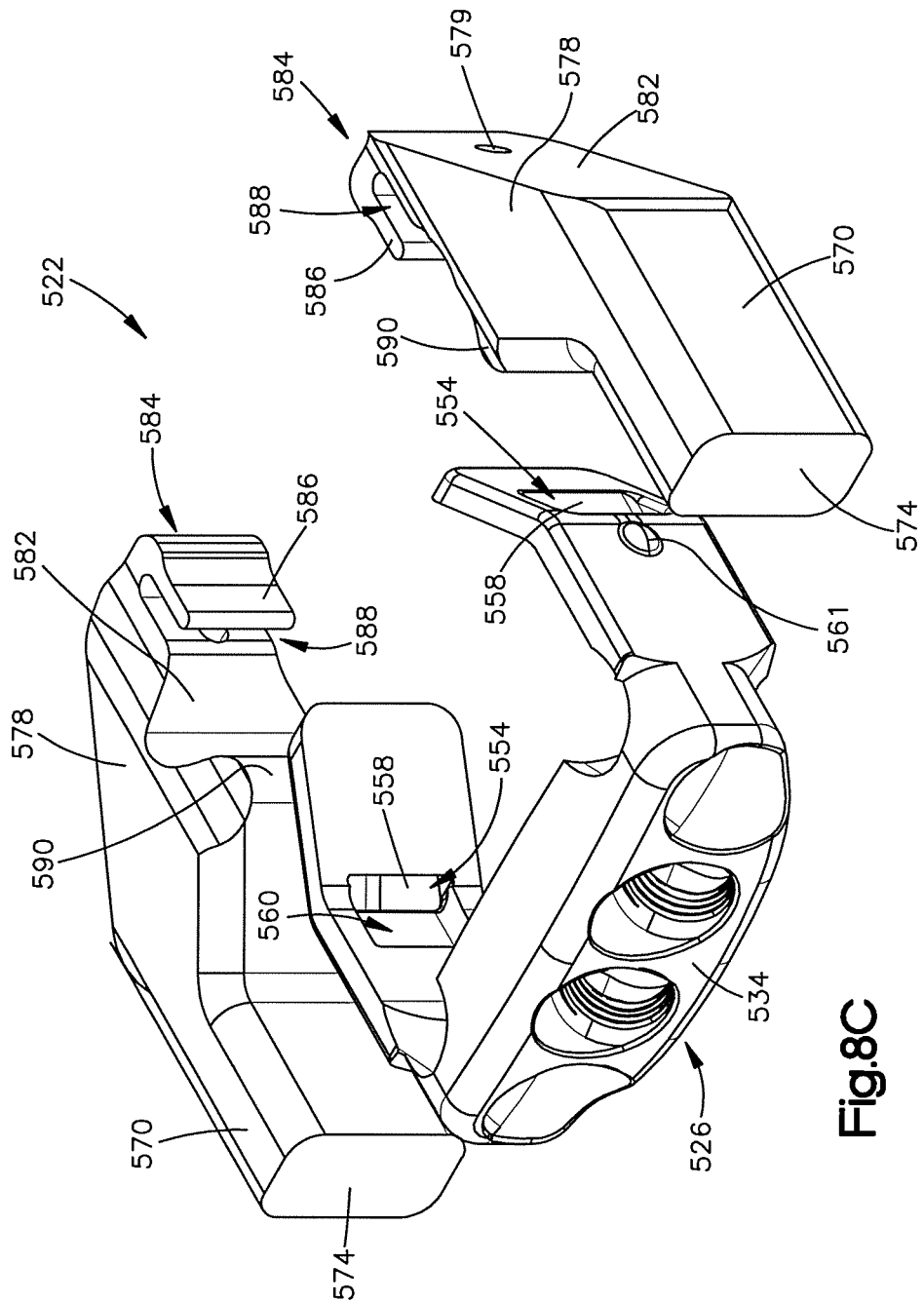
FIG. 8C is an exploded view of the system shown in FIG. 8A.

In another embodiment and in reference to FIGS. 8A-8C, an intervertebral implant system 522 can include an intervertebral implant frame 526, and an actuation instrument 528 that is configured as an expansion instrument. The frame 526 includes a support member 534, a first arm 538 that extends from the support member 534, and a second arm 542 that extends from the support member 534. The first and second arms 538 and 542 flexible arms and are configured to elastically flex away from each other so that the frame 526 can receive a spacer body 30. The support member 534, the first arm 538, and the second arm 542 are similar to the support member 34, the first arm 38, and the second arm 42 shown in FIG. 3A, and include like structure unless otherwise described.

As shown in FIG. 8C, each of the first and second arms 538 and 542 includes a straight portion 546 and a bent portion 550 that extends from a distal end of the straight portion 546 at angle toward the other of the bent portions 550. Each arm 538 and 542 further includes an engagement member 554 that defines a slot 558 that extends through the respective arm 538 and 542. As shown the slots 558 extend through the bent portions 550 along a direction that is opposite the insertion direction I. Moreover, the slots 558 extend into a cavity 560 that is defined by each straight portion 546. Each straight portion 546 further includes a retention bump 561. The bumps 561 are configured to provide a tactile feedback indicating that the expansion instrument 528 is coupled to the arms 538 and 542.

As shown in FIGS. 8A-8C, the expansion instrument 528 can include a pair of removable clips 570 that are configured to engage the slots 558 defined by the arms 538 and 542 by translating the clips 570 proximally or along a direction that is opposite the insertion direction I. As shown, each clip 570 includes a handle portion 574 and a gripping portion 578 that extends distally from the handle portion 574. Each gripping portion 578 includes a body 582 and an engagement member 584 that extends out from the body 582. As shown, each engagement member 584 defines a proximally extending protrusion 586 that is spaced from the 582 such that a recess 588 is defined between the protrusion 586 and body 582. Each gripping portion 578 further includes a shoulder 590 that extends out from the body 582 and is configured to abut the arms 538 and 542 proximate to the support member 526 when the clip 570 is coupled to the frame 526. Each clip 570 further includes a recess 579 that is configured to receive the retention bump 561 and provide an indication that the clips 570 are properly coupled to the arms 538 and 542. As shown in FIG. 8B, each clip 570 can be attached to a respective arm 538 and 542 by inserting the protrusion 586 of a respective clip 470 into a slot 558 of a respective arm 538 and 542. The protrusion 586 will be received by the cavity 560 defined by the straight portion 546.

Once coupled to the arms 538 and 542, the clips 570 extend out from the arms 538 and 542 such that the handle portions 574 are proximal to the front of the frame 526 and the shoulders 590 are abutting the arms 538 and 542 proximate to the support member 526 as shown in FIG. 8B. By squeezing the handle portions 574 toward each other, clips 570 rotate about the shoulders 590 and the protrusions 586 apply an expansion force to the engagement members 554 or to at least the straight portions 546 such that the arms 538 and 542 elastically flex away from each other. While flexed, the frame 526 can receive the spacer body 30. By releasing the clips 570, the arms 538 and 542 will apply a retention force to the spacer body 30 to thereby retain the spacer body 30 in the frame 526.

It should be appreciated that the engagement members of the frames 26, 426, and 526, and the engagement members of the instruments 210, 428, and 528 are interchangeable. Therefore, for example, frame 26 and instrument 210 can include any of the engagement members 170, 262, 454, 476, 554, and 584 so long as the engagement members of the frame 26 can mate with the engagement members of the instrument 210 to thereby releasably couple the frame 26 to the instrument 210.

Figure 9A:
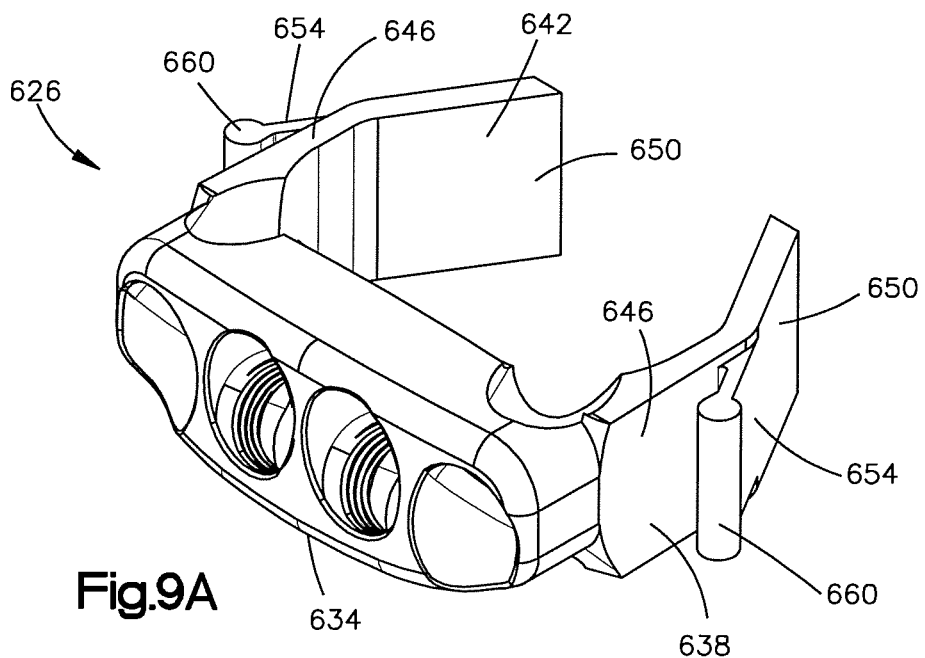
FIG. 9A is a perspective view of an intervertebral implant frame constructed in accordance with another embodiment, the frame including a first arm, a second arm, and a respective expansion member that extends out from and is integral to a respective arm of the frame.
Figure 9B:
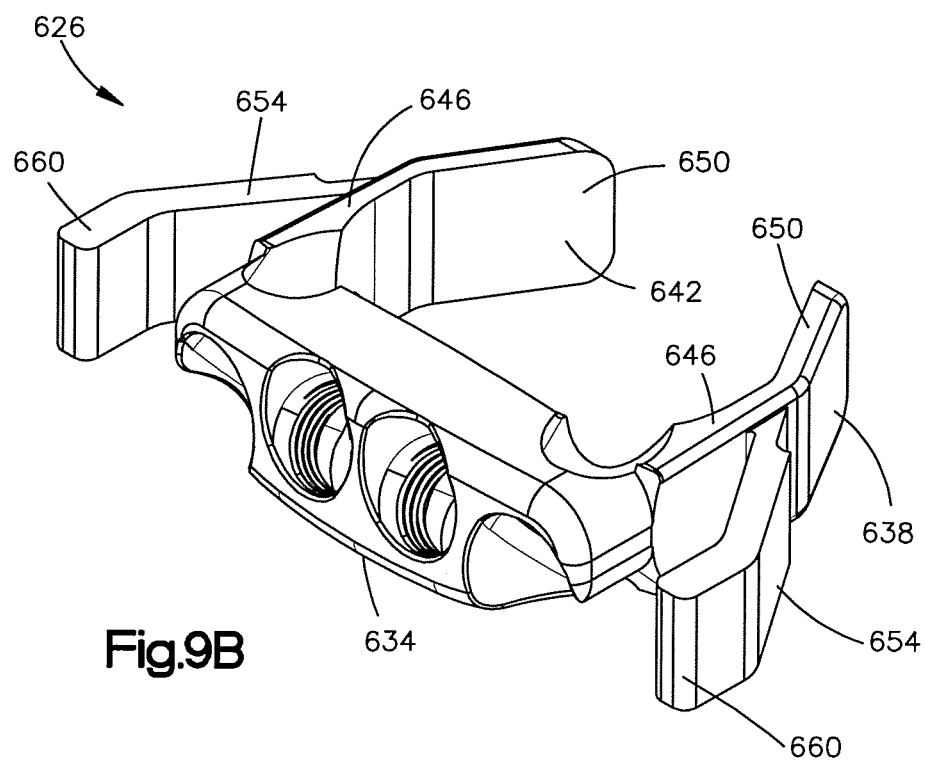
FIG. 9B is a perspective view of an intervertebral implant frame constructed in accordance with another embodiment, the frame including, a support member, a first arm, a second arm, and a respective expansion member that extends out from and is integral to each arm of the frame, the expansion members extending proximate to the support member.

As shown in FIGS. 9A and 9B, the actuation instrument can be incorporated into the frame such that the actuation instrument and the frame are a unitary part. In accordance with another embodiment and in reference to FIG. 9A, an intervertebral implant frame 626 can include a support member 634, a first arm 638 that extends from the support member 634, and a second arm 642 that extends from the support member 634. The first and second arms 638 and 642 are flexible arms and are configured to elastically flex away from each other so that the frame 626 can receive a spacer body 30. The support member 634, the first arm 638, and the second arm 642 are similar to the support member 34, the first arm 38, and the second arm 42 shown in FIG. 3A, and include like structure unless otherwise described.

As shown in FIG. 9A, each of the first and second arms 638 and 642 includes a straight portion 646 and a bent portion 650 that extends from a distal end of the straight portion 646 at angle toward the other of the bent portions 650. Each arm 638 and 642 further includes an expansion member 654 that extends out from the arm at angle. As shown, each expansion member 654 extends out from the proximal end of the bent portion 650 and includes a handle portion 660 that is spaced apart from the straight portion 646. By squeezing the handle portions 660 toward each other, the arms 638 and 642 will elastically flex away from each other so that the frame 626 can receive the spacer body 30. As shown in FIG. 9B, the expansion members 654 can extend proximally such that handle portions 660 are proximal to the arms 638 and 642 to thereby provide more lavage. Once the frame 626 has been coupled to the spacer body 30, the expansion members 654 can be broken off and removed from the frame 626.

In another embodiment the frame can be configured to have portions of the frame arms crimped toward the spacer body to thereby retain the spacer body. In such embodiments, the frame is capable of receiving the spacer body without flexing the arms of the frame away from each other. The spacer body will then be retained by the frame by crimping the arms toward the spacer body to thereby provide a retention force to the spacer body.

Figure 10A:
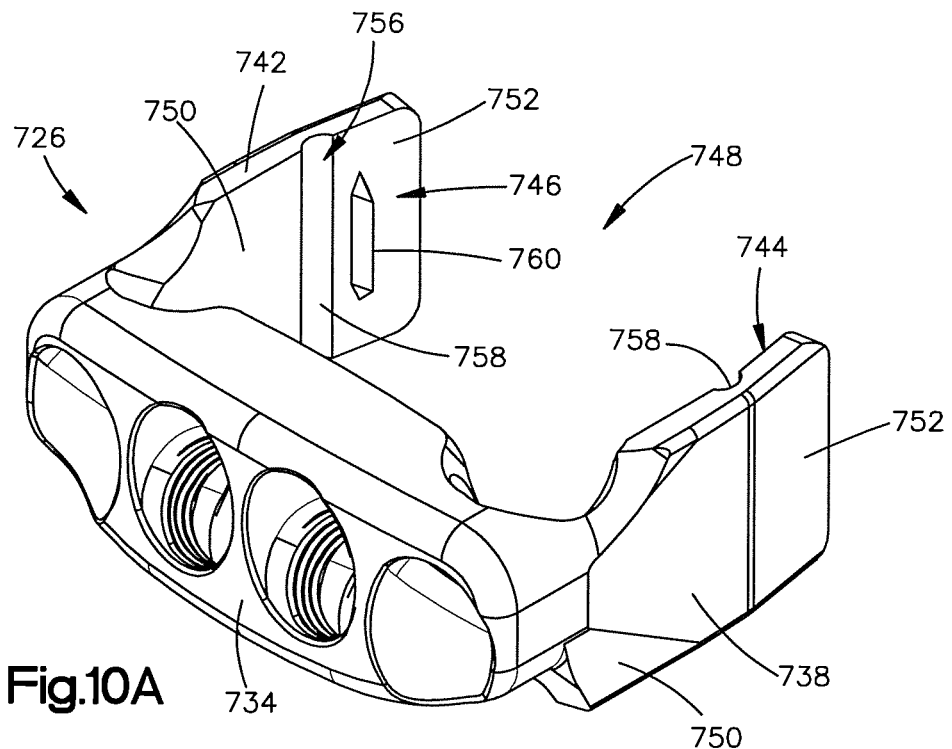
FIG. 10A is a perspective view of an intervertebral implant frame constructed in accordance with another embodiment, the frame including first and second arms that each include a crimp member configured to be crimped against the spacer body to thereby retain the spacer body to the frame.
Figure 10B:
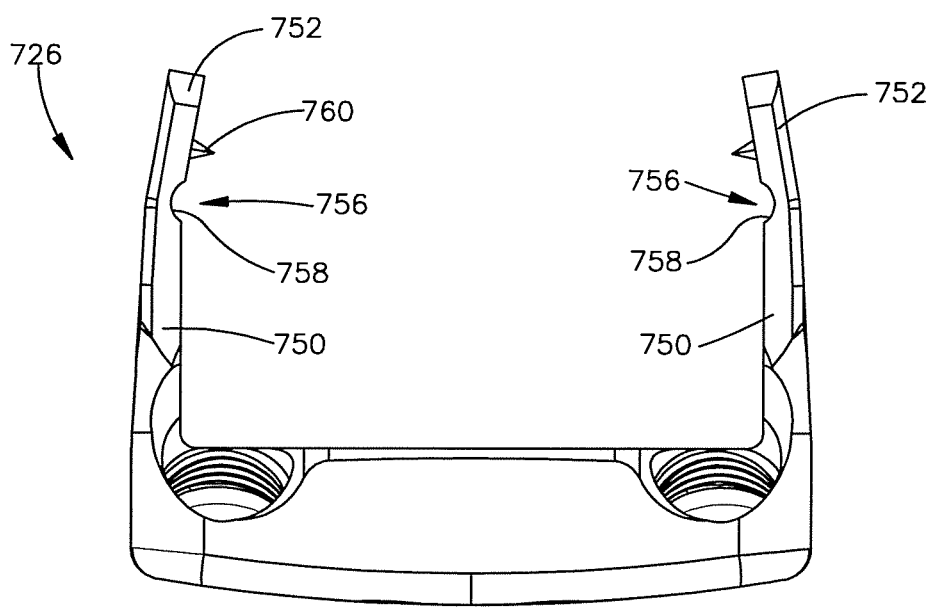
FIG. 10B is a top plan view of the frame shown in FIG. 10A.

For example, in reference to FIGS. 10A and 10B, an intervertebral implant frame 726 includes a support member 734, a first arm 738 that extends from the support member 734, and a second arm 742 that extends from the support member 734. The first and second arms 734 and 738 are crimpable arms such that the frame 726 is configured to have a first initial position in which the spacer body 30 can be disposed between the arms 738 and 742, and a second crimped or engaged position in which the arms 738 and 742 are crimped toward each other to thereby apply a retention force to the spacer body 30. The support member 734, the first arm 738, and the second arm 742 are similar to the support member 34, the first arm 38, and the second arm 42 shown in FIG. 3A, and include like structure unless otherwise described.

The first and second arms 738 and 742 are configured to be crimped rather than flexed. As shown, the arms 738 and 742 include first and second inner spacer contacting surfaces 744 and 746, respectively that are configured to contact and retain the spacer body 30. That is, the inner surface of the support member 734, the first inner spacer contacting surface 744 and the second inner spacer contacting surface 746 together define a void 748 that is configured to receive the spacer body 30. Each arm 738 and 742 further includes a substantially straight portion 750 and a crimp member 752 that extends distally from the straight portion 748. As shown, the crimp members 752 are each coupled to the straight portions 750 by a hinge 756. In the illustrated embodiment, the hinges 756 define transverse bending grooves 758 formed in the inner spacer contacting surfaces 744 and 746.

In operation, the frame 726 can receive the spacer body 30 within the void 748 without expanding the arms 738 and 742 away from each other. Though it should be appreciated some expanding may occur. Once the spacer body 30 is properly positioned, the first crimp member 752 of the first arm 738 can be rotated about the first hinge 756 such that the first crimp member 752 is bent toward the second arm 742. Similarly, the second crimp member 752 of the second arm 742 can be rotated about the second hinge 756 such that the second crimp member 752 is bent toward the first arm 738. After the crimp members 752 have been crimped or otherwise bent, the arms 738 and 742 apply a retention force to the spacer body 30 to thereby retain the spacer body 30 to the frame 726. As shown, each arm 738 and 742 can further include a retention member 760 that extends from the first and second inner spacer contacting surfaces 744 and 746, respectively. The retention members 760 are configured to engage the spacer body 30 to thereby prevent migration of the spacer body 30 from the frame 726.

Figure 11A:
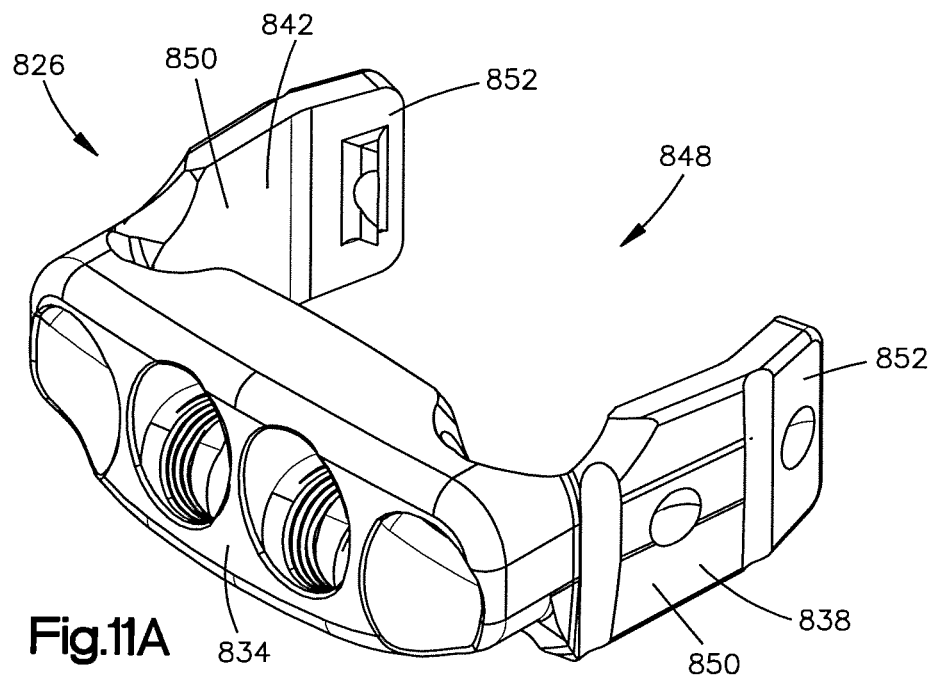
FIG. 11A is a perspective view of an intervertebral implant frame constructed in accordance with another embodiment, the frame including first and second arms that each include a pair of crimp members configured to be crimped against the spacer body to thereby retain the spacer body to the frame.
Figure 11B:
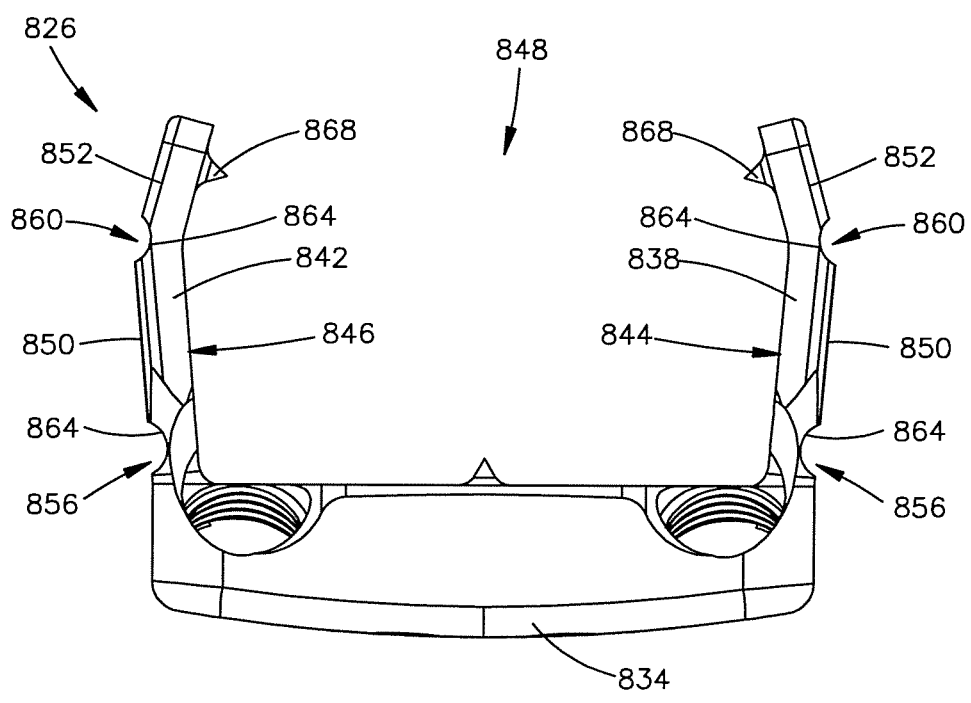
FIG. 11B is a top plan view of the frame shown in FIG. 11A.

In another embodiment and in reference to FIGS. 11A and 11B, an intervertebral implant frame 826 can include more than two crimp members. As shown, the frame 826 includes a support member 834, a first arm 838 that extends from the support member 834, and a second arm 842 that extends from the support member 834. The first and second arms 838 and 842 are crimpable arms such that the frame 826 is configured to have a first initial position in which the spacer body 30 can be disposed between the arms 838 and 842, and a second crimped or engaged position in which the arms 838 and 842 are crimped toward each other to thereby apply a retention force to the spacer body 30. The support member 834, the first arm 838, and the second arm 842 are similar to the support member 34, the first arm 38, and the second arm 42 shown in FIG. 3A, and include like structure unless otherwise described.

The first and second arms 838 and 842 are configured to be crimped rather than flexed. As shown, the arms 838 and 842 include first and second inner spacer contacting surfaces 844 and 846, respectively that are configured to contact and retain the spacer body 30. That is, the inner surface of the support member 834, the first inner spacer contacting surface 844 and the second inner spacer contacting surface 846 together define a void 848 that is configured to receive the spacer body 30. Each arm 838 and 842 further includes a first crimp member 850 and a second crimp member 852 that extends distally from the first crimp member 850. In other words, the first arm 838 can include a first crimp member 850 and a third crimp member 852 of the frame 826, and the second arm 842 can include a second crimp member 850 and a fourth crimp member 852 of the frame 826. As shown, the first crimp member 850 and the second crimp member 850 are each coupled to the support member 834 by first and second hinges 856 respectively. Similarly, the third and fourth crimp members 852 are coupled to the first crimp members 850 by third and fourth hinges 860 respectively. In the illustrated embodiment, the hinges 856 and 860 define transverse bending grooves 864 formed in the outer surfaces of the first and second arms 838 and 842.

In operation, the frame 826 can receive the spacer body 30 within the void 848 without expanding the arms 838 and 842 away from each other. Though it should be appreciated some expanding may occur. Once the spacer body 30 is properly positioned, the first crimp member 850 and the second crimp member 852 of the first arm 838 can be rotated about the first and second hinges 856 and 860 respectively such that the crimp members 850 and 852 are bent toward the second arm 842. Similarly, the first crimp member 850 and the second crimp member 852 of the second arm 842 can be rotated about the first and second hinges 856 and 860 respectively such that the crimp members 850 and 852 are bent toward the first arm 838. After the crimp members 850 and 852 have been bent, the arms 838 and 842 apply a retention force to the spacer body 30 to thereby retain the spacer body 30 to the frame 826. As shown, each arm 838 and 842 can further include a retention member 868 that extends from the first and second inner spacer contacting surfaces 844 and 846, respectively. The retention members 868 are configured to engage the spacer body 30 to thereby prevent migration of the spacer body 30 from the frame 826.

Figure 12A:
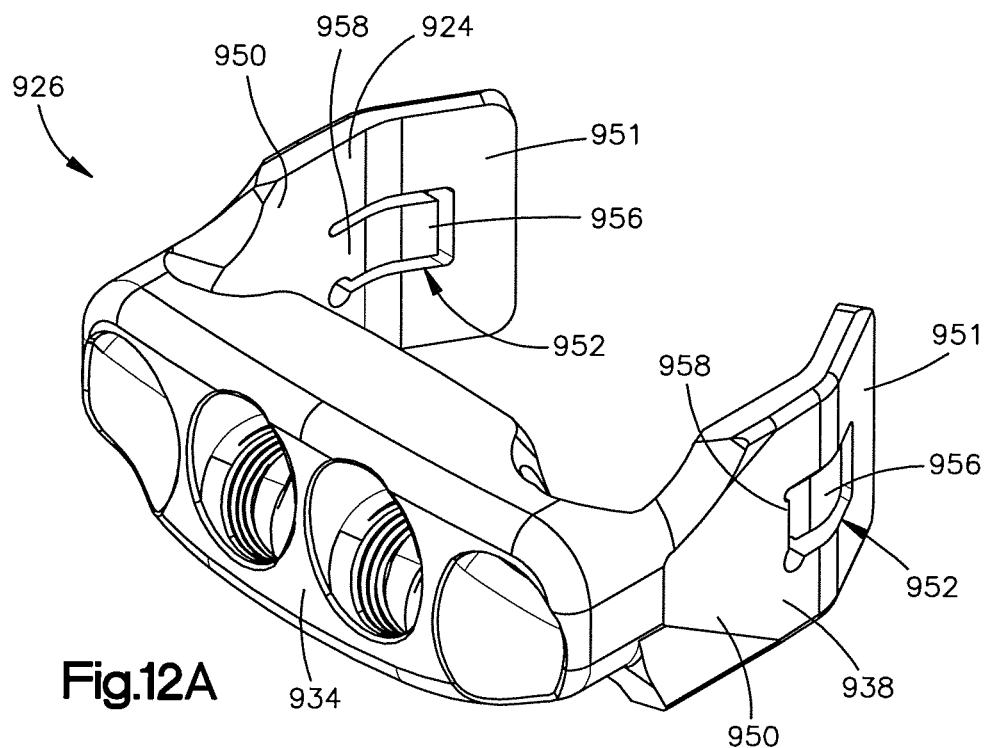
FIG. 12A is a perspective view of an intervertebral implant frame constructed in accordance with another embodiment, the frame including first and second arms that each include a crimp member configured as a crimp tab disposed within a window defined by the arm.
Figure 12B:
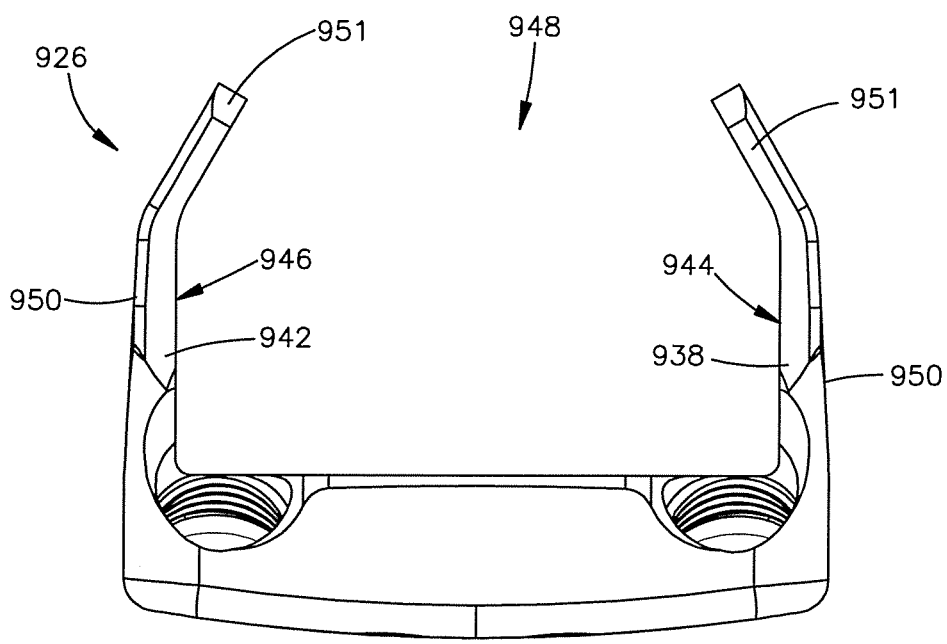
FIG. 12B is a top plan view of the frame shown in FIG. 12A.

In another embodiment and in reference to FIGS. 12A and 12B, an intervertebral implant frame 926 can include crimp members that define crimping tabs. As shown, the frame 926 includes a support member 934, a first arm 938 that extends from the support member 934, and a second arm 942 that extends from the support member 934. The first and second arms 938 and 942 are crimpable arms such that the frame 926 is configured to have a first initial position in which the spacer body 30 can be disposed between the arms 938 and 942, and a second crimped or engaged position in which the arms 938 and 942 are crimped toward each other to thereby apply a retention force to the spacer body 30. The support member 934, the first arm 938, and the second arm 942 are similar to the support member 34, the first arm 38, and the second arm 42 shown in FIG. 3A, and include like structure unless otherwise described.

The first and second arms 938 and 942 are configured to be crimped rather than flexed. As shown, the arms 938 and 942 include first and second inner spacer contacting surfaces 944 and 946, respectively that are configured to contact and retain the spacer body 30. That is, the inner surface of the support member 934, the first inner spacer contacting surface 944 and the second inner spacer contacting surface 946 together define a void 948 that is configured to receive the spacer body 30. Each arm 938 and 942 further includes a substantially straight portion 950, a bent portion 951 extending from a distal end of the straight portion 950, and a crimp member 952 that is formed in the straight and bent portion 950 and 951. As shown, the crimp members 952 each define a crimping tab 956 that is attached to one of the straight portion 950 or the bent portion 951 by a hinge 958. In the illustrated embodiment, a proximal edge of the crimping tab 956 is coupled to the straight portion 950 and defines the hinge 958. It should be appreciated, however, that an upper edge, a lower edge, or a distal edge of the crimping tabs 956 could define the hinges 958. As shown, each crimping tab 956 is disposed within a window defined by the respective arm.

In operation, the frame 926 can receive the spacer body 30 within the void 948 without expanding the arms 938 and 942 away from each other. Though it should be appreciated some expanding may occur. Once the spacer body 30 is properly positioned, the crimping tab 956 of the first arm 938 can be rotated about the hinge 958 such that the crimping tab 956 is bent toward the second arm 942. Similarly, the crimping tab 956 of the second arm 942 can be rotated about the hinge 958 such that the crimping tab 956 is bent toward the first arm 938. After the crimping tabs 956 have been bent, the frame is in the crimped or engaged position such that the arms 938 and 942 apply a retention force to the spacer body 30 to thereby retain the spacer body 30 to the frame 926. It should be appreciated that the first and second arms 938 and 942 can include any number of crimping tabs 956 as desired.

Figure 13A:
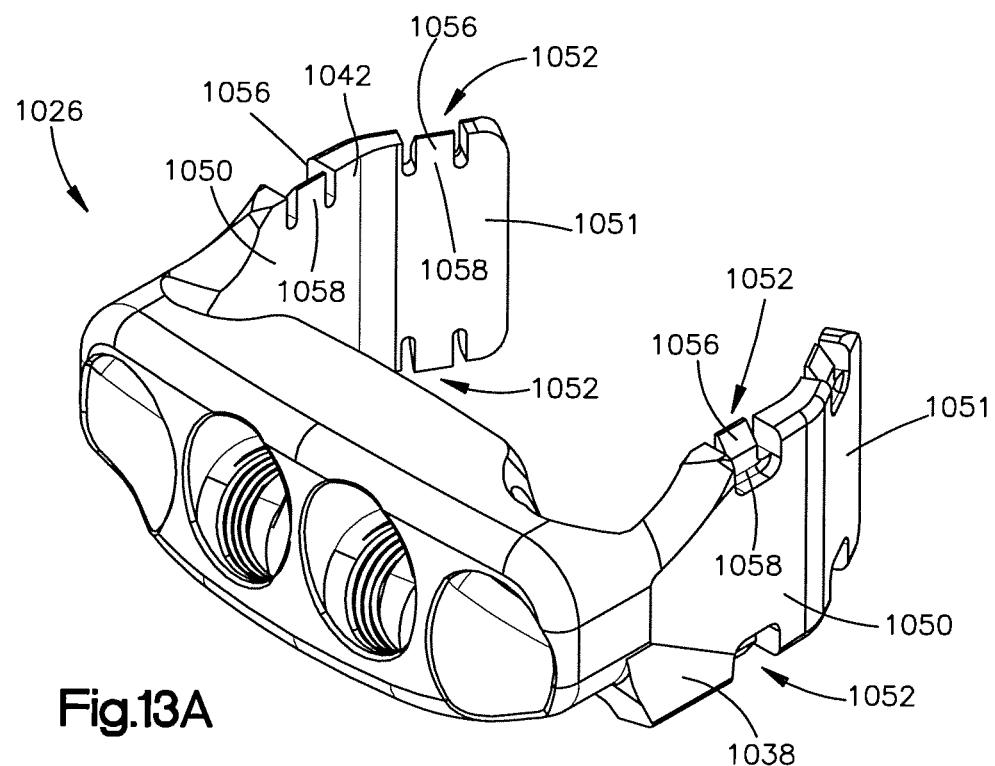
FIG. 13A is a perspective view of an intervertebral implant frame constructed in accordance with another embodiment, the frame including first and second arms that each include at least one crimp member configured as a crimp tab.
Figure 13B:
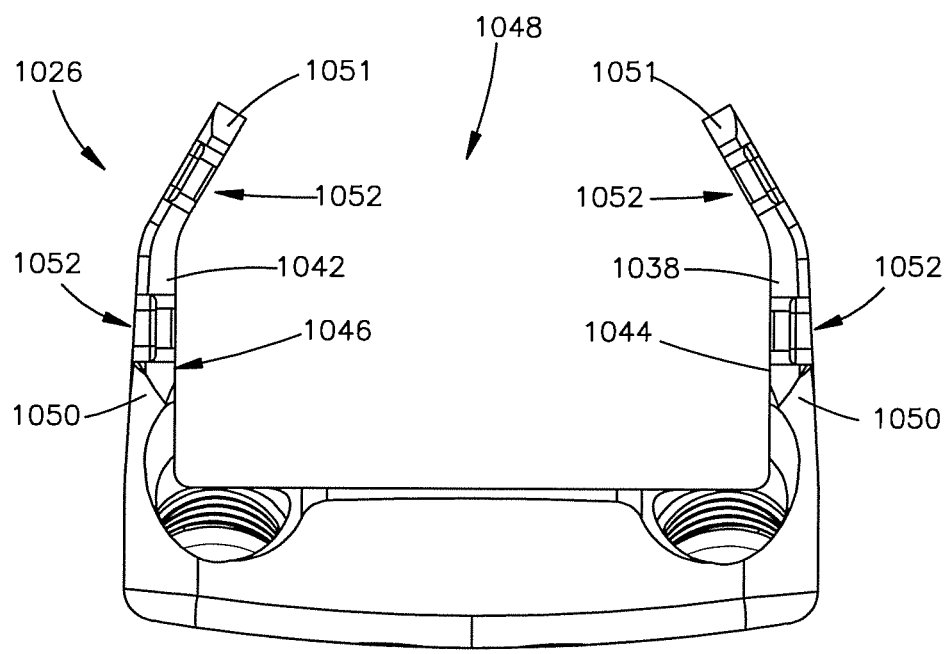
FIG. 13B is a top plan view of the frame shown in FIG. 13A.

In another embodiment and in reference to FIGS. 13A and 13B, an intervertebral implant frame 1026 can include crimp members that define tabs disposed along upper and lower edges of the arms. As shown, the frame 1026 includes a support member 1034, a first arm 1038 that extends from the support member 1034, and a second arm 1042 that extends from the support member 1034. The first and second arms 1034 and 1038 are crimpable arms such that the frame 1026 is configured to have a first initial position in which the spacer body 30 can be disposed between the arms 1038 and 1042, and a second crimped or engaged position in which the arms 1038 and 1042 are crimped toward each other to thereby apply a retention force to the spacer body 30. The support member 1034, the first arm 1038, and the second arm 1042 are similar to the support member 34, the first arm 38, and the second arm 42 shown in FIG. 3A, and include like structure unless otherwise described.

The first and second arms 1038 and 1042 are configured to be crimped rather than flexed. As shown, the arms 1038 and 1042 include first and second inner spacer contacting surfaces 1044 and 1046, respectively that are configured to contact and retain the spacer body 30. That is, the inner surface of the support member 1034, the first inner spacer contacting surface 1044 and the second inner spacer contacting surface 1046 together define a void 1048 that is configured to receive the spacer body 30. Each arm 1038 and 1042 further includes a substantially straight portion 1050, a bent portion 1051 extending from a distal end of the straight portion 1050, and at least one, such as a plurality of crimp members 1052 that are formed in upper and lower edges of the arms 1038 and 1042. As shown, the crimp members 1052 each define a crimping tab 1056 that are each attached to the straight and bent portions 1050 and 1051 by respective horizontal hinges 1058.

In operation, the frame 1026 can receive the spacer body 30 within the void 1048 without expanding the arms 1038 and 1042 away from each other. Though it should be appreciated some expanding may occur. Once the spacer body 30 is properly positioned, the crimping tabs 1056 of the first arm 1038 can be rotated about the hinges 1058 such that the crimping tabs 1056 are bent toward the second arm 1042. Similarly, the crimping tabs 1056 of the second arm 1042 can be rotated about the hinges 1058 such that the crimping tabs 1056 are bent toward the first arm 1038. After the crimping tabs 1056 have been bent, the frame 1026 is in the crimped or engaged position such that the arms 1038 and 1042 apply a retention force to the spacer body 30 to thereby retain the spacer body 30 to the frame 1026. It should be appreciated that the first and second arms 1038 and 1042 can include any number of crimping tabs 1056 as desired.

Figures 14A, 14B:
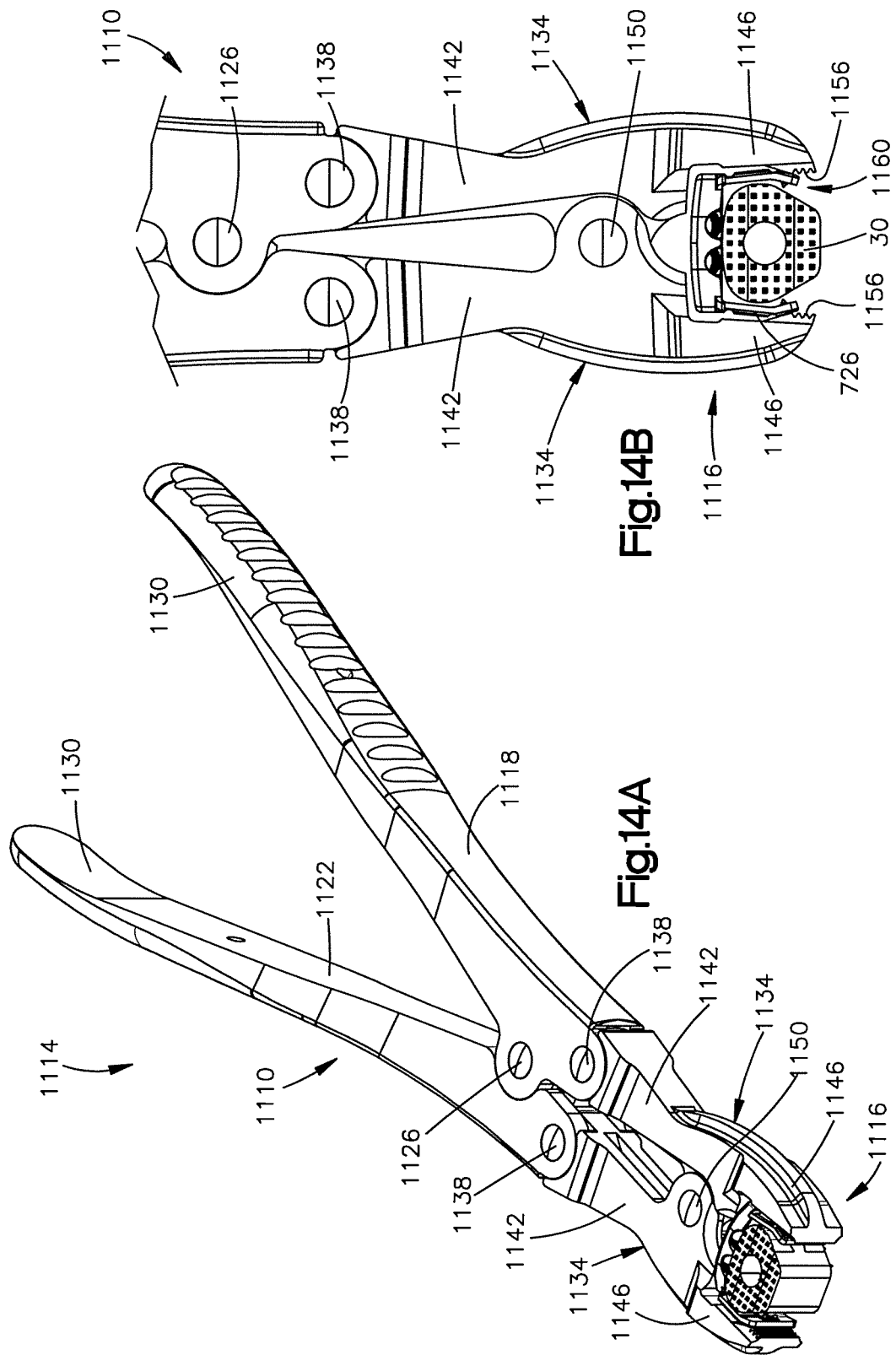
FIG. 14A is a perspective view of an actuation instrument configured as a crimping instrument constructed in accordance with an embodiment, the instrument including gripping members that are configured to crimp the crimp members of the frames shown in FIGS. 10A and 11A.
FIG. 14B is a detailed top plan view of the gripping members of the instrument shown in FIG. 14A, and an intervertebral implant disposed between the gripping members.

As shown in FIGS. 14A-14C, the spacer body 30 can be coupled to the frame 726 using an actuation instrument 1110 that is configured as a crimping instrument. The instrument 1110 and the frame 726 can together define an intervertebral implant system 1114. The crimping instrument 1110 includes an actuation grip 1116 that is configured as a crimping grip so as to apply a crimping force to the frame 726. For instance, in accordance with the illustrated embodiment, the crimping grip 1116 is configured to apply first and second crimping forces to the crimp members 752 of the first and second arms 738 and 742. The first and second crimping forces will permanently deform the crimp members 752 of the frame 726 to thereby retain the spacer body 30 to the frame 726. Therefore, the instrument 1110 is configured to have a first position or configuration whereby the instrument receives the frame 726, and a second position or configuration whereby the instrument applies a crimping force to the frame 726. It should be appreciated that the instrument 1110 can also be used to crimp the frame 726 to the spacer body.

As shown in FIGS. 14A and 14B, the instrument 1110 includes a first arm 1118 and a second arm 1122 rotatably coupled to the first arm 1118 at a first pivot 1126. The first and second arms 1118 and 1122 are configured as crimping arms and each includes a handle portion 1130 that extends proximally of the first pivot 1126 and a gripping portion 1134 that extends distally of the first pivot 1126. The handle portions 1130 are configured to be gripped by an individual and moved toward each other to thereby crimp the frame 726 to the spacer body 30.

As shown in FIGS. 14A and 14B, the gripping portions 1134 are coupled to the handle portions 1130 at respective second pivots 1138 that are distal to the first pivot 1126. As shown in FIG. 14B, each gripping portion 1134 includes an extension member 1142 that extends from the second pivot 1138, and a gripping member 1146 that extends distally from a distal end of the extension member 1142. As shown, the gripping portions 1134 are coupled to each other at a third pivot 1150 that proximate to the distal ends of the extension members 1142, such that the gripping members 1146 extend distally to the third pivot 1150. Therefore, when the handle portions 1130 are moved toward each other so as to rotate about the first pivot 1126, the extension members 1142 will rotate about their respective second pivots 1138 such that they move away from each other, and the gripping members 1146 will rotate about the third pivot 1150 such that they move toward each other to thereby crimp the frame 726 on to the spacer body 30.

As shown in FIG. 14B, each gripping member 1146 defines a ribbed contact surface 1156 that is configured to contact and apply a crimping force to the crimp members 752 of the frame 726. As shown, the contact surfaces 1156 are spaced apart from each other so as to define a void 1160 that is configured to receive the frame 726 and spacer body 30. Each gripping member 1146 may further define a lower platform that is configured to support the frame 726 and spacer body 30 while the instrument 1110 is crimping the frame 726 to the spacer body 30. The ribs of the contact surfaces 1156 are configured to allow a portion of the frame 26 between the gripping members 1146.

In operation and in reference to FIG. 14C, the void 1160 defined between the contact surfaces 1156 receives the frame 726 and spacer body 30 such that the spacer body 30 is loosely disposed within the frame 726. By squeezing the handle portions 1130 toward each other, the contact surfaces 1156 will apply respective crimping forces to the crimp members 752 of the frame 726. Once a sufficient amount of force has been applied, the crimp members 752 will permanently deform toward each other such that the frame 726 will move to the crimped or engaged position and will provide a retention force against the spacer body 30 and retain the spacer body 30 to the frame 726. As shown, when in the crimped or engaged position, respective portions of the arms 738 and 742 are spaced apart from each other by the second distance $d_2$ which is less than the first distance.

In another embodiment and in reference to FIG. 14D, the instrument 1110 can also be configured to bend the crimp members 952 of the frame 926. As shown, the instrument 1110 can include beaked protrusions 1170 that are defined by the gripping members 1146 and are configured to engage the crimp members 952 when the handle portions 1130 are squeezed together. The beaked protrusions 1170 can be anywhere along the gripping members 1146 so long as they align with the crimp members 952. Moreover, the gripping members 1146 can define any number of beaked protrusions 1170, as desired. Therefore, if the frame 926 includes four crimping tabs 956 (i.e. crimp members 952) then the gripping members 1146 can each define two beaked protrusions 1170 that align with the crimping tabs 956.

Figure 15A:
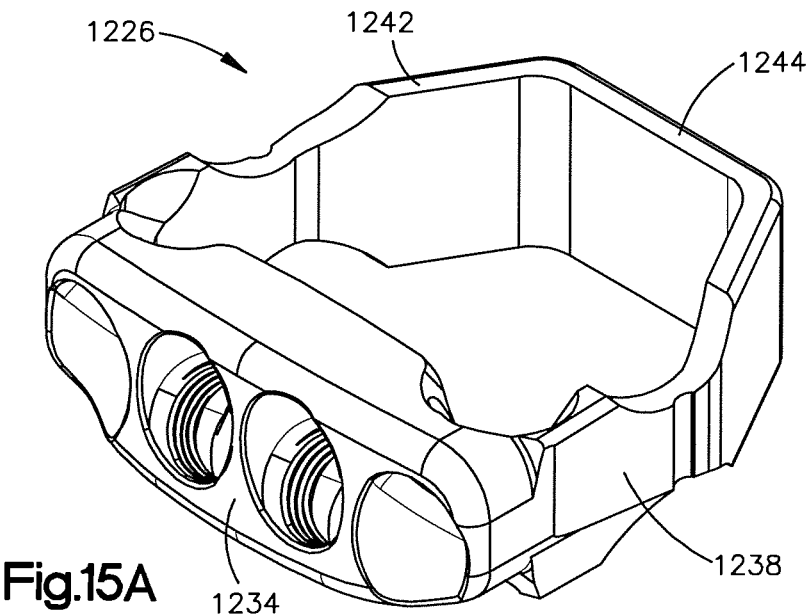
FIG. 15A is a perspective view of an intervertebral implant frame constructed in accordance with another embodiment, the frame defining a four walled structure.
Figure 15B:
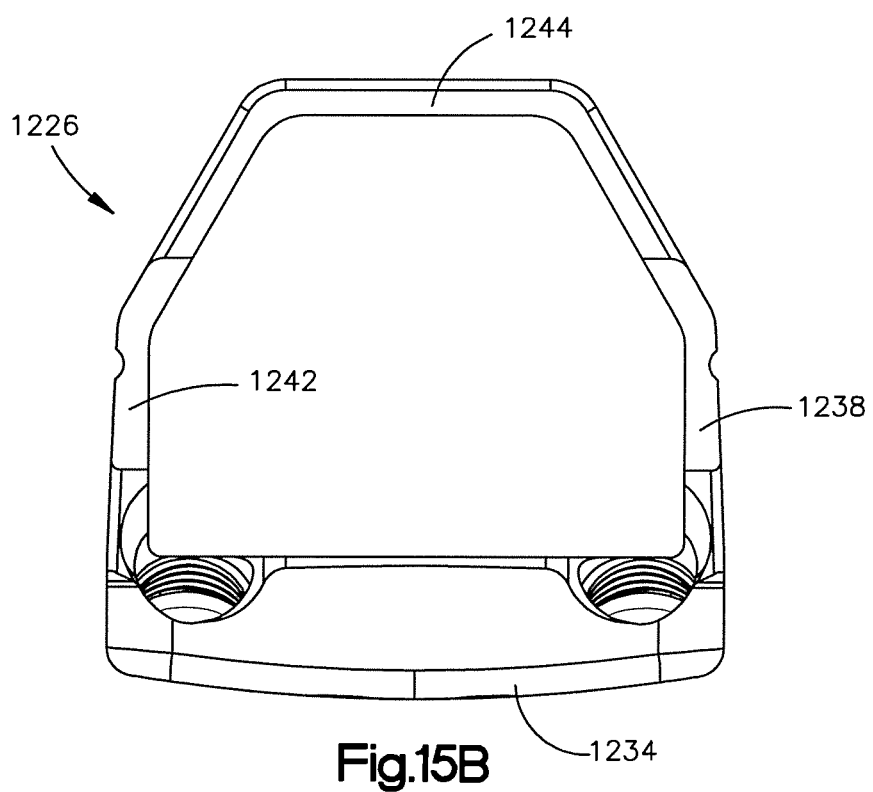
FIG. 15B is a top plan view of the frame shown in FIG. 15A.

In another embodiment and in reference to FIGS. 15A and 15B frame may include a fully enclosed endplate that supports the spacer body with a multi-walled, such as a six walled structure. As shown, an intervertebral implant frame 1226 includes a support member 1234, a first arm 1238 that extends from the support member 1234, a second arm 1242 that extends from the support member 1234, and an end plate 1244 that connects the distal ends of the first and second arms 1238 and 1242 together. The support member 1234, the first arm 1238, the second arm 1242, and the end plate 1244 together define a six wall structure that supports the spacer body 30.

Now in reference to FIGS. 16A-16E, the spacer body 30 can be pre-drilled to make channels in the spacer body 30 using a spacer body drill guide 1300. The channels are configured to provide clearance for the fixation elements 62 when the intervertebral implant is affixed to the superior and inferior vertebral bodies. Therefore, when the fixation elements are inserted into the fixation element apertures of the frame and then subsequently affixed to the vertebral bodies, the fixation elements will not be interfered with by the spacer body 30. The channels can be made either before or after the spacer body has been retained by the frame. If the channels are made prior to the spacer body being retained by the frame, then the channels can have a dimension that is greater than a dimension of the fixation element receiving apertures of the frame.

Figure 16A:
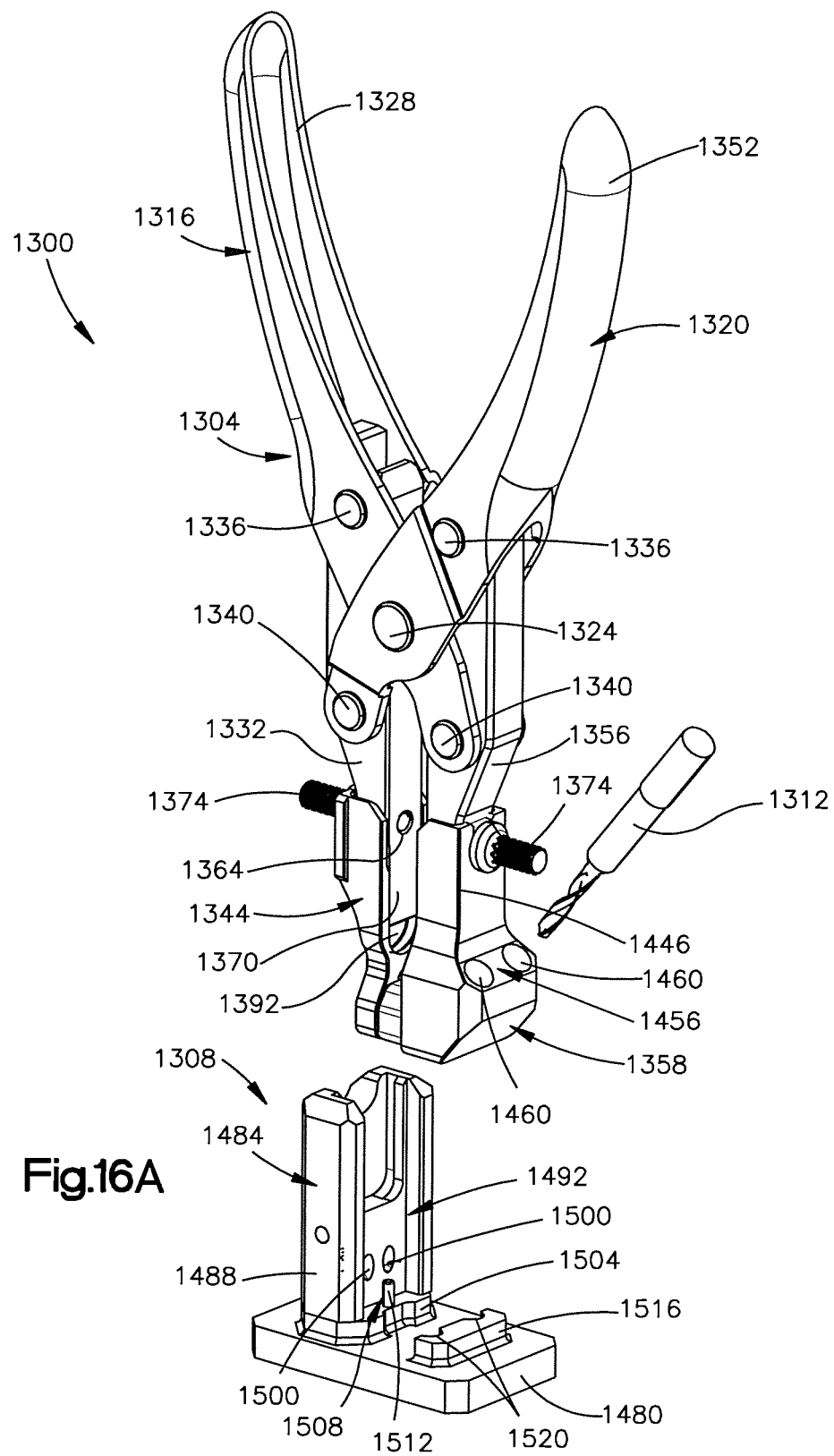
FIG. 16A is a perspective view of a spacer body drill guide constructed in accordance with an embodiment, the drill guide including a clamp, and a cradle that is configured to mate with and support the clamp.

As shown in FIGS. 16A and 16B, the spacer body drill guide 1300 includes a clamp 1304 configured to hold the spacer body 30, and a cradle 1308 that is configured to support the clamp 1304 while the channels are drilled using a drill bit 1312. The clamp 1304 includes a first clamp arm assembly 1316 and a second clamp arm assembly 1320 that is rotatably coupled to the first clamp arm assembly 1316 at a first pivot 1324. The first clamp arm assembly 1316 includes a first handle 1328, a first extension member 1332, and a first jaw 1344 removeably coupled to the first extension member 1332. Similarly, the second clamp arm assembly 1320 includes a second handle 1352, a second extension member 1356, and a second jaw 1358 removeably coupled to the second extension member 1356. As shown, a proximal end of the first extension member 1332 is coupled to a middle portion of the first handle 1328 at a respective second pivot 1336, and a middle portion of the first extension member 1332 is coupled to a distal end of the second handle 1352 at the third pivot 1340. Similarly, a proximal end of the second extension member 1356 is coupled to a middle portion of the second handle 1352 at a respective second pivot 1336, and a middle portion of the second extension member 1356 is coupled to a distal end of the first handle 1352 at a respective third pivot 1340.

The first and second extension members 1332 and 1356 are substantially parallel to each other and remain substantially parallel to each other as the first and second handles 1328 and 1352 are rotated about the first pivot 1324. This allows the first and second jaws 1344 and 1358 to translate rather than rotate relative to each other as the first and second handles 1328 and 1352 are rotated about the first pivot 1324. As shown in FIGS. 16A and 16B, each extension member 1332 and 1356 includes an elongate mounting portion 1370 at its distal end. Each mounting portion 1370 defines a fixation element receiving aperture 1364 that is configured to receive a respective fixation element 1374. As shown, the first and second jaws 1344 and 1358 are configured to be mounted to the removeably mounting portions 1370 with the fixation elements 1374.

As shown in FIGS. 16A and 16B, the first jaw 1344 includes an elongate body 1380 that has a proximal mounting portion 1384 and a distal gripping portion 1388. The mounting portion 1384 defines an elongate channel 1392 that is configured to receive the mounting portion 1370 of the first extension member 1332. The mounting portion 1384 further defines an outer slot or aperture 1396 that extends into the channel 1392 and is configured to receive the fixation element 1374 to thereby couple the first jaw 1344 to the first extension member 1332. The mounting portion 1384 further includes an engagement rail 1397 that is configured to engage the cradle 1308 when the clamp 1304 is mounted to the cradle 1308.

As shown in FIGS. 16A and 16B, the gripping portion 1388 includes an inner spacer contacting surface 1402, an outer surface 1406 and at least one such as two, guide holes 1410 that extend from the outer surface 1406 through to the inner spacer contacting surface 1402 at a downward angle. The guide holes 1410 are configured to receive the drill bit 1312 and guide the drill bit 1312 to the spacer body 30. As shown, a lower portion of the inner spacer contacting surface 1402 defines a pair of cut outs 1412 that provide clearance for the drill bit 1312 as it extends thought the holes 1410.

As shown in FIG. 16B, the gripping portion 1388 can further include a mating member 1414, such as a bore 1418 that extends into the gripping portion 1388. The bore 1418 is configured to receive a mating member of the cradle 1308 to thereby properly align the clamp within the cradle. It should be appreciated that the mating member 1414 can have other configurations as desired. For example, the mating member 1414 can define a peg or protrusion.

As shown in FIGS. 16A and 16B, the second jaw 1358 includes an elongate body 1430 that has a proximal mounting portion 1434 and a distal gripping portion 1438. The mounting portion 1434 defines an elongate channel 1442 that is configured to receive the mounting portion 1370 of the first extension member 1332. The mounting portion 1434 further defines an outer slot or aperture 1446 that extends into the channel 1442 and is configured to receive the fixation element 1374 to thereby couple the second jaw 1358 to the second extension member 1356.

As shown in FIGS. 6A and 6B, the gripping portion 1438 includes an inner spacer contacting surface 1452, an outer surface 1456 and at least one such as two, guide holes 1460 that extend from the outer surface 1456 through to the inner spacer contacting surface 1452 at a downward angle. The guide holes 1460 are configured to receive the drill bit 1312 and guide the drill bit 1312 to the spacer body 30. As shown, a lower portion of the inner spacer contacting surface 1402 defines a pair of cut outs 1462 that provide clearance for the drill bit 1312 as it extends thought the holes 1460.

As shown in FIG. 16B, each gripping portion 1388 and 1438 can further include a plurality of retention members 1470 that extend out from the inner spacer contacting surfaces 1402 and 1452. In the illustrated embodiment the retention members 1470 define spikes that are configured to engage the spacer body 30. It should be appreciated, however, that the retention members 1470 can include other configuration, or the gripping portions 1388 and 1438 can be void of retention members 1470.

As shown in FIG. 16A, the cradle 1308 includes a base 1480 and a mounting portion 1484 that extends up from the base 1480. The base 1480 is sized and configured to sit on a surface and support the clamp 1304 while the drill bit 1312 drills the channels into the spacer body 30. The mounting portion 1484 includes a transverse elongate body 1488 and a channel 1492 that extends transversely into the body 1488. The channel 1492 is configured to receive the first jaw 1344 along a transverse direction such that when the first jaw 1344 is received by the channel 1492 the first jaw 1344 is fully supported by the cradle 1308.

The mounting portion 1484 further includes a pair of drill guide apertures 1500 that extend through body 1488 and into the channel 1492. The drill guide apertures 1500 of the mounting portion 1484 are configured to align with the drill guide apertures 1410 of the first jaw 1344 when the first jaw 1344 is received by the channel 1492. The mounting portion 1484 further includes a first platform 1504 that a distal end of the channel 1492 terminates into, and a mating member 1508 that is defined by the first platform 1504. In the illustrated embodiment, the mating member 1508 is a peg 1512 that is configured to mate with the bore 1418 of the first jaw 1344. It should be appreciated, however, that the mating member 1508 can have other configurations as desired so long as the mating members of the mounting portion 1484 and the first jaw 1344 can mate with each other.

As shown in FIG. 16A, the cradle 1308 further includes a second platform 1516 that extends from the base 1480 and is spaced apart from the first platform 1504. The second platform 1516 defines a pair of cutouts 1520 that align with the drill guide apertures 1460 of the second jaw 1358 when the second jaw 1358 is resting on the second platform 1516.

In operation and in reference to FIGS. 16C-16F, the clamp 1304 is configured to hold a spacer body 30 by moving the handle portions 1328 and 1352 toward each other. The clamp 1304 is then translated toward the cradle 1308 subsequently along the transverse direction T such that the first jaw 1344 of the clamp 1304 is mounted within the channel 1492 of the cradle 1408. When mounted and as shown in FIG. 16D, the peg 1512 engages the bore 1418, and the first and second jaws 1344 and 1358 rest on the first and second platforms 1504 and 1516 respectively, such that the drill guide apertures 1410 of the first jaw 1344 are aligned with the drill guide apertures 1500 of the cradle 1308.

Figure 16F:
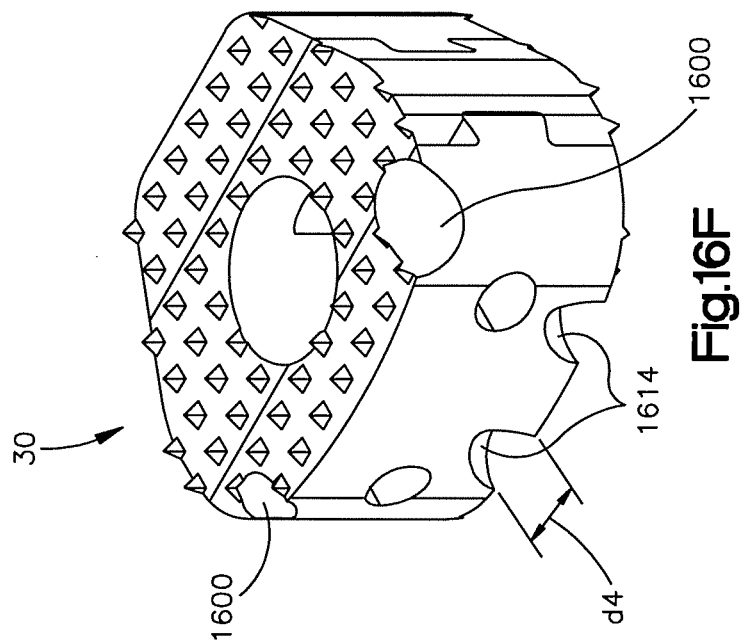
FIG. 16F is a perspective view of a spacer body after the clearance channels have been formed using the drill guide shown in FIG. 16A.
Figure 16E:
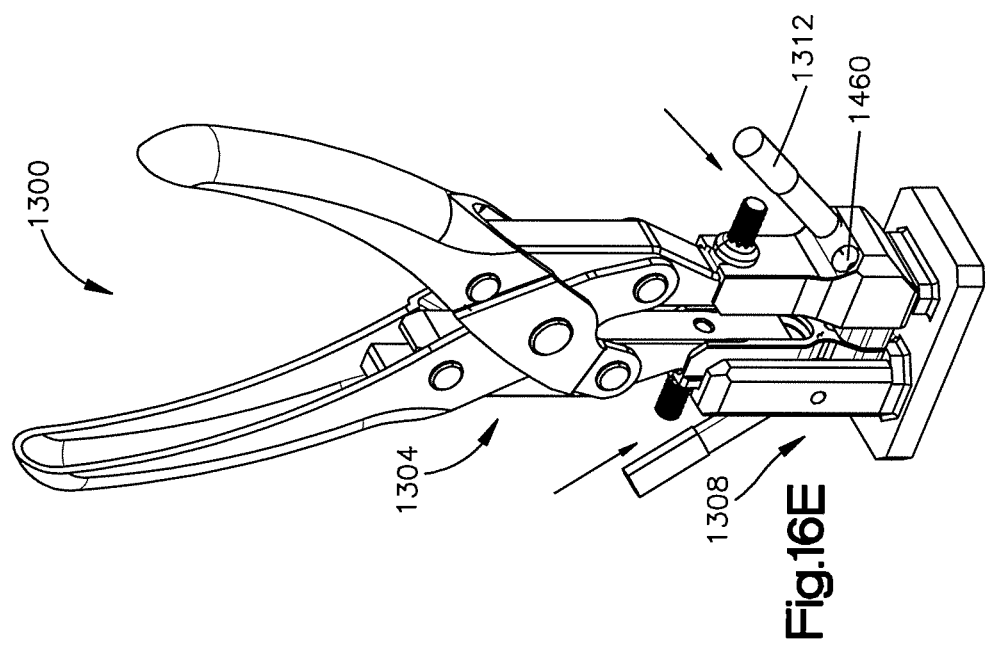
FIG. 16E is a perspective view of a drill bit being inserted into drill guide apertures defined by the clamp to thereby form clearance channels in the spacer body.

As shown in FIG. 16E, the drill bit 1312 may then be inserted into the drill guide apertures 1410 and 1460 to thereby form the channels in the spacer body 30. As shown in FIG. 16F, the spacer body 30 will have two upper channels 1600, and two lower channels 1614. After the channels have been formed, the spacer body 30 may be coupled to a frame such as one of the frames described, using any of the instruments described. When the spacer body 30 is retained by the frame the fixation element receiving apertures of the frame will align with the channels 1600 and 1614 of the spacer body 30. The channels 1600 and 1614 can have a dimension have a dimension such as a diameter $d_4$ that is greater than the diameter of the fixation element receiving apertures of the frame. It should be appreciated, however, that the diameter $d_5$ can be equal to or even less than the diameter of the fixation element receiving apertures of the frame, as desired.

It should be appreciated, that the drill guide 1300 can be part of a kit that also includes at least one of an intervertebral implant frame, an actuation instrument, and a drill bit. Moreover is should be appreciated, that the kit can also include the spacer body 30 and at least one fixation element 62.

In another embodiment and in reference to FIGS. 17A-17F, an intervertebral implant 1622 can include an intervertebral implant frame that is configured to be inserted into the intervertebral space such that a portion of the frame abuts an anterior surface 14a of the first vertebral body 10a and a portion of the anterior surface 14a is substantially flush with or extends beyond a front face of the frame. The intervertebral implant 1622 includes similar structure as the intervertebral implant 22 shown in FIGS. 2A-3E and is configured to operate in a similar manner unless otherwise described. For example, the intervertebral implant 1622 includes an intervertebral implant frame 1626 and a spacer body 1630 that is retained by the frame 1626.

As shown in FIGS. 17C-17F the frame 1626 includes a support member 1634, a first arm 1638 that extends from the support member 1634, and a second arm 1642 that extends from the support member 1634. In the illustrated embodiment, the first and second arms 1638 and 1642 are flexible arms that extend from opposed ends of the support member 1634 such that the support member 1634, the first arm 1638, and the second arm 1642 together create a three wall structure that retains and secures the spacer body 1630 to the frame 1626.

Figure 17A:
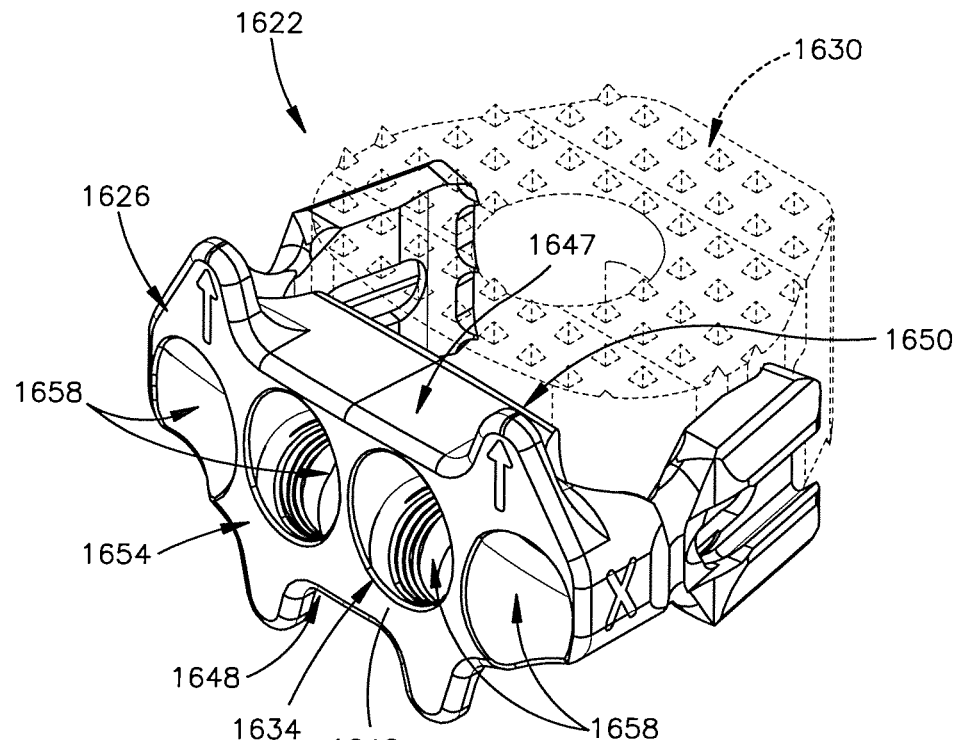
FIG. 17A is a perspective view of an intervertebral implant constructed in accordance with another embodiment, the intervertebral implant having an intervertebral implant frame and a spacer body retained by the intervertebral implant frame.
Figure 17B:
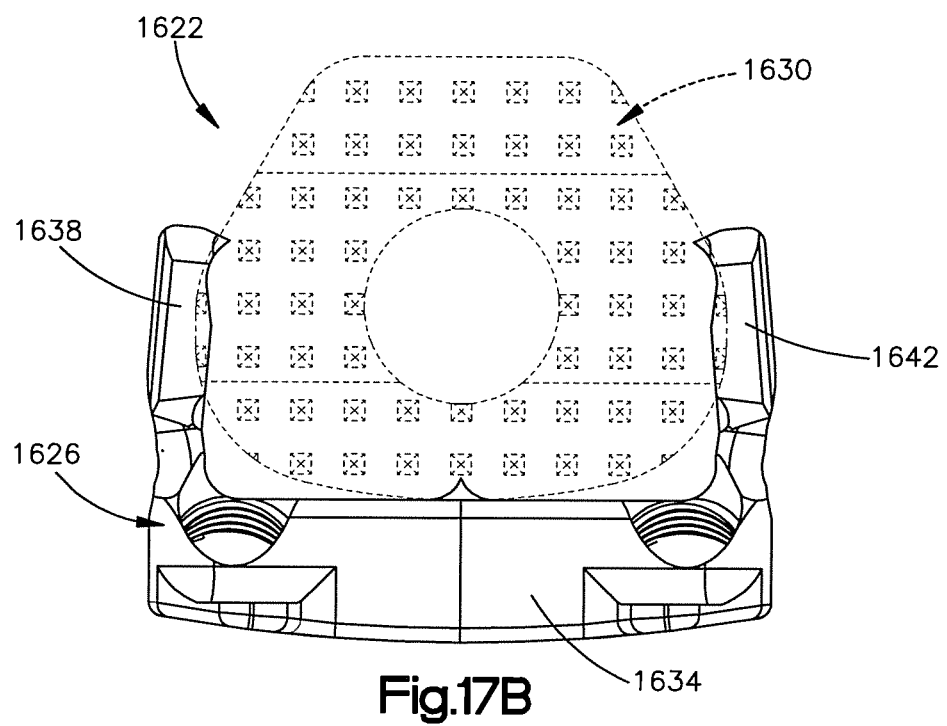
FIG. 17B is a top plan view of the intervertebral implant shown in FIG. 17A.
Figure 17C:
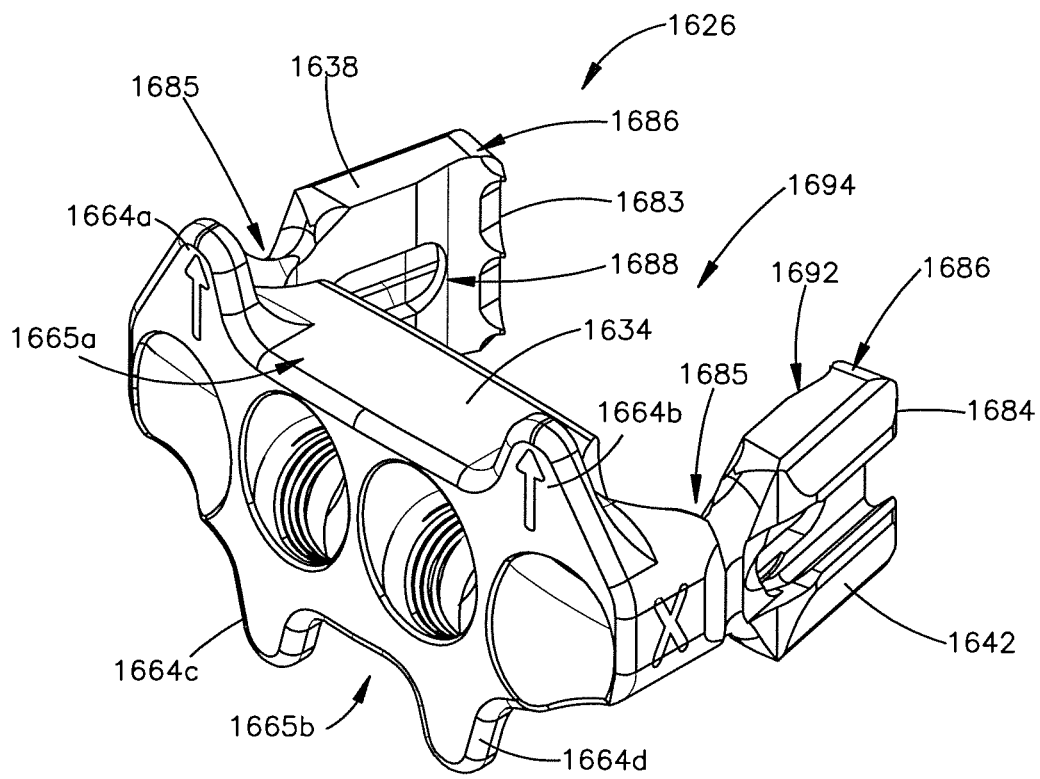
FIG. 17C is a perspective view of the intervertebral implant frame shown in FIG. 17A, the intervertebral implant frame having a support member, a first arm extending from the support member, and a second arm extending from the support member, the support member including tabs that are spaced from each other such that the frame provides a zero profile when the first and second arms are inserted into an intervertebral space.
Figure 17D:
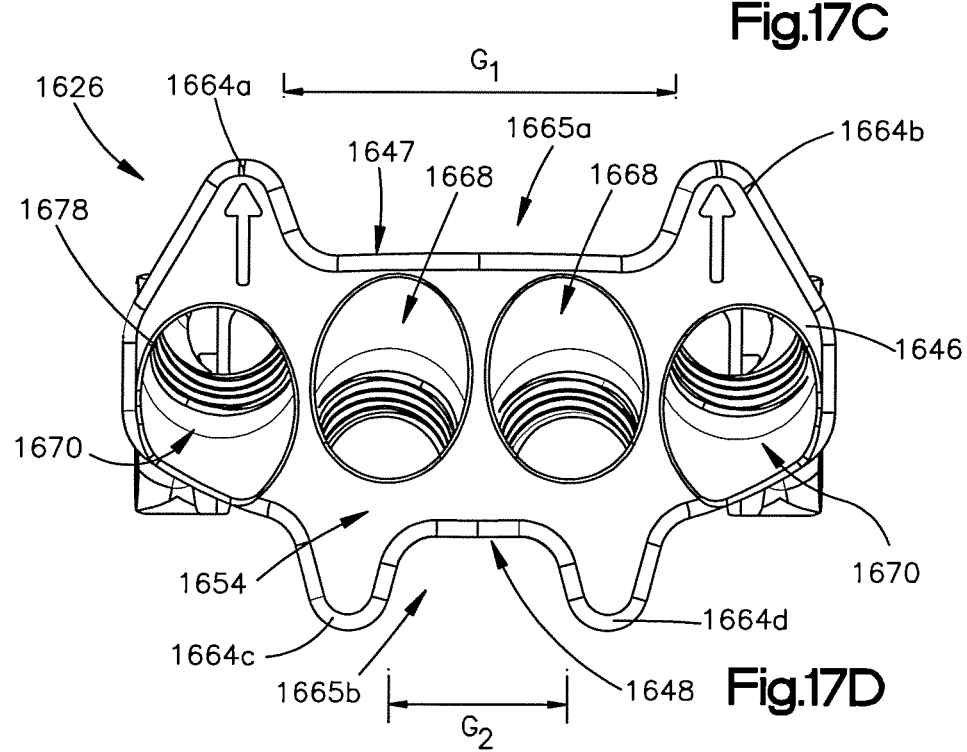
FIG. 17D is a front elevation view of the intervertebral implant frame shown in FIG. 17C.

As shown in FIGS. 17C-17F, the support member 1634 includes a body 1646 that defines a first vertebral body facing surface 1647, a second vertebral body facing surface 1648 that is spaced from the first vertebral body 1647 facing surface along a first direction, an inner face or surface 1650, and an outer or front face or surface 1654 that is spaced from the inner face along a second direction that is substantially perpendicular to the first direction. The first and second vertebral body facing surfaces 1647 and 1648 can be configured to at least partially abut the first and second vertebral bodies when the implant is implanted into the intervertebral space. It should be appreciated, however, that a portion of or the entirety of the first and second vertebral body facing surfaces 1647 and 1648 can be external to the intervertebral space when the implant is implanted into the intervertebral space. It should be further appreciated, that the spacer body 1630 can have a height that is greater than that of the arms such that first and second vertebral body facing surfaces 1746 and 1648 are spaced from the first and second vertebral bodies when the implant is implanted into the intervertebral space. As shown in FIG. 17D, the body 1646 can further define at least one, such as two or such as four, fixation element receiving apertures 1658 that extend through the body 1646 from the front surface 1654 to the inner surface 1650. Each fixation element receiving aperture 1658 is configured to receive a respective fixation element, such as fixation element 62 shown in FIGS. 4A and 4B.

As shown in FIG. 17D, two of the fixation element receiving apertures 1658 are inner apertures 1668 that extend through the body 1646 at a downward angle relative to the insertion direction I, and two of the fixation element receiving apertures 1658 are outer apertures 1670 that extend through the body 1646 at an upward angle relative to the insertion direction I. The inner apertures 1668 are configured to receive respective fixation elements, such as fixation element 62 shown in FIGS. 4A and 4B, to thereby attach the intervertebral implant 1622 to the inferior vertebral body 10b. Similarly, the outer apertures 1670 are configured to receive respective fixation elements 62 to thereby attach the intervertebral implant 1622 to the superior vertebral body 10a. It should be appreciated, however, that the inner apertures 1668 can extend through the body 1646 at an upwards angle and the outer apertures 1670 can extend through the body 1646 at a downwards angle, as desired. Moreover, it should be appreciated that the support member 1634 can define any number of fixation element receiving apertures 1658 as desired.

As shown in FIG. 17D, the apertures 1658 each define internal threads 1678. The internal threads 1678 are configured to engage external threads 80 defined by a head 82 of the respective fixation element 62 that is received within the apertures 1658. It should be appreciated, however, that the apertures 1658 can be void of threads as desired. The orientation of the apertures 1658 may be configured such that the fixation elements that are received by the apertures 1658 may have an insertion variance of +/−5 degrees and do not allow toggling or settling. Once fully received, the fixation elements may lock to the frame 1626 to thereby increase the surgeon's reassurance of good screw trajectories and can act as a safety by preventing possibilities of over-insertion during implantation.

Figure 18A:
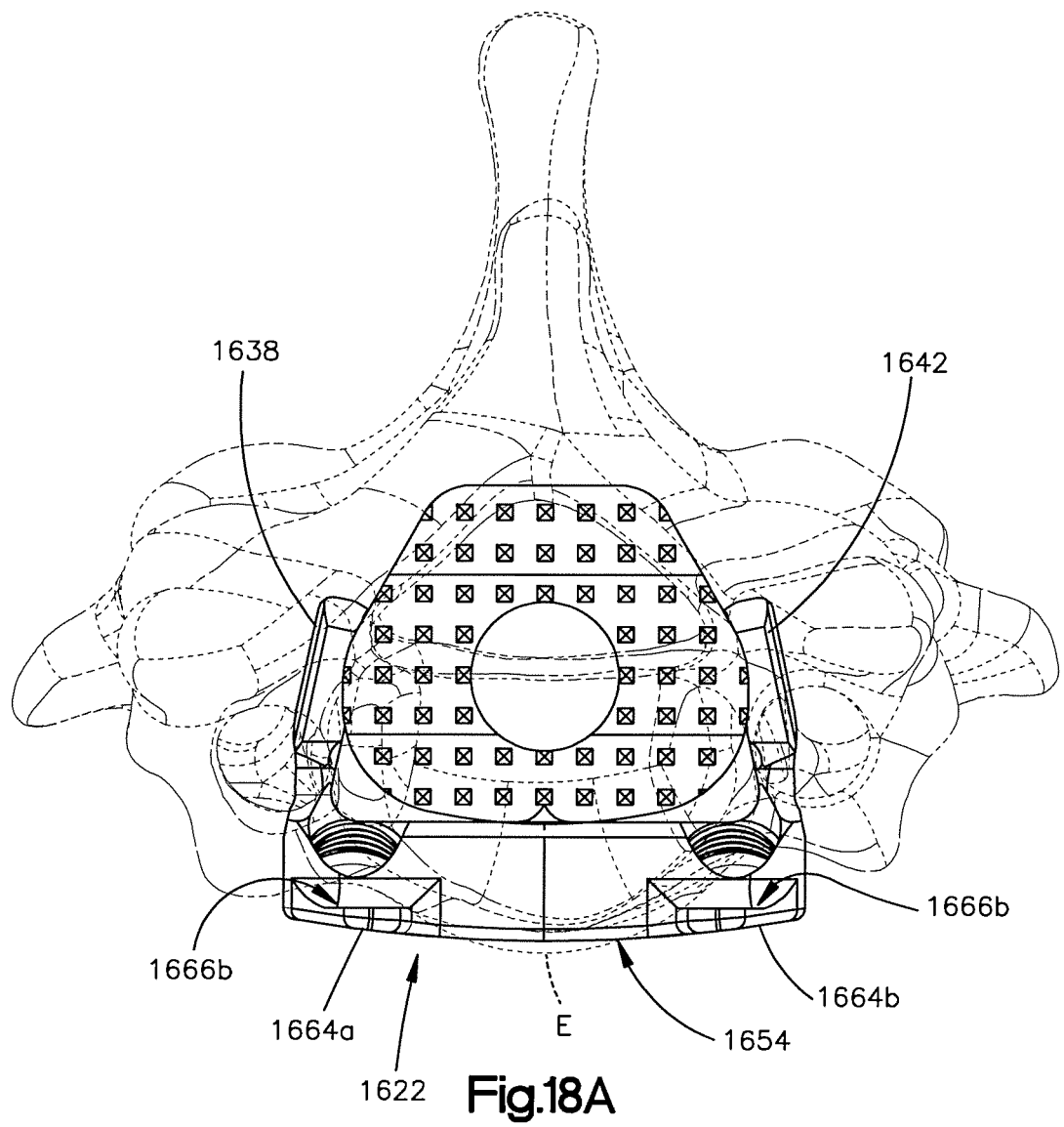
FIG. 18A is a top plan view of the intervertebral implant shown in FIG. 17A, inserted into an intervertebral space defined between first and second vertebral bodies.
Figure 18B:
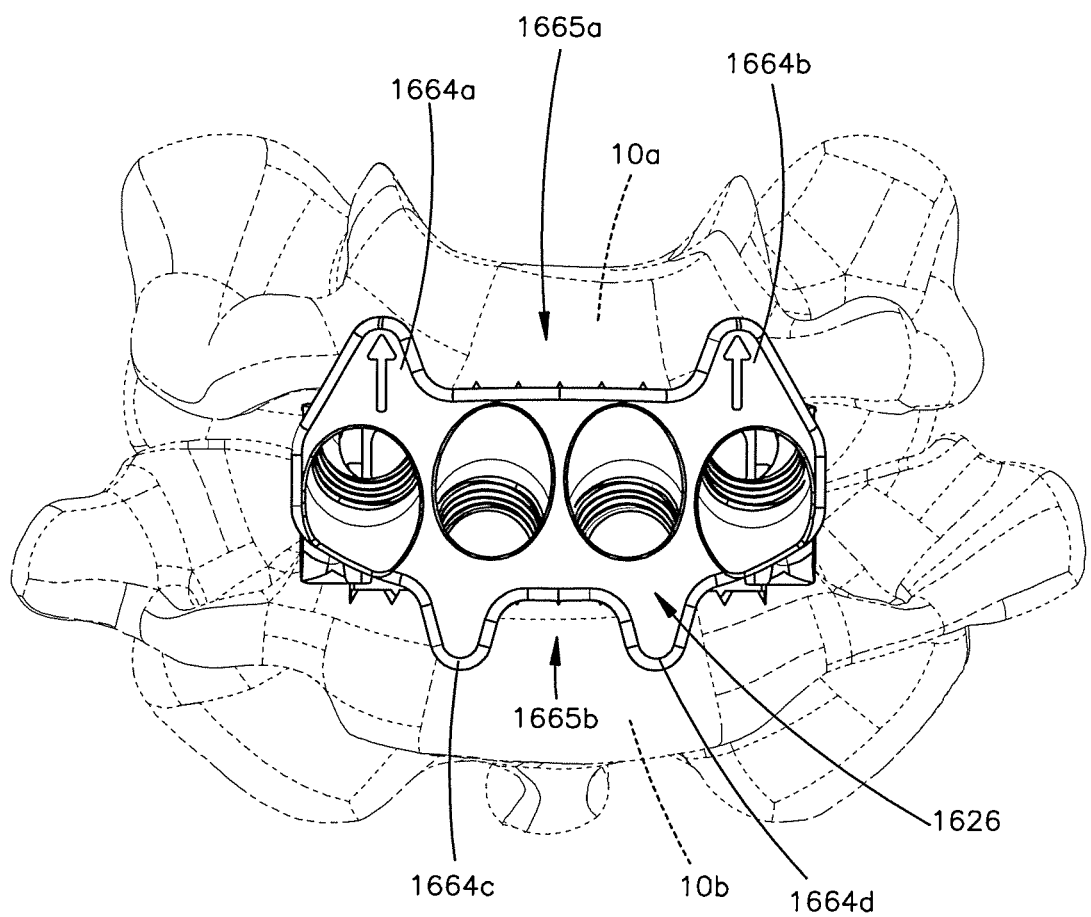
FIG. 18B is a front elevation view of the intervertebral implant shown in FIG. 18A.
Figure 18C:
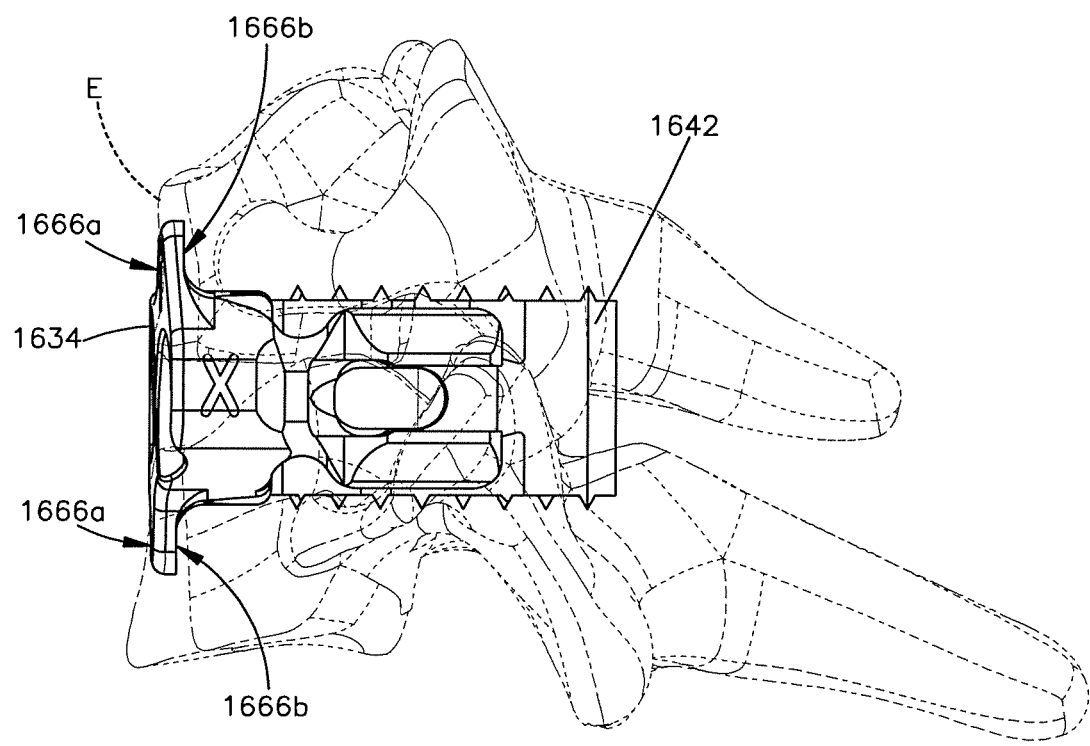
FIG. 18C is a side elevation view of the intervertebral implant shown in FIG. 18A.

As shown in FIGS. 17C and 17D, the support member 1634 can include at least a first tab 1664*a* and a second tab 1664*b* that extend from the first vertebral body facing surface 1647 along a common direction, such as along the first direction, such that first tab 1664*a* and the second tab 1664*b* are spaced from each other along a second direction that is substantially perpendicular to the first direction so as to define a gap 1665*a* between the first and second tabs 1664*a* and 1664*b*. As shown in FIGS. 18A-18C, the gap 1665*a* is sized or otherwise configured to receive a portion of the first vertebral body when the first and second arms 1638 and 1642 are inserted into the intervertebral space. As shown in FIG. 17D, the first tab is spaced from second tab 1664*b* by a first distance $G_1$. The first distance $G_1$ can be any distance so long as a portion of the first vertebral body can extend into the gap 1665*a*.

With continued reference to FIGS. 17C and 17D, the support member 1634 can further include a third tab 1664*c* and a fourth tab 1664*d* that extend from the second vertebral body facing surface 1648 along a common direction, such as along the first direction, and away from the first and second tabs 1664*a* and 1664*b* such that the third tab 1664*c* and fourth tab 1664*d* are spaced from each other along the second direction so as to define a gap 1665*b* between the third and fourth tabs 1664*c* and 1664*d*. The gab 1665*b* between the third and fourth tabs 1664*c* and 1664*d* is configured to receive a portion of the second vertebral body when the first and second arms 1638 and 1642 are inserted into the intervertebral space. As shown in FIG. 17D, the third tab 1664*c* is spaced from fourth tab 1664*d* by a second distance $G_2$. The second distance $G_2$ can be any distance so long as a portion of the second vertebral body can extend into the gap 1665*b*. As shown, the second distance $G_2$ can be less than the first distance $G_1$. It should be appreciated, however, that the first and second distances $G_1$ and $G_2$ can substantially the same or the second distance $G_2$ can be greater than the first distance $G_1$, as desired. The first and second tabs can be equidistant from a centerline of the frame and the third and fourth tabs can be equidistant from the centerline of the frame. It should be appreciated, however, that Each of the tabs 1664*a*-1664*d* defines a front surface 1666*a* and an opposed bone contacting surface 1666*b*. The front surfaces 1666*a* of each tab 1664*a*-1664*d* can be flush with or otherwise coincident with the front face 1654 as illustrated. It should be appreciated, however, that the front surfaces 1666*a* can be offset with respect to the front face 1654, as desired. The bone contacting surfaces 1666*b* of the first and second tabs 1664*a* and 1664*b* are configured to abut the first vertebral body and bone contacting surfaces 1666*b* of the third and fourth tabs 1664*c* and 1664*d* are configured to abut the second vertebral body when the first and second arms 1638 and 1642 are inserted into the intervertebral space. When the frame is implanted into the intervertebral space, anterior surfaces of the first and second vertebral bodies can be flush with or extend beyond the front faces of the tabs.

As shown in FIGS. 17A-17C, the first arm 1638 and the second arm 1642 each extend from the support member 1634 and define a first distal terminal end 1683 and a second distal terminal end 1684, respectively. The first and second arms 1638 and 1642 each define a proximal portion 1685 and a distal portion 1686. The proximal portions 1685 are narrowed so that the first and second arms 1638 and 1642 can flex. The distal portions 1686 can be configured as support portions that define first and second vertebral body contacting surfaces that contact the vertebral bodies so as to support the vertebral bodies 10*a* and 10*b* relative to each other. The arms 1638 and 1642 can be similar to the arms 38 and 42 and can define first and second lengths that are between about 50% and about 100% of an anterior-posterior length of the intervertebral space. As illustrated, the arms 1638 and 1642 have a length that is less than the lengths of the arms 38 and 42. It should be appreciated, however, that the arms 1638 and 1642 can have any lengths as desired. The first arm 1638 includes a first inner spacer contacting surface 1688 and the second arm 1642 includes a second inner spacer contacting surface 1692 that is spaced from the first inner spacer contacting surface 1688 along the second direction, such as the lateral direction A. The inner surface of the support member 1634, the first inner spacer contacting surface 1688, and the second inner spacer contacting surface 1692 together define a void 1694 that is configured to receive and grip a spacer body 1630, such as a spacer body 1630 consisting of cancellous bone.

Figure 17E:
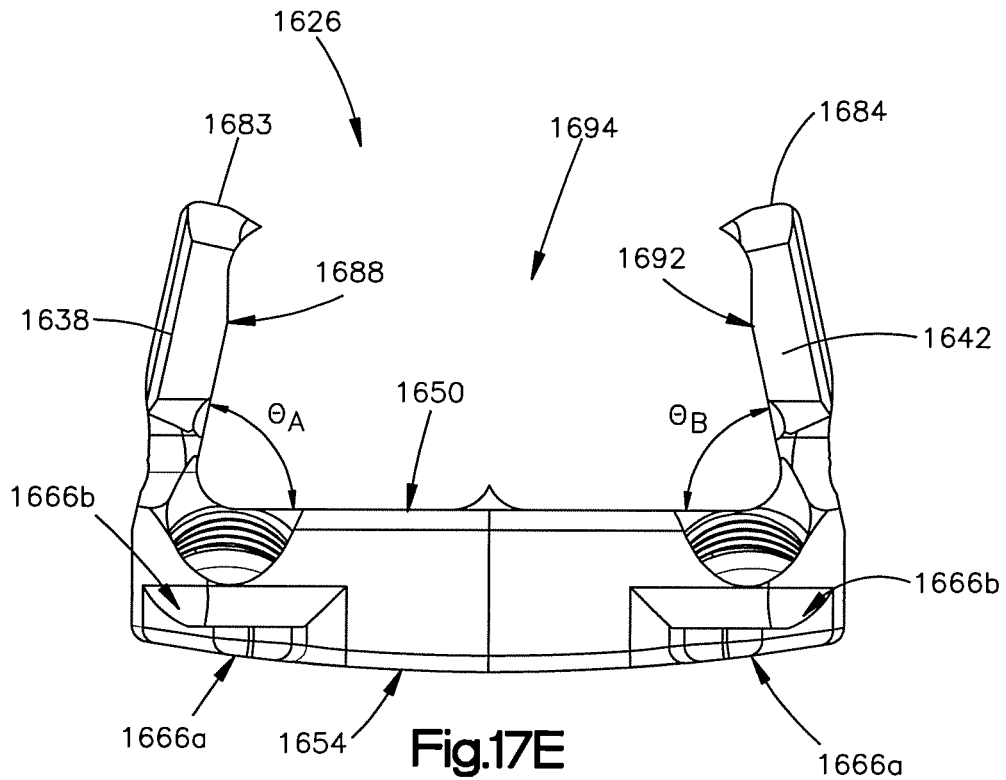
FIG. 17E is a top plan view of the intervertebral implant frame shown in FIG. 17C.
Figure 17F:
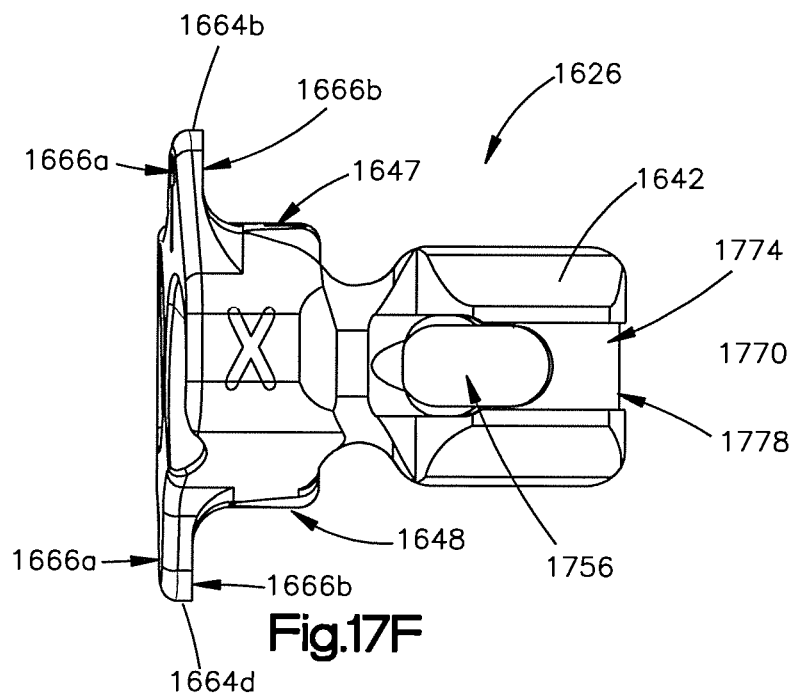
FIG. 17F is a side elevation view of the intervertebral implant frame shown in FIG. 17C.

As shown in FIGS. 17E and 17F, the first and second arms 1638 and 1642 extend from the support member 1634 such that the first and second arms 1638 and 1642 are angled toward each other so as to push the spacer body 1630 toward the other of the first and second arms 1638 and 1642 and toward the support member 1634. For example, the inner surface 1650 of the support member 1634 and the first inner spacer contacting surface 1688 form an angle $Ø_A$ that is less than 90 degrees, and the inner surface 1650 of the support member 1634 and the second inner spacer contacting surface 1692 form an angle $θ_B$ that is less than 90 degrees.

As shown in FIG. 17F, each arm 1638 and 1642 can further include a window 1756 that extends laterally through the arms 1638 and 1642. The windows 1756 are configured to provide visual access to the spacer body 1630 through the first and second arms 1638 and 1642 when the frame 1626 is retaining the spacer body 1630. As shown, the windows 1756 are oval shaped and elongate along the longitudinal direction L. It should be appreciated, however, that the windows 1756 can have any shape as desired. For example, the windows 1756 can also be rectangular shaped.

As shown in FIGS. 17C and 17F, each arm 1638 and 1642 includes an engagement member 1770 that is configured to receive a first and a second external expansion force, respectively, from an expansion instrument prior to insertion of the spacer body 1630 into the void 1694 such that at least one of the first and second arms 1638 and 1642 elastically expands or elastically flexes with respect to the other of the first and second arms 1638 and 1642 in response to the expansion forces. As shown in FIG. 17C, the engagement members 1770 each define a dove-tailed slot 1774 that defines an opening 1778 at its distal end such that the expansion instrument can engage the dove-tailed slot 1774 in a direction that is opposite to the insertion direction I of the frame 1626. It should be appreciated, however, that the engagement members 1770 can have any configuration as desired so long as they can receive respective expansion forces.

Now in reference to FIGS. 18A and 18B, the tabs 1664*a*-1664*d* are spaced relative to each other so as to allow at least a portion of an anterior surface or end E of at least one of the first and second vertebral bodies to be substantially flush with or extend beyond the front face 1654 of the support member 1634 when the bone contacting surfaces 1666*b* of at least one such as all of the tabs 1664*a*-1664*d* abut the anterior surfaces or ends E of the first and second vertebral bodies 10*a* and 10*b*. In the illustrated embodiment and as shown in FIG. 18A, the gap between the first and second tabs 1664*a* and 1664*b* and the gap between the third and fourth tabs 1664*c* and 1664*d* are each sized such that when the first and second arms 1638 and 1642 are inserted into the intervertebral space the at least a portions of the first and second vertebral bodies extend through the gaps 1665a and 1665b and beyond the front face 1654. Because vertebral bodies 10a and 10b are flush with and/or extend beyond the front face 1654, it can be said that the frame 1626 provides a zero profile at a centerline of the vertebral bodies when the arms 1638 and 1642 are inserted into the intervertebral space.

In use, the intervertebral implant can be inserted into the intervertebral space until the spacer body is disposed in the intervertebral space such that opposed first and second surfaces of the spacer body face respective ones of the first and second vertebral bodies. A common one of the first and second vertebral bodies can be abutted with each of the first and second tabs. And, a portion of the common one of the first and second vertebral bodies is caused to extend at least through a gap that extends between the first and second tabs. A common one of the first and second vertebral bodies can also be abutted by the third and fourth tabs. And, a portion of the common one of the first and second vertebral bodies can be caused to extend at least through a gap that extends between the third and fourth tabs. It should be appreciated that the implant can be prepackaged with the frame retaining the spacer body or the frame can be configured to retain the spacer body immediately prior to insertion into the intervertebral space. It should be appreciated that the spacer body can be synthetic or made of allograft bone.

For example, the first and second arms can be moved from a first position to a second position, whereby first and second spacer contacting surfaces of the first and second arms, respectively, are spaced apart by a first distance when in the first position, and are spaced apart by a second distance that is greater than the first distance when in the second position. The allograft spacer body can then be inserted into the frame between the first and second arms when the first and second arms are in the second position. The first and second arms can then be moved to a third position, whereby the first and second spacer contacting surfaces are spaced apart by a third distance when in the third position, the third distance is less than the second distance such that the arms apply a retention force against the allograft spacer body to thereby retain the allograft spacer body in the frame. Once the implant is inserted into the intervertebral space respective bone anchors can be inserted through the apertures of the frame and into the respective first and second vertebral bodies to thereby attach the implant to the first and second vertebral bodies.

It will be appreciated by those skilled in the art that changes could be made to the embodiments described above without departing from the broad inventive concept thereof. Furthermore, it should be appreciated that the structure, features, and methods as described above with respect to any of the embodiments described herein can be incorporated into any of the other embodiments described herein unless otherwise indicated. For example, the frame 1626 can also include crimp members as shown in FIGS. 10A, 11A, 12A, and 13A. It is understood, therefore, that this invention is not limited to the particular embodiments disclosed, but it is intended to cover modifications within the spirit and scope of the present disclosure. Further, it should be appreciated, that the term substantially indicates that certain directional components are not absolutely perpendicular to each other and that substantially perpendicular means that the direction has a primary directional component that is perpendicular to another direction.

What is claimed:

1. An intervertebral implant frame configured to support a spacer body in an intervertebral space that is defined by a first vertebral body and a second vertebral body, the intervertebral implant frame comprising:
    a support member having a body that defines first and second vertebral body facing surfaces, the second vertebral body facing surface spaced from the first vertebral body facing surface along a first direction, the body further defining at least two fixation element receiving apertures that extend through the support member and are each configured to receive a respective bone fixation element,
    a first tab and a second tab that each extend from the first vertebral body facing surface and are spaced from each other along a second direction that is substantially perpendicular to the first direction so as to define a gap that extends between the first and second tabs along the second direction, each of the first and second tabs being configured to abut the first vertebral body when the intervertebral implant is inserted in the intervertebral space;
    first and second arms that extend from the support member and include, respectively, a first inner spacer contacting surface and a second inner spacer contacting surface that is spaced from the first inner spacer contacting surface along the second direction such that the first arm and the second arm are configured to grip and retain the spacer body, the first arm including a first expansion instrument engagement member defining a first dove-tailed slot open at a distal end of the first dove-tailed slot such that the first dove-tailed slot is configured to receive an expansion instrument in a direction that is opposite an insertion direction of the intervertebral implant frame, the second arm including a second expansion instrument engagement member defining a second dove-tailed slot open at a distal end of the second dove-tailed slot such that the second dove-tailed slot is configured to receive the expansion instrument in the direction that is opposite the insertion direction,
    wherein the gap is configured to receive a portion of the first vertebral body when each of the first and second tabs abuts the first vertebral body.

2. The intervertebral implant frame of claim 1, wherein the support member further includes third and fourth tabs that each extend from the second vertebral body facing surface along the first direction and away from the first and second tabs such that the third tab and the fourth tab are spaced from each other along the second direction so as to define a gap between the third and fourth tabs.

3. The intervertebral implant frame of claim 2, wherein the gap between the third and fourth tabs is configured to receive a portion of the second vertebral body when the first and second arms are inserted into the intervertebral space.

4. The intervertebral implant frame of claim 3, wherein the first and second tabs each defines a bone contacting surface that is configured to abut the first vertebral body when the first and second arms are inserted into the intervertebral space, and the third and fourth tabs each defines a bone contacting surface that is configured to abut the second vertebral body when the first and second arms are inserted into the intervertebral space.

5. The intervertebral implant frame of claim 4, wherein the support member body defines a front face and an inner face spaced from the front face along a third direction that is substantially perpendicular to the first and second directions, and wherein the gap between the first and second tabs and the gap between the third and fourth tabs are each sized such that when the first and second arms are inserted into the intervertebral space portions of the first and second vertebral bodies extend through the gaps and beyond the front face.

6. The intervertebral implant frame of claim 3, wherein the first tab is spaced from the second tab along the second direction by a first distance, and the third tab is spaced from the fourth tab along the second direction by a second distance that is less than the first distance.

7. The intervertebral implant frame of claim 1, wherein the first and second arms are capable of retaining a spacer body consisting of cancellous bone.

8. The intervertebral implant frame of claim 1, wherein the first arm and the second arm are angled toward each other such that an inner face of the support member and the first inner spacer contacting surface forms an angle that is less than 90°, and the inner face of the support member and the second inner spacer contacting surface forms an angle that is less than 90°.

9. The intervertebral implant frame of claim 1, wherein the first and second arms define first and second lengths that are between about 50% and 100% of an anterior-posterior length of the intervertebral space.

10. The intervertebral implant frame of claim 1, wherein the first and second tabs have an equidistant spacing from a centerline of the frame.

11. The intervertebral implant frame of claim 1, wherein at least one of the first and second arms is configured to elastically expand with respect to the other of the first and second arms in response to an expansion force.

12. The intervertebral implant frame of claim 1, further comprising at least one tab that extends from the second vertebral body facing surface along the first direction.

13. The intervertebral implant frame of claim 12, wherein the support member body defines an inner face and a front face spaced from the inner face along a third direction that is substantially perpendicular to the first and second directions, and wherein the first tab, the second tab and the at least one tab are spaced relative to each other so as to allow at least a portion of an anterior surface of at least one of the first and second vertebral bodies to be substantially flush with or extend beyond the front face of the support member body.

14. The intervertebral implant frame of claim 12, wherein each of the first tab, the second tab, and the at least one tab defines a respective bone contacting surface and a respective front face spaced from the respective bone contacting surface along a third direction that is substantially perpendicular to the first and second directions, and wherein the first tab, the second tab, and the at least one tab are spaced relative to each other so as to allow at least a portion of an anterior surface of at least one of the first and second vertebral bodies to be substantially flush with or extend beyond the front faces of the first, second, and at least one tabs when the bone contacting surfaces of the first, second, and at least one tabs abut the anterior surfaces of the first and second vertebral bodies.

* * * * *